US012685667B2

(12) United States Patent
Kim

(10) Patent No.: US 12,685,667 B2
(45) Date of Patent: Jul. 21, 2026

(54) COOLING APPARATUS AND COOLING METHOD

(71) Applicant: RECENSMEDICAL, INC., Ulsan (KR)

(72) Inventor: Gun-Ho Kim, Ulsan (KR)

(73) Assignee: RECENSMEDICAL, INC., Ulsan (KR)

( * ) Notice: Subject to any disclaimer, the term of this patent is extended or adjusted under 35 U.S.C. 154(b) by 160 days.

(21) Appl. No.: 18/609,980

(22) Filed: Mar. 19, 2024

(65) Prior Publication Data

US 2024/0261135 A1     Aug. 8, 2024

Related U.S. Application Data

(63) Continuation of application No. 17/340,633, filed on Jun. 7, 2021, now Pat. No. 12,138,200, which is a
(Continued)

(30) Foreign Application Priority Data

Dec. 7, 2018     (KR) ........................ 10-2018-0157478
Mar. 8, 2019     (KR) ........................ 10-2019-0027184

(51) Int. Cl.
*A61F 7/00*          (2006.01)
*A61M 19/00*          (2006.01)

(52) U.S. Cl.
CPC .... *A61F 7/0085* (2013.01); *A61F 2007/0059* (2013.01); *A61F 2007/0063* (2013.01); *A61F 2007/0087* (2013.01); *A61M 19/00* (2013.01)

(58) Field of Classification Search
CPC .. A61F 7/0085; A61F 7/00; A61F 2007/0059; A61F 2007/0063;
(Continued)

(56) References Cited

U.S. PATENT DOCUMENTS 3,948,269 A     4/1976  Zimmer
4,412,538 A     11/1983  Yamauchi et al.
(Continued)

FOREIGN PATENT DOCUMENTS

CN          203163568 U          8/2013
CN          103488210 A          1/2014
(Continued)

OTHER PUBLICATIONS

Office Action dated Jan. 3, 2025 for U.S. Appl. No. 18/739,744.
(Continued)

*Primary Examiner* — Ankit D Tejani
*Assistant Examiner* — Joshua Brendon Solomon
(74) *Attorney, Agent, or Firm* — Dinsmore & Shohl LLP; Yongsok Choi, Esq.

(57)          ABSTRACT

A cooling apparatus and a cooling method are proposed. The cooling device may spray a coolant received from a coolant reservoir toward a target region to cool the target region. The cooling device may include a spraying unit from which the coolant is sprayed, a valve configured to regulate a flow of the coolant, and a control unit configured to control opening and closing of the valve. When cooling starts. the control unit may control a first cooling mode in which a temperature of the target region is decreased and a second cooling mode in which the temperature of the target region is maintained in a predetermined temperature range to be sequentially performed.

10 Claims, 47 Drawing Sheets

10000

Related U.S. Application Data continuation of application No. PCT/KR2019/017328, filed on Dec. 9, 2019.

(60) Provisional application No. 62/847,167, filed on May 13, 2019.

(58) Field of Classification Search
CPC ...... A61F 2007/0087; A61F 2007/0052; A61F 2007/0093; A61F 2007/0096; A61F 2007/0295; A61F 2007/0004; A61F 2007/0086; A61F 2007/0285; A61M 19/00; A61M 35/003; A61M 11/042; A61M 11/047; A61M 11/006; A61M 21/00; A61M 2021/0066; A61M 2202/0225; A61M 2202/0266; A61M 2202/03; A61M 2205/3368; A61M 2205/3606; A61M 2205/3633; A61M 2205/364; A61M 2205/3653; A61M 2205/3673; A61M 2205/50; A61M 2205/8225; A61B 18/0218; A61B 18/203; A61B 2018/0029; A61B 2018/00452; A61B 2018/00642; B05B 9/005; B05B 9/0833

See application file for complete search history.

(56) References Cited

U.S. PATENT DOCUMENTS

| | | | |
|---|---|---|---|
| 5,653,113 | A | 8/1997 | Sawano |
| 5,979,454 | A | 11/1999 | Anvari et al. |
| 6,226,996 | B1 | 5/2001 | Weber et al. |
| 10,349,997 | B1 | 7/2019 | O'Reilly |
| 10,993,827 | B2 | 5/2021 | Kim |
| 11,207,488 | B2 | 12/2021 | Kim |
| 12,138,200 | B2 | 11/2024 | Kim |
| 2004/0111087 | A1 | 6/2004 | Stern et al. |
| 2005/0261753 | A1 | 11/2005 | Littrup et al. |
| 2006/0200117 | A1 | 9/2006 | Hermans |
| 2009/0124972 | A1 | 5/2009 | Fischer et al. |
| 2009/0171333 | A1 | 7/2009 | Hon |
| 2011/0060322 | A1 | 3/2011 | Manstein |
| 2011/0137268 | A1 | 6/2011 | Thomason et al. |
| 2011/0152850 | A1 | 6/2011 | Niedbala et al. |
| 2013/0035680 | A1* | 2/2013 | Ben-Haim ............... A61N 5/04 606/33 |
| 2013/0184694 | A1 | 7/2013 | Fourkas et al. |
| 2013/0296811 | A1 | 11/2013 | Bangera et al. |
| 2016/0016777 | A1 | 1/2016 | Orita |
| 2016/0058488 | A1 | 3/2016 | Fourkas et al. |
| 2016/0249970 | A1 | 9/2016 | Ye et al. |
| 2019/0290881 | A1 | 9/2019 | Kim |
| 2021/0290430 | A1 | 9/2021 | Kim |

FOREIGN PATENT DOCUMENTS

| | | |
|---|---|---|
| CN | 105026302 A | 11/2015 |
| CN | 107366567 A | 11/2017 |
| GB | 1443069 A | 7/1976 |
| GB | 2002236 A | 2/1979 |
| JP | H08304242 A | 11/1996 |
| JP | H11206799 A | 8/1999 |
| JP | 2002-505155 A | 2/2002 |
| JP | 2004-515270 A | 5/2004 |
| JP | 4049358 B2 | 2/2008 |
| JP | 2008-545462 A | 12/2008 |
| JP | 2009-034273 A | 2/2009 |
| JP | 2009-056320 A | 3/2009 |
| JP | 2012-143279 A | 8/2012 |
| JP | 2014-198238 A | 10/2014 |
| JP | 2017-051645 A | 3/2017 |
| JP | 2017-113635 A | 6/2017 |
| KR | 20-1998-0005117 U | 3/1998 |
| KR | 10-0200669 B1 | 6/1999 |
| KR | 10-2004-0093706 A | 11/2004 |
| KR | 10-0786539 B1 | 12/2007 |
| KR | 10-0790758 B1 | 12/2007 |
| KR | 10-0851274 B1 | 8/2008 |
| KR | 10-2011-0119640 A | 11/2011 |
| KR | 1020120040760 A | 4/2012 |
| KR | 10-2012-0115703 A | 10/2012 |
| KR | 10-1300120 B1 | 8/2013 |
| KR | 10-1386137 B1 | 4/2014 |
| KR | 10-2014-0069431 A | 6/2014 |
| KR | 10-2015-0062305 A | 6/2015 |
| KR | 10-2016-0114810 A | 10/2016 |
| KR | 10-2016-0121019 A | 10/2016 |
| KR | 10-2017-0083399 A | 7/2017 |
| KR | 10-2017-0089842 A | 8/2017 |
| KR | 10-2017-0130470 A | 11/2017 |
| KR | 10-2018-0054247 A | 5/2018 |
| KR | 10-1840346 B1 | 5/2018 |
| KR | 10-2018-0109828 A | 10/2018 |
| KR | 10-1905830 B1 | 10/2018 |
| KR | 10-2018-0109827 A | 10/2019 |
| KR | 10-2020-0070095 A | 6/2020 |
| KR | 20-0493630 Y1 | 5/2021 |
| WO | 2006051542 A1 | 5/2006 |
| WO | WO 2013/176857 A1 | 11/2013 |
| WO | WO 2018/093141 A2 | 5/2018 |
| WO | WO 2019/209081 A1 | 10/2019 |

OTHER PUBLICATIONS

Written Decision on Registration dated Feb. 1, 2024 for KR 10-2023-0119555.

Notice of Allowance dated Apr. 10, 2024 for U.S. Appl. No. 17/340,633.

European Extended Search Report dated Jan. 12, 2022 for EP 19791867.5.

European Extended Search Report dated Sep. 29, 2022 for EP 19891927.6.

European Extended Search Report dated Feb. 3, 2023 for EP 22208099.6.

International Search Report and Written Opinion dated Aug. 14, 2019 for PCT/KR2019/005105.

International Search Report and Written Opinion dated Mar. 27, 2020, for PCT/KR2019/017328.

Korean Office Action dated Nov. 26, 2019 for KR 10-2018-0049108—w/ Trans.

Korean Office Action dated Nov. 27, 2019 for KR 10-2018-0049109—w/ Trans.

Korean Notice of Allowance dated Jun. 24, 2020 for KR 10-2018-0049109—w/ Trans.

Korean Office Action dated Dec. 6, 2019 for KR 10-2018-0049110—w/ Trans.

Korean Office Action dated Dec. 9, 2019 for KR 10-2018-0049115—w/ Trans.

Korean Office Action dated May 10, 2020 for KR 10-2018-0049115, with Eng. Translation.

Korean Office Action dated Dec. 10, 2019 for KR 10-2018-0049117—w/ Trans.

Korean Notice of Allowance dated May 10, 2020 for KR 10-2018-0049117.

Korean Office Action dated Oct. 8, 2019 for KR 10-2018-0052601.

Korean Second Office Action, with translation, dated Oct. 28, 2019 for KR 10-2018-0052601.

Korean Office Action dated Oct. 21, 2021 with English Translation, for KR 10-2021-0104443.

Korean Office Action dated May 24, 2023 with English Translation, for KR 10-2021-0104443.

Office Action Dated Dec. 24, 2020 for U.S. Appl. No. 17,036,269.

Final Office Action Dated Apr. 13, 2021 for U.S. Appl. No. 17,036,269.

Office Action dated Dec. 8, 2020 for U.S. Appl. No. 17/036,311.

Notice of Allowance dated Feb. 14, 2024 for U.S. Appl. No. 17/340,633.

(56)            References Cited

OTHER PUBLICATIONS

Korean Notice of Allowance, with English translation, dated Sep. 3, 2024, for KR 10-2019-0139178.
Corrected Notice of Allowance dated May 17, 2024, for U.S. Appl. No. 17/340,633.
Notice of Allowance dated Oct. 9, 2024, for U.S. Appl. No. 17/340,633.
Chinese First Office Action, re CN Application No. 202210751575. 1, issued on Jun. 26, 2025, with English Translation.
Notice of Allowance for Chinese Application No. 202210751633.0 issued May 12, 2026 with English translation.
3rd Office Action Chinese Application No. 202210751575.1 issued on Apr. 10, 2026 with English translation.

* cited by examiner

10000

<u>10000</u>

10000

10000

COOLANT SUPPLY UNIT ————— 1000

FLOW REGULATING UNIT ————— 2000

SPRAYING UNIT ————— 4000

CONTROL UNIT ————— 5000

Figure 8:
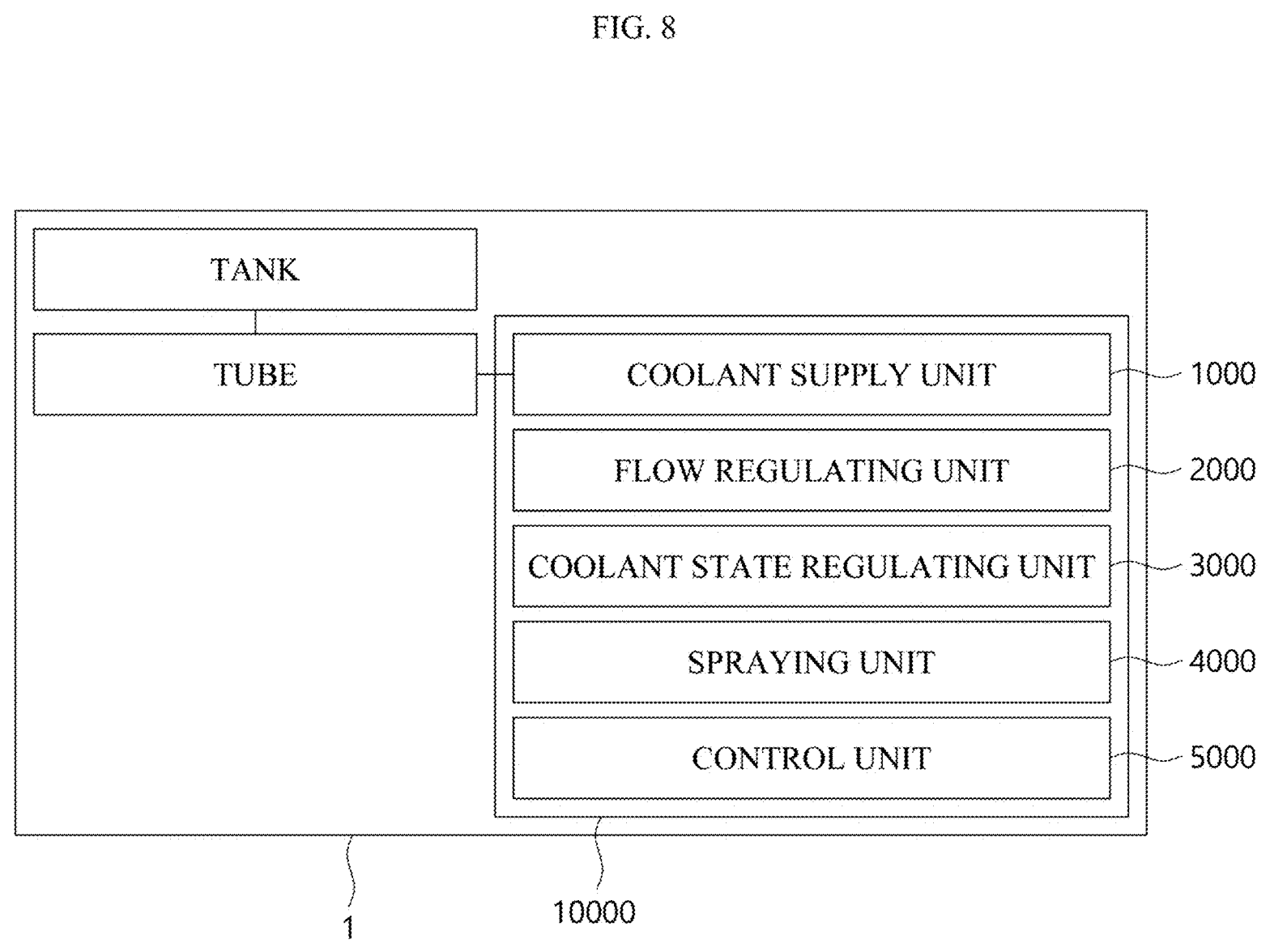

| | |
|---|---|
| COOLANT SUPPLY UNIT | 1000 |
| FLOW REGULATING UNIT | 2000 |
| COOLANT STATE REGULATING UNIT | 3000 |
| SPRAYING UNIT | 4000 |
| CONTROL UNIT | 5000 |

TANK

TUBE

TTR 30.0°C 30.0
20.0
10.0
0.0
-10.0
-20.0

-20.0°C

TTR

COOLING APPARATUS AND COOLING METHOD

CROSS-REFERENCE TO RELATED APPLICATIONS

This application is a continuation of U.S. patent application Ser. No. 17/340,633, filed on Jun. 7, 2021, which is a continuation of International Patent Application No. PCT/KR2019/017328, filed on Dec. 9, 2019, which claims priority to and the benefit of Korean Patent Application No. 10-2018-0157478, filed on Dec. 7, 2018, Korean Patent Application No. 10-2019-0027184, filed on Mar. 8, 2019, PCT Application No. PCT/KR2019/005105, filed on Apr. 26, 2019, and U.S. Provisional Patent Application No. 62/847,167, filed on May 13, 2019, the disclosures of each of which are incorporated herein by reference in their entireties.

BACKGROUND

Technical Field

The present disclosure relates to a cooling method and a cooling device using a coolant, and more particularly, to a cooling method and a cooling device capable of spraying a coolant to selectively cool a target region.

Description of Related Technology

Medical cooling technology using cooling is used for the purpose of eliminating pain, anesthesia, removing lesions, treating acne, controlling pigmentation, treating hair loss, topical fat reduction, plastic surgery, relieving itching, reducing inflammation, suppressing autoimmune responses, or the like.

Particularly, in the medical field, cryogens, ice, thermoelectric elements, cooled air or water are typical materials used in cooling-technology.

Taking into consideration that heat capacity of body tissues is high, cooling-medical technology based on cryogens is the most efficient means for cooling body tissues and is actively discussed in the field of dermatology to remove various types of lesions.

SUMMARY

The present disclosure is directed to providing a cooling device and a cooling method capable of stably implementing cooling conditions required for various clinical effects such as effective destruction of cells in lesions, minimization of destruction of normal cells surrounding the cells in lesions, cooling anesthesia, and immune activation by cooling.

An embodiment of the present application provides a cooling device that sprays a coolant received from a coolant reservoir toward a target region to cool the target region, the cooling device including a spraying unit from which the coolant is sprayed, a valve configured to regulate a flow of the coolant, and a control unit configured to control opening and closing of the valve, wherein, when cooling starts, the control unit controls a first cooling mode in which a temperature of the target region is decreased and a second cooling mode in which the temperature of the target region is maintained in a predetermined temperature range to be sequentially performed, and an absolute value of a temperature gradient with time of the target region when the first cooling mode is performed is larger than an absolute value of a temperature gradient with time of the target region when the second cooling mode is performed.

An embodiment of the present application provides a cooling device that cools a target region using a coolant received from a coolant reservoir, the cooling device including a spraying unit configured to spray the coolant toward the target region, a valve configured to regulate a flow of the coolant, a control unit configured to control opening and closing of the valve, and a temperature sensor configured to convert an intensity of infrared rays emitted from a detection region into heat and detect the converted heat to check an average temperature of the detection region, wherein, when the coolant is sprayed through the spraying unit, the control unit checks the average temperature of the detection region through the temperature sensor (the detection region is included in a region to which the coolant is sprayed and includes a site with lowest temperature in the target region), and, when the temperature of the detection region is a predetermined temperature or lower, an opening time per unit time of the valve is reduced.

The advantageous effects of a cooling device and a cooling method according to the present disclosure are as follows.

By continuously keeping a pressure of a coolant at a location adjacent to a coolant spraying unit, the coolant can reach a predetermined thermodynamic state with a fast dynamic response. Also, by controlling a thermodynamic phase of the coolant right before the coolant is sprayed to a treatment site, the coolant can be sprayed to the treatment site while a temperature of the coolant is controlled to a desired temperature. In addition, by controlling heat at the treatment site other than a target site to be cooled, it is possible to prevent excessive cooling from occurring outside a target region.

By regulating a cooling site while rapidly controlling the temperature of the coolant as described above, it is possible to stably implement cooling protocols for various treatment protocols for various clinical effects, such as cooling anesthesia, treatment on cells in lesions using immune activation, and treatment to kill cells in lesions with minimal normal cell destruction, or treatment in which various clinical effects are combined, such as treatment to break down cells in lesions while pain is minimized by first applying cooling conditions corresponding to cooling anesthesia.

Also, by a coolant or cooling medium, which is jetted from the spraying unit, cooling a cooling tip which comes in contact with the body of a patient, the cooling efficiency can be increased, and by accurately targeting an affected area that should be cooled, pain relief and anesthetic effects on the affected area can be enhanced.

BRIEF DESCRIPTION OF THE DRAWINGS

FIG. 8 is a diagram for describing a cooling system 1 including a cooling device 10000 according to a second embodiment of the present application.

FIGS. 31 and 32 are diagrams for describing changes in a coolant spraying region according to movement of an aero-fin 4150 in the nozzle unit 4100 according to an embodiment of the present application.

FIG. 38 is a diagram for describing a method of controlling a valve 2100 in a case in which the cooling device 10000 according to an embodiment of the present application operates in two different cooling modes while performing onetime cooling operation.

DETAILED DESCRIPTION

Figure 1:
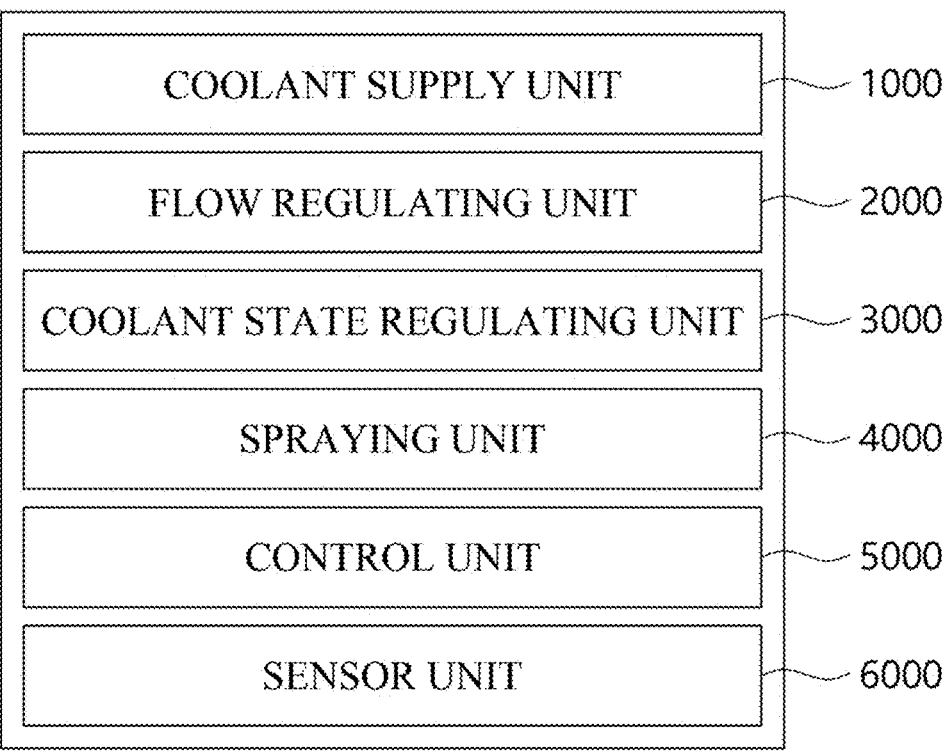
FIG. 1 is a diagram for describing a configuration of a cooling device 10000 according to an embodiment of the present application.

Generally, it is difficult to control temperature of cryogens and cooling means other than the cryogens are unable to efficiently cool the body tissues, despite the clinical expectations that medical cooling technology might be used for many medical symptoms, it has not been used effectively beyond surgical therapies such as tissue resection so far.

In the means of cooling body tissues with cryogens that is most used in medical cooling treatment nowadays, the control of cooling temperature is performed by simply controlling a speed of a coolant, mixing the coolant with another fluid, or the like, and thus precise control is difficult over a wide range of temperatures.

For example, even until now, precision in temperature control is insufficient for applying medical cooling technology in the medical fields such as anesthesia, pain relief, acne treatment, skin pigmentation control, and hair loss treatment, and thus satisfactory results have not been obtained.

The present disclosure is directed to providing a more precise and efficient cooling technology, and the means of the present disclosure are expected to bring further effects in the aforementioned treatment for lesions.

Specifically, the present disclosure will introduce a cooling device that, in applying a cryogen (referred to as "coolant") to the body, controls a thermodynamic state of the coolant and is typically capable of precisely controlling temperature by the Joule-Thomson effect. Particularly, in order to apply medical cooling technology, the present disclosure may precisely and promptly control a temperature of a target region of the body, a depth of the target region, an area of the target region, and the like.

In the present disclosure, in presenting medical cooling technology using coolant, products and technologies for anesthetizing or treating eyes and body tissues other than the eyes will be mainly described.

In order to perform intravitreal injection or vision correction surgery such as LASTK or LASEK, the patient's eye needs to be anesthetized first. In the case of anesthetic agents, the anesthetic effect may be insufficient due to the limitation that the anesthetic agents take time to reach pain-sensing nerves and the possibility that chemicals may not diffuse well. To effectively compensate for this, the present disclosure proposes a device and method capable of spraying a coolant to the eye to anesthetize the eye before performing intravitreal injection, vision correction surgery, and the like.

Particularly, in the case of ocular anesthesia, precision is required to effectively anesthetize only the portion where an injection needle is inserted, and promptness is required to reduce waiting time for the main medical treatment after the patient is anesthetized. For precise control of ocular anesthesia, doctors have a high demand for medical devices that are easy to use and have high portability. Therefore, coolants for anesthesia need to be mounted in small amounts in medical devices so as not to impede the maneuverability of the medical devices by the doctors.

A cooling device proposed by the present disclosure that applies a container-type or cartridge-type coolant product which holds a small amount of coolant has high portability and is designed to facilitate replacement of the coolant product when the coolant is used up.

On the other hand, when medical cooling technology is applied to parts of the body other than the eye, such as the skin, the amount of coolant consumed is very large due to the need to perform multiple treatments per patient. In this case, the coolant product which is attached to and detached from a medical device and replaced may degrade the usability of the medical device by the doctors due to rapid consumption of coolant. Therefore, the present disclosure also discloses a cooling device which receives a coolant from a high-capacity coolant reservoir or the like outside the cooling device so that there is less need for replacement even after multiple treatments.

The two types of cooling devices have the advantage that they can be selectively applied according to the lesion and the preference of the doctor, and are not mutually exclusive.

The above-mentioned objectives, features, and advantages of the present application will become more apparent from the following detailed description related to the accompanying drawings. However, the present application may be modified in various ways and have various embodiments. Hereinafter, specific embodiments which are illustrated in the drawings will be described in detail.

In the drawings, the thicknesses of layers and regions are exaggerated for clarity. Also, when an element or layer is described as being "on" or "above" another element or layer, this includes both a case in which the element or layer is directly on the other element or layer and a case in which still another element or layer is interposed therebetween. In principle, like reference numerals refer to like elements throughout. Also, elements having the same function within the scope of the same idea shown in the drawings of each embodiment will be described using the same reference numerals, and redundant description thereof will be omitted.

When detailed description of known functions or configurations related to the present application is deemed as having the possibility of unnecessarily obscuring the gist of the present application, the detailed description thereof will be omitted. Also, ordinals (e.g., first, second, seventh, eighth, ninth, tenth, etc.) used in the description process of the present specification are merely identification symbols for distinguishing one element from another element.

In addition, the terms "module" and "unit" which are used to refer to elements in the following embodiments have been given or interchangeably used with other terms only in consideration of ease of writing the specification and thus do not have meanings or roles that are distinguished from each other.

In the following embodiments, a singular expression includes a plural expression unless the context clearly indicates otherwise.

In the following embodiments, terms such as "include" or "have" designate that features or elements described herein are present and do not preclude the possibility of adding one or more other features or elements in advance.

In the following embodiments, when a part such as a film, a region, or an element is described as being on or above another part, this not only includes a case in which the part is directly on the other part, but also includes a case in which still another film, region, element, or the like is interposed therebetween.

In the drawings, sizes of elements may have been exaggerated or reduced for convenience of description. For example, the size and thickness of each element shown in the drawings are arbitrarily shown for convenience of description, and the present disclosure is not necessarily limited thereto.

When a certain embodiment may be implemented differently, a specific process may be performed in an order different from a described order. For example, two processes described in succession may be performed substantially concurrently or performed in the reverse order.

In the following embodiments, when films, regions, or elements are described as being connected, this not only includes a case in which the films, regions, or elements are directly connected, but also includes a case in which the films, regions, or elements are indirectly connected with other films, regions, or elements interposed therebetween. For example, in the present specification, when films, regions, or elements are described as being electrically connected, this not only includes a case in which the films, regions, or elements are directly electrically connected, but also includes a case in which the films, regions, or elements are indirectly electrically connected with other films, regions, or elements interposed therebetween.

An embodiment of the present application may provide a cooling device that sprays a coolant received from a coolant reservoir toward a target region to cool the target region, the cooling device including a spraying unit from which the coolant is sprayed, a valve configured to regulate a flow of the coolant, and a control unit configured to control opening and closing of the valve, wherein, when cooling starts, the control unit controls a first cooling mode in which a temperature of the target region is decreased and a second cooling mode in which the temperature of the target region is maintained in a predetermined temperature range to be sequentially performed, and an absolute value of a temperature gradient with time of the target region when the first cooling mode is performed is larger than an absolute value of a temperature gradient with time of the target region when the second cooling mode is performed.

To prevent excessive cooling of the target region, the control unit may control the valve to repeat opening and closing while the first cooling mode and the second cooling mode are performed.

The control unit may control the valve to repeat an operation of being opened during a first time and being closed during a second time in the first cooling mode and may control the valve to repeat an operation of being opened during a third time and being closed during a fourth time in the second cooling mode, wherein the first time is the same as the third time and the second time is shorter than the fourth time to control a cooling speed in the first cooling mode to be higher than a cooling speed in the second cooling mode.

The control unit may control the valve to, during a fifth time, repeat the operation of being opened during the first time and being closed during the second time in the first cooling mode and, during a sixth time, repeat the operation of being opened during the third time and being closed during the fourth time in the second cooling mode, wherein, to minimize pain felt by a subject who receives cooling treatment using the cooling device, the control unit controls the valve so that the fifth time is shorter than the sixth time.

The spraying unit may include a nozzle unit configured to spray the coolant and a guide unit configured to restrict a spraying region of the coolant sprayed through the nozzle unit.

After performing the first cooling mode and the second cooling mode, the control unit may control the valve to perform a third cooling mode before ending cooling, and in the third cooling mode, the control unit may control the valve so that the target region reaches a temperature higher than the predetermined temperature range in order to separate between the guide unit and the target region.

The guide unit may include at least one region having an elastic force.

One side of the guide unit that comes in contact with the target region may have a diagonal shape, and one side of the guide unit that comes in contact with the cooling device may include at least one periphery hole configured to discharge the coolant.

According to an embodiment of the present application, the cooling device may further include a spraying temperature regulating unit configured to receive an electrical signal of the control unit and heat the coolant, and the control unit may control the valve to be opened in the first cooling mode and the second cooling mode and may control the spraying temperature regulating unit to heat the sprayed coolant in the second cooling mode.

The spraying temperature regulating unit may be a thermoelectric element.

According to an embodiment of the present application, the cooling device may further include a temperature sensor configured to detect the temperature of the target region, and the control unit may control the performance of the second cooling mode to start on the basis of the temperature of the target region.

The control unit may end the second cooling mode on the basis of whether a predetermined amount of time has elapsed after the temperature of the target region reached a target cooling temperature.

An embodiment of the present application provides a cooling device that cools a target region using a coolant received from a coolant reservoir, the cooling device including a spraying unit configured to spray the coolant toward the target region, a valve configured to regulate a flow of the coolant, a control unit configured to control opening and closing of the valve, and a temperature sensor configured to convert an intensity of infrared rays emitted from a detection region into heat and detect the converted heat to check an average temperature of the detection region, wherein, when the coolant is sprayed through the spraying unit, the control unit checks the average temperature of the detection region through the temperature sensor (the detection region is included in a region to which the coolant is sprayed and includes a lowest temperature site of the target region), and, when the temperature of the detection region is a predetermined temperature or lower, the control unit reduces an opening time of the valve per unit time.

The spraying unit may spray the coolant to include a free jet in which the coolant is sprayed in a direction toward the target region and a spread jet in which the coolant collides with a subject to be treated, which includes the target region, and is emitted in a different direction from the free jet, so that, on a surface of the subject to be treated, at least a central cooling region including a region having the lowest temperature, a non-cooling region including a region having the highest temperature, and a boundary region including a region having a temperature between the highest temperature of the central cooling region and the lowest temperature of the non-cooling region are formed on the basis of a virtual isotherm, and the control unit may control the valve on the basis of the temperature of the detection region included in the boundary region.

The central cooling region may include a region having a difference within a central critical temperature with respect to the lowest temperature, the boundary region may include a region having a difference within a barrier critical temperature with respect to the highest temperature of the central cooling region, and the non-cooling region may include a region having a difference within a non-cooling critical temperature with respect to the highest temperature.

The central critical temperature, the barrier critical temperature, and the non-cooling critical temperature may be the same temperature, and the central critical temperature, the barrier critical temperature, and the non-cooling critical temperature may be a value obtained by dividing a difference between the highest temperature of the subject to be treated and the lowest temperature of the subject to be treated by 3.

An outer shape of the detection region may have higher eccentricity than an outer shape of the central cooling region.

The control unit may control the valve on the basis of the temperature of the detection region included in the central cooling region, wherein the detection region does not include the non-cooling region.

The control unit may reduce an opening time of the valve per unit time in a case in which the temperature of the detection region is a first critical temperature or lower and may increase the opening time of the valve per unit time in a case in which the temperature of the detection region is a second critical temperature or higher, wherein the first critical temperature is lower than the second critical temperature.

In a case in which the valve is controlled to be open during a first time, closed during a second time, and repeat the opening and closing during a third time, the control unit may reduce the opening time of the valve per unit time in a form of increasing the second time.

An embodiment of the present application provides a cooling device that sprays a coolant received from a coolant reservoir toward a target region to cool the target region, the cooling device including a nozzle unit from which the coolant is sprayed, a valve configured to regulate a flow of the coolant, and a control unit configured to control opening and closing of the valve, wherein the control unit controls a first cooling mode and a second cooling mode, in which an opening time of the valve per unit time is shorter as compared to the first cooling mode, to be performed and controls one of the first cooling mode and the second cooling mode to be selectively performed on the basis of information on the coolant stored in the coolant reservoir.

The control unit may control the valve to operate in the first cooling mode in a case in which a residual amount of the coolant stored in the coolant reservoir is a predetermined numerical value or less.

After the first cooling mode or the second cooling mode is performed, the control unit may count the number of times the cooling mode has been performed and may, on the basis of the number of times the cooling mode has been performed, check whether the residual amount of the coolant stored in the coolant reservoir is the predetermined numerical value or less.

According to an embodiment of the present application, the cooling device may further include a coolant reservoir receiving unit in which the coolant reservoir is accommodated, and the control unit may, when the coolant reservoir is accommodated in the coolant reservoir receiving unit, reset the number of times the cooling mode has been performed.

The control unit may include a first control module configured to control the first cooling mode and the second cooling mode to be performed and a second control module configured to control information on the coolant stored in the coolant reservoir to be checked, and the cooling device may further include a first power source configured to supply power to the first control module and a second power source configured to supply power to the second control module.

To prevent excessive cooling of the target region, the control unit may control the valve to repeat opening and closing while the first cooling mode and the second cooling mode are performed.

The control unit may control the valve to repeat an operation of being opened during a first time and being closed during a second time in the first cooling mode and may control the valve to repeat an operation of being opened during a third time and being closed during a fourth time in the second cooling mode, wherein the first time is the same as the third time and the second time is shorter than the fourth time to control an opening time of the valve per unit time in the first cooling mode to be longer than that in the second cooling mode.

The control unit may control the valve to, during a fifth time, repeat the operation of being opened during the first time and being closed during the second time in the first cooling mode and, during a sixth time, repeat the operation of being opened during the third time and being closed during the fourth time in the second cooling mode, wherein the first time is the same as the third time, the second time is shorter than the fourth time, and the fifth time is longer than the sixth time to control the opening time of the valve per unit time and the total opening time of the valve in the first cooling mode to be longer than those in the second cooling mode.

In a case in which the temperature of the coolant stored in the coolant reservoir is a predetermined numerical value or more, the control unit may control the valve to operate in the first cooling mode.

According to an embodiment of the present application, the cooling device may further include a first temperature sensor configured to detect a temperature relating to the sprayed coolant and a second temperature sensor configured to detect a temperature relating to an external environment in which the cooling device is used, wherein, on the basis of a detected value of the first temperature sensor and a detected value of the second temperature sensor, the control unit checks whether the temperature of the coolant stored in the coolant reservoir is a predetermined numerical value or more.

The first temperature sensor may come in contact with the nozzle unit to measure the temperature of the nozzle unit, and the second temperature sensor may be spaced apart from the nozzle unit and a flow path of the coolant to measure the temperature of the outside where the cooling device is used.

An embodiment of the present application provides a cooling device that sprays a coolant received from a coolant reservoir toward a target region to cool the target region, the cooling device including a spraying unit from which the coolant is sprayed, a valve configured to regulate a flow of the coolant, a radiant energy provision unit configured to provide radiant energy to a region related to the target region, and a control unit configured to control opening and closing of the valve to control the target region to be cooled to a target temperature, wherein, to reduce a size of a region corresponding to the target temperature as compared to when the provision of the radiant energy by the radiant energy provision unit is not performed, the control unit controls the radiant energy emitted through the radiant energy provision unit to heat at least a partial region outside the target region while the coolant, which has passed through the valve, is sprayed to the target region, and the heating by the radiant energy emitted through the radiant energy provision unit does not occur on a lowest temperature site on the surface of the subject to be treated which includes the target region.

The spraying unit may spray the coolant so that a temperature of a coolant spraying region is lower than a previous temperature of the subject to be treated, and the radiant energy provision unit provides radiant energy so that an average temperature of a radiant energy providing region by the radiant energy provision unit is higher than an average temperature of the target region, wherein the lowest temperature site of the coolant spraying region does not overlap with the radiant energy providing region.

The spraying unit may spray the coolant to include a free jet in which the coolant is sprayed toward the target region and a spread jet in which the coolant collides with the subject to be treated, which includes the target region, and is emitted in a different direction from the free jet, so that, on a surface of the subject to be treated, at least a central cooling region including a region having the lowest temperature, a non-cooling region including a region having the highest temperature, and a boundary region including a region having a temperature between the highest temperature of the central cooling region and the lowest temperature of the non-cooling region are formed on the basis of a virtual isotherm, and the radiant energy provision unit provides radiant energy to surround the central cooling region.

The control unit may allow the radiant energy emitted through the radiant energy provision unit to be provided to the target region and a region outside the target region while the coolant, which has passed through the valve, is sprayed to the target region, and due to combination of a cooling phenomenon of the target region and a heating phenomenon of the radiant energy provision unit, the heating by the radiant energy emitted through the radiant energy provision unit may not occur on the lowest temperature site on the surface of the subject to be treated.

The radiant energy emitted through the radiant energy provision unit may be provided to the target region and a region outside the target region so that the shape of the region corresponding to the target temperature corresponds to a circular shape.

The radiant energy provision unit may include a light source configured to emit radiant energy and a light guide unit configured to guide the radiant energy emitted from the light source along a predetermined optical path.

The light source may be a Light Amplification by the Stimulated Emission of Radiation (LASER) emission device.

To prevent excessive cooling of the target region, the control unit may control the valve to repeat opening and closing while cooling is performed and may control the radiant energy provision unit to, regardless of whether the valve is open or closed, provide radiant energy while cooling is performed.

The spraying unit may spray the coolant in a vertical direction with respect to the surface of the subject to be treated, and the radiant energy provision unit may provide radiant energy in a different direction from the spraying unit with respect to the surface of the subject to be treated.

The control unit may control the valve to perform cooling for a predetermined amount of time so that the epidermis and dermis of the subject to be treated are cooled and may control the radiant energy provision unit to provide radiant energy while cooling is performed so that the epidermis of the subject to be treated is heated.

The cooling device according to an embodiment of the present application may include a nozzle unit which includes a first channel through which the coolant flows, a cooling medium which provides a second channel through which the coolant which passed through the nozzle unit moves so that the coolant discharged from the nozzle unit is cooled while passing through the second channel, and a cooling tip which is coupled to the cooling medium and cooled by coming in direct contact with the cooling medium and the coolant which passed through the cooling medium.

The cooling tip may include a cooling medium coupling portion which is coupled to the cooling medium and a coolant contact portion which is disposed at a front end of the cooling medium coupling portion and includes an outer surface whose width or diameter is smaller than that of the cooling medium coupling portion.

A front end of the coolant contact portion may consist of a closed surface, and the inside of the coolant contact portion and the cooling medium coupling portion may be defined as an empty space.

The cooling tip may be cooled by receiving a flow of heat transmitted by conduction from the cooling medium through the cooling medium coupling portion and receiving a flow of heat transmitted by any one of conduction or convection from the coolant that passed through the cooling medium through the coolant contact portion.

The cooling tip and the cooling medium may be made of metal.

The cooling tip may be replaced and used.

The cooling tip may further include a marker configured to, in a case in which an eye of a patient comes in contact with the front end of the coolant contact portion, form a mark on the eye, and a diameter of the marker may be 3 mm or less.

A diameter of a front end of the first channel may be less than a diameter of a region of the first channel excluding the front end thereof.

A diameter of the second channel may be larger than the diameter of the first channel and substantially the same as an outer diameter of the nozzle unit.

The cooling device may further include a nozzle unit insulator disposed to surround the nozzle unit to position the nozzle unit and an elastic coupling portion which is coupled to a rear end of the nozzle unit insulator and includes a spring configured to provide elasticity to the nozzle unit insulator.

The cooling tip and the cooling medium may receive an elastic force, which is provided from the elastic coupling portion, from the nozzle unit insulator and be pressed against each other.

The cooling device may further include an insulator cover disposed to surround the nozzle unit insulator, a front end cover disposed to surround the insulator cover, and a rear end cover disposed at a rear end of the front end cover and coupled to the rear end of the front end cover and the rear end of the nozzle unit insulator.

The coolant contact portion may be exposed to the outside through an opening of the front end cover.

The cooling device may further include a nozzle guide unit which is disposed between the cooling medium and the nozzle to induce coupling and alignment of the cooling medium and the nozzle and an orifice which is disposed between the nozzle guide unit and the nozzle unit to transfer the coolant to the cooling medium.

A cooling device according to an embodiment of the present application includes a nozzle unit including a first channel through which a coolant flows, a valve connected to the nozzle unit to control the amount of the coolant transferred to the nozzle unit, a cooling medium cooled by the coolant received from the nozzle unit, and a cooling tip cooled due to a flow of heat received from the cooling medium, wherein the cooling medium is inserted into and coupled to an inner space of the cooling tip.

The cooling tip may include a first front end portion and a first rear end portion whose width or diameter is larger than that of the first front end portion, and the cooling medium may include a second front end portion and a second rear end portion whose width or diameter is larger than that of the first front end portion, wherein the second front end portion is inserted into and coupled to the first front end portion, and the second rear end portion is inserted into and coupled to the first rear end portion.

The first front end portion and the second front end portion may each include a closed front end surface, and a front end surface of the second front end portion may come in contact with a front end surface of the first front end portion to cool the cooling tip.

The first front end portion, the first rear end portion, the second front end portion, and the second rear end portion may have a cylindrical outer circumferential shape.

The cooling tip may further include a marker configured to, in a case in which an eye of a patient comes in contact with the first front end portion, form a mark on the eye, and a diameter of the marker may be 3 mm or less.

The cooling device may further include a nozzle guide unit which is disposed between the cooling medium and the nozzle to induce coupling and alignment of the cooling medium and the nozzle and an orifice which is disposed between the nozzle guide unit and the nozzle unit to transfer the coolant to the cooling medium.

In a case in which the nozzle guide unit, the nozzle unit, and the orifice are coupled, a front end of the orifice may be disposed to pass through a front end of the nozzle guide unit.

A diameter of a path through which the coolant flows in the orifice may be smaller than the diameter of the first channel.

The coolant discharged from the nozzle unit or the orifice may cool the cooling medium using at least any one method of conduction or convection.

The cooling device may further include a nozzle unit insulator disposed to surround the nozzle unit to position the nozzle unit and an elastic coupling portion which is coupled to a rear end of the nozzle unit insulator and includes a spring configured to provide elasticity to the nozzle unit insulator.

The cooling tip and the cooling medium may receive an elastic force, which is provided from the elastic coupling portion, from the nozzle unit insulator and be pressed against each other.

The cooling medium may further include a groove, and a temperature sensor may be disposed in the groove.

A heat capacity of the cooling tip may be 0.1 to 5 times a heat capacity of the cooling medium.

The cooling device may further include a spraying temperature regulating unit disposed between the nozzle unit and the cooling medium to control the temperature of the coolant transferred to the cooling medium.

<Cooling Device 10000>

A cooling device 10000 according to an embodiment of the present application may be a device used in lowering a temperature of a target region TR in an environment in which at least one phenomenon of radiation, conduction, and/or convection occurs.

The cooling device 10000 according to an embodiment of the present application may be a device that sprays a gas-, liquid-, and/or solid-phase material (e.g., coolant) to lower the temperature of the target region TR.

For example, the cooling device 10000 may spray a coolant, and the coolant may come into contact with the target region TR. A heat transfer due to conduction may occur through the contact between the target region TR and the coolant. The cooling device 10000 may cool at least a portion of the target region TR through the above-described process.

As another example, the cooling device 10000 may spray a coolant, and the coolant may flow in one region of the target region TR. In the target region TR, a heat transfer due to convection may occur through the flow of the coolant. The cooling device 10000 may cool at least a portion of the target region TR through the above-described process.

As still another example, the cooling device 10000 may spray a coolant, and the coolant may remain in the target region TR. In the target region TR, a heat transfer may occur due to a phase change of a portion of the coolant remaining in the target region TR. As a more specific example, when a coolant in a liquid phase remains in the target region TR and then the phase of the coolant changes to a gas phase, the coolant may receive heat corresponding to heat of evaporation or heat of sublimation from the target region TR and cool the target region TR.

The above-described processes may simultaneously occur or sequentially occur, or only at least one of the above-described phenomena may occur. Also, the present application is not limited thereto, and the cooling device 10000 may cool the target region TR using various other methods that may be easily practiced by those of ordinary skill in the art.

The cooling device 10000 according to an embodiment of the present application may perform cooling of the target region TR. For example, the target region TR may be one region related to the human body. As a specific example, the target region TR may be the stratum corneum, the stratum granulosum, the stratum spinosum, and/or the stratum basale which are located in the epidermis. As another specific example, the target region TR may be sweat glands, hair follicles, sebaceous glands, and/or the layer of fat which are located in the dermis. As another specific example, the target region TR may be oral mucosa, conjunctiva, or the like. As still another specific example, the target region TR may be a tissue including an epidermal tissue, an epithelial tissue, a connective tissue, a cartilage tissue, an osseous tissue, blood, lymph, a muscle tissue, and/or a nerve tissue.

The cooling device 10000 according to an embodiment of the present application may be utilized in various fields. For example, the cooling device 10000 may be used to perform cooling of the target region TR and induce an anesthetic effect in the target region TR or used for effective destruction of cells in lesions. Alternatively, the cooling device 10000 according to an embodiment of the present application may perform cooling of the target region TR to induce effects such as fat reduction in a local site, reduction of skin aging, relief of itching, reduction of inflammation, and suppression of autoimmune responses. Alternatively, the cooling device 10000 according to an embodiment of the present application may perform cooling of the target region TR to cause a hypopigmentation effect, thereby eliminating or reducing hyperpigmentation such as freckles.

The present application is not limited thereto, and the cooling device 10000 may be used to stably implement cooling conditions to cause various clinical effects.

One objective of the present application is to provide the cooling device 10000 capable of performing precise cooling control.

Hereinafter, the cooling device 10000 according to an embodiment of the present application will be described.

1. Elements of Cooling Device 10000

FIG. 1 is a diagram for describing a configuration of the cooling device 10000 according to an embodiment of the present application.

The cooling device 10000 according to an embodiment of the present application may include a coolant supply unit 1000, a flow regulating unit 2000, a coolant state regulating unit 3000, a spraying unit 4000, a control unit 5000, and a sensor unit 6000.

However, the above description only clearly discloses that the cooling device 10000 according to an embodiment of the present application may include the above elements, and the cooling device 10000 according to an embodiment of the present application may also be a device from which at least one of the above elements of the cooling device 10000 is omitted, a device that further includes an element other than the above elements of the cooling device 10000, or a device in which some of the above elements of the cooling device 10000 are provided in a plurality.

Hereinafter, for better understanding, functions, structures, and specific embodiments of the coolant supply unit 1000, the flow regulating unit 2000, the coolant state regulating unit 3000, the spraying unit 4000, the control unit 5000, and the sensor unit 6000 will be described.

1.1 Coolant Supply Unit 1000

The coolant supply unit 1000 according to an embodiment of the present application may perform a function of providing a coolant. The coolant supply unit 1000 may perform a function of providing a coolant flowing in the cooling device 10000. The coolant supply unit 1000 may perform a function of providing a coolant flowing in the flow regulating unit 2000, the coolant state regulation unit 3000, and/or the spraying unit 4000.

The coolant may be in a gas-phase, liquid-phase, and/or solid-phase. In other words, the coolant may be in a gas phase, a liquid phase, or a solid phase or may be a mixture in which coolants in at least two or more phases are distributed together.

The coolant may be a material capable of performing cooling by the Joule-Thomson effect when the coolant is sprayed at normal pressure. For example, the coolant may be nitrogen ($N_2$), nitrous oxide ($N_2O$), carbon dioxide ($CO_2$), or the like. However, the coolant is not limited to materials disclosed in the present application and may also correspond to general materials used as coolants by those of ordinary skill in the art.

The coolant supply unit 1000 according to an embodiment of the present application may perform a function of supplying coolant. The coolant supply unit 1000 may perform a function of supplying a coolant to the cooling device 10000. The coolant supply unit 1000 may perform a function of supplying a coolant to the flow regulating unit 2000, the coolant state regulating unit 3000, and/or the spraying unit 4000.

The coolant supply unit 1000 according to an embodiment of the present application may perform a function of supplying a coolant so that the coolant moves to at least a partial region of the elements of the cooling device 10000. For example, the coolant may be influenced by gravity and move from the coolant supply unit 1000 to at least a partial region of the elements of the cooling device 10000. As another example, the coolant may be affected by a pressure difference and move from the coolant supply unit 1000 to at least a partial region of the elements of the cooling device 10000.

The coolant supply unit 1000 according to an embodiment of the present application may be disposed at one end of a flow path formed in the cooling device 10000.

The coolant supply unit 1000 according to an embodiment of the present application may be disposed at a position spaced apart from the spraying unit 4000 in the flow path formed in the cooling device 10000. The coolant supply unit 1000 may be disposed at a position most spaced apart from the spraying unit 4000 in the flow path formed in the cooling device 10000.

According to an embodiment of the present application, the coolant supply unit 1000 may include a reservoir 1100.

The reservoir 1100 according to an embodiment of the present application may perform a function of keeping a coolant for an arbitrary time. The reservoir 1100 may perform a function of holding a coolant for an arbitrary time. The reservoir 1100 may perform a function of accommodating a coolant for an arbitrary time. The reservoir 1100 may perform a function of storing a coolant for an arbitrary time.

A relatively high-pressure environment may be formed in the reservoir 1100. A high-pressure environment whose pressure is higher than atmospheric pressure may be formed in the reservoir 1100. A high-pressure environment whose pressure is higher than the those in the flow regulation unit 2000, the coolant state regulation unit 3000, and/or the spraying unit 4000 may be formed in the reservoir 1100.

According to an embodiment of the present disclosure, the reservoir 1100 may keep $CO_2$ therein. Here, an environment having a pressure in a range of 1 to 150 bar may be formed in the reservoir 1100. More preferably, an environment having a pressure in a range of 3 to 100 bar may be formed in the reservoir 1100. More preferably, an environment having a pressure in a range of 5 to 80 bar may be formed in the reservoir 1100. More preferably, an environment having a pressure in a range of 20 to 70 bar may be formed in the reservoir 1100.

The reservoir 1100 may have a pressure-resistant characteristic. The reservoir 1100 may be implemented to withstand a pressure of a coolant stored therein. The reservoir 1100 may be formed to have a pressure-resistant characteristic by properly selecting a material, a thickness, and/or a welding method of the reservoir 1100. For example, the reservoir 1100 may be made of metal. As a specific example, the reservoir 1100 may be made of steel or stainless steel. As another example, the reservoir 1100 may be made of a composite material. As a specific example, the reservoir 1100 may be made of a composite material including carbon fiber.

The reservoir 1100 may be a tank accommodating a coolant. The reservoir 1100 may be a cartridge accommodating a coolant. The reservoir 1100 may be an ordinary cylinder accommodating a coolant. As an example, the reservoir 1100 may be a tank accommodating low-temperature, high-pressure liquefied nitrogen ($N_2$) or carbon dioxide ($CO_2$) therein.

The cooling device 10000 according to an embodiment of the present application may be provided in a structure in which outflow of a coolant from the reservoir 1100 is prevented.

For example, a structure which prevents outflow of the coolant may be formed in the reservoir 1100. A structure that closes to prevent outflow of the coolant stored in the reservoir 1100 may be formed in the reservoir 1100. A structure that performs an opening operation and a closing operation so that the coolant stored in the reservoir 1100 flows out at a time point at which the coolant should flow out may be formed in the reservoir 1100.

As a specific example, a valve 2100 that allows the coolant stored in the reservoir 1100 to selectively flow out may be provided in the reservoir 1100. The valve 2100 may be opened or closed by a manual operation of a user. Alternatively, the valve 2100 may be opened or closed in response to a specific signal. In this case, the valve 2100 may be opened or closed in response to an electrical signal. Alternatively, the valve 2100 may be opened or closed in response to a pressure change due to a fluid.

As another example, the cooling device 10000 may be provided in the form in which the coolant continuously flows out from the reservoir 1100. A structure that blocks outflow of the coolant may be formed in an element of the coolant that is connected to the reservoir 1100 so that a fluid is movable.

As a specific example, the reservoir 1100 and the flow regulation unit 2000 of the cooling device 10000 may be connected so that a fluid is movable, and continuous outflow of the coolant stored in the reservoir 1100 may be prevented by a coolant outflow blocking structure of the flow regulation unit 2000. Alternatively, the cooling device 10000 may have a pipe formed between the reservoir 1100 and the flow regulation unit 2000, and the pipe and the reservoir 1100 may be connected through an O-ring that prevents coolant loss, thereby preventing coolant outflow.

According to an embodiment of the present application, the cooling device 10000 may include a reservoir receiving unit 1300. The reservoir receiving unit 1300 may be a housing formed to prevent separation of the reservoir 1100 when the reservoir 1100 is installed in the cooling device 10000.

The reservoir receiving unit 1300 should be more clearly understood from the embodiments described below.

According to an embodiment of the present application, the coolant supply unit 1000 may include a transfer unit 1200.

The transfer unit 1200 according to an embodiment of the present application may perform a function of receiving a coolant from the outside and supplying the coolant to the cooling device 10000. For example, the transfer unit 1200 may perform a function of receiving a coolant from a tank disposed outside the cooling device 10000 and supplying the coolant to the cooling device 10000.

The transfer unit 1200 according to an embodiment of the present application may perform a function of providing a passage through which the cooling device 10000 may receive a fluid from the outside. The transfer unit 1200 may perform a function of receiving a coolant from outside the cooling device 10000 and transferring the coolant to at least one element of the cooling device 10000.

As a specific example, the transfer unit 1200 may provide a passage that allows a coolant discharged from a tank physically spaced apart from the cooling device 10000 to flow into the cooling device 10000. The coolant discharged from the tank may pass through the transfer unit 1200 and move to at least one space of the flow regulating unit 2000, the coolant state regulating unit 3000, and/or the spraying unit 4000.

The transfer unit 1200 may have a pressure-resistant characteristic. The transfer unit 1200 may be implemented to withstand a pressure of the passing coolant so that the coolant passing through the transfer unit 1200 does not flow out. The transfer unit 1200 may be formed to have a pressure-resistant characteristic by properly selecting a material, a thickness, and/or a welding method of the transfer unit 1200.

According to an embodiment of the present application, the transfer unit 1200 may have weather resistance and/or heat resistance. The transfer unit 1200 may be implemented using a heat-resistant material in order to prevent a rapid change in a temperature of the coolant passing through the transfer unit 1200. The transfer unit 1200 may be implemented using a weather-resistant material in order to prevent corrosion of the transfer unit 1200 due to contact with external moisture or the like.

As a specific example, the transfer unit 1200 may be made of an aluminum alloy, stainless steel, steel, and/or a copper alloy.

According to an embodiment of the present application, the transfer unit 1200 may be implemented so that a tube in which a coolant may move is connected to the transfer unit 1200. For example, the transfer unit 1200 may be connected through a tube to a tank in which a coolant is kept, and the coolant discharged from the tank may flow into the transfer unit 1200. The tube connecting the tank and the transfer unit 1200 may have flexibility. As a specific example, the tube may be a hose.

The tube connecting the tank and the transfer unit 1200 may have weather resistance and/or heat resistance. For example, the tube connecting the tank and the transfer unit 1200 may be made of rubber.

1.2 Flow Regulating Unit 2000

The flow regulating unit 2000 according to an embodiment of the present application may perform a function of regulating a flow of the coolant moving along a flow path in the cooling device 10000. The flow regulating unit 2000 may perform a function of regulating a flow of the coolant moving to the flow regulating unit 2000, the coolant state regulating unit 3000, and/or the spraying unit 4000.

The flow regulating unit 2000 according to an embodiment of the present application may perform a function of making a difference between a pressure of a moving flow in a flow path disposed at a first side of the flow regulating unit 2000 and a pressure of a moving flow in a flow path disposed at a second side of the flow regulation unit 2000.

For example, the flow regulating unit 2000 may perform a function of forming a turbulent flow or a chocked flow in the coolant passing through the flow regulating unit 2000 so that the flow of the coolant is reduced. Here, due to adiabatic expansion, the temperature of the coolant may be decreased in advance before the coolant is supplied to the spraying unit. In other words, the flow regulating unit 2000 may perform a function of causing a temperature of a fluid at an upstream side of the flow regulating unit 2000 to be higher than a temperature of a fluid at a downstream side of the flow regulating unit 2000.

As another example, the flow regulating unit 2000 may regulate outflow of the coolant passing through the flow regulating unit 2000 and blocking of the outflow of the coolant. When the flow regulating unit 2000 is in a closed state, the flow regulating unit 2000 may perform a function of causing a plurality of coolants to be distributed at the upstream side of the flow regulating unit 2000 while a relatively smaller amount of coolant is distributed at the downstream side of the flow regulating unit 2000. When the flow regulating unit 2000 is in an open state, the flow regulating unit 2000 may perform a function of causing a flow per unit area of the upstream side of the flow regulating unit 2000 to be similar to a flow per unit area of the downstream side of the flow regulating unit 2000.

According to an embodiment of the present application, the flow regulating unit 2000 may include the valve 2100.

The valve 2100 may perform a function of regulating the flow of a coolant. The valve 2100 may perform a function of causing outflow of a coolant passing through the valve 2100 or blocking the outflow of the coolant. Alternatively, the valve 2100 may perform a function of controlling the degree of outflow of the coolant passing through the valve 2100. The valve 2100 may perform a function of controlling the amount of the coolant passing through the valve 2100.

According to an embodiment of the present application, the valve 2100 may regulate a flow of the coolant flowing out to the spraying unit 4000 and affect a temperature change of a target region TR where the coolant flowing out from the spraying unit 4000 reaches. Specific embodiments related thereto will be described in detail below.

The valve 2100 according to an embodiment of the present application may be controlled according to a specific signal. The valve 2100 may perform opening and closing operations in response to an electronic signal generated by the control unit 5000. As a specific example, the valve 2100 may be an electronic valve 2100 (e.g., a solenoid valve 2100), but is not limited thereto.

The valve 2100 according to an embodiment of the present application may be controlled according to a mechanical structure and movement of fluid. The valve 2100 may perform the opening and closing operations according to a pressure formed by a fluid moving along the flow path in the cooling device 10000. As a specific example, the valve 2100 may be a hydraulic valve 2100 (e.g., a pressure-control valve 2100), but is not limited thereto.

The valve 2100 according to an embodiment of the present application may be controlled according to a user's input. The valve 2100 may be placed in an open state or a closed state by the user. As a specific example, the valve 2100 may be a manual valve 2100 (e.g., a globe valve 2100), but is not limited thereto.

The flow regulation unit 2000 according to an embodiment of the present application may include a flow restriction unit.

The flow restriction unit may perform a function of reducing the amount of coolant passing through the flow restriction unit. Alternatively, the flow restriction unit may perform a function of keeping the amount of coolant passing through the flow restriction unit to a flow less than or equal to a predetermined flow.

According to an embodiment of the present application, the flow restriction unit may perform a function of setting the maximum amount of a flow of a coolant flowing out to the spraying unit 4000 to prevent the amount of coolant discharged by passing through the flow restriction unit from exceeding the limit for safety of the cooling device 10000.

1.3 Coolant State Regulating Unit 3000

The coolant state regulating unit 3000 according to an embodiment of the present application may perform a function of regulating a physical state of a coolant. The coolant state regulating unit 3000 may perform a function of regulating a physical state of a coolant passing through the coolant state regulating unit 3000.

The coolant state regulating unit 3000 according to an embodiment of the present application may perform a function of regulating a physical state of a coolant in the cooling device 10000. The coolant state regulating unit 3000 may perform a function of regulating a physical state of a coolant moving through the flow regulating unit 2000 and/or the spraying unit 4000.

For example, the coolant state regulating unit 3000 may control a temperature of a coolant. The coolant state regulating unit 3000 may heat the coolant. Alternatively, the coolant state regulating unit 3000 may cool the coolant. Alternatively, the coolant state regulating unit 3000 may perform heating and/or cooling according to a state of the coolant to keep a temperature of the coolant. Alternatively, the coolant state regulating unit 3000 may perform heating and/or cooling according to a state of the coolant to keep a pressure of the coolant.

According to an embodiment of the present application, the coolant state regulating unit 3000 may include a coolant temperature controller.

The coolant temperature controller may perform a function of heating the coolant. As a specific example, the coolant temperature controller may perform a function of heating the coolant to control the temperature and/or pressure of the coolant.

The coolant temperature controller may perform a function of cooling the coolant. As a specific example, the coolant temperature controller may perform a function of cooling the coolant to control the temperature and/or pressure of the coolant.

The coolant temperature controller may perform a function of heating and cooling the coolant. As a specific example, the coolant temperature controller may perform a function of heating or cooling the coolant to control the temperature and/or pressure of the coolant.

The coolant temperature controller according to an embodiment of the present application may include an element capable of supplying thermal energy. The coolant temperature controller may include one or more heating elements capable of generating thermal energy.

The heating element may generate thermal energy using chemical energy or generate thermal energy using electrical energy. Also, the heating element may generate thermal energy using the Joule-Thomson method which uses a condensable gas.

Alternatively, the heating element may also supply thermal energy using a thermoelectric element such as the Peltier element. In a case in which the heating element is a thermoelectric element, when current is applied to the thermoelectric element, due to the Peltier effect, an endothermic reaction may occur at a first side of the thermoelectric element and an exothermic reaction may occur at a second side of the thermoelectric element.

According to an embodiment of the present application, the cooling device 10000 in which a side corresponding to the second side of the thermoelectric element is disposed to thermally come into contact with a flow path through which the coolant moves may be provided. Here, the thermoelectric element may serve as the coolant temperature controller.

According to another embodiment of the present application, the control unit 5000 may reverse a direction of current applied to the thermoelectric element to control an endothermic reaction to occur at the second side of the thermoelectric element. Here, the coolant flowing through the coolant temperature controller may be cooled by the endothermic reaction by the thermoelectric element.

Therefore, when the thermoelectric element is applied to the coolant temperature controller, the control unit 5000 may control a direction of current applied to the thermoelectric element to heat or cool the coolant passing through the coolant temperature controller.

According to an embodiment of the present application, the cooling device 10000 may include, as the coolant temperature controller, a spraying temperature regulating unit 3100 disposed between the flow regulating unit 2000 and the spraying unit 4000. The spraying temperature regulating unit 3100 may perform a function of controlling a temperature of a coolant discharged from the flow regulating unit 2000 and discharging the coolant at the controlled temperature through the spraying unit 4000. A specific operation related thereto will be described in more detail below.

A coolant cooling unit 3200 according to an embodiment of the present application may include an element capable of supplying cooling energy. The coolant cooling unit 3200 may include one or more cooling elements capable of generating cooling energy.

The cooling element may generate cooling energy by using a Stirling cooler as the cooling device 10000, using a thermodynamic cycle such as a vapor compression refrigeration cycle, using evaporation of liquid, or using the Joule-Thomson method which uses an expanding gas. The cooling element may generate cooling energy by using liquid nitrogen or liquid carbon dioxide.

Alternatively, the cooling element may generate cooling energy using a thermoelectric element such as a Peltier element. The thermoelectric element is an element that performs cooling using the Peltier effect. Here, the Peltier effect refers to a phenomenon in which, when n- and p-type thermoelectric materials are paired and current is caused to flow therein, an exothermic reaction occurs at one side while an endothermic reaction (cooling) occurs at the other side. The Peltier effect, in other words, can be referred to as a heat-pump capable of electrical feedback control.

In a case in which the cooling element is a thermoelectric element, when current is applied to the thermoelectric element, due to the Peltier effect, an endothermic reaction may occur at a first side of the thermoelectric element, and an exothermic reaction may occur at a second side of the thermoelectric element.

According to an embodiment of the present application, the cooling device 10000 in which a side corresponding to the first side of the thermoelectric element is disposed to thermally come into contact with a flow path through which the coolant moves may be provided. Here, the thermoelectric element may serve as the coolant temperature controller.

The coolant temperature controller according to an embodiment of the present application may further include a heat dissipating element. The coolant temperature controller according to an embodiment of the present application may further include an element for dissipating thermal energy naturally generated when the cooling element causes an endothermic reaction.

According to an embodiment of the present application, the cooling device 10000 may include, as the coolant temperature controller, the coolant cooling unit 3200 disposed between the coolant supply unit 1000 and the flow regulation unit 2000. The coolant cooling unit 3200 may perform a function of cooling a coolant received from the coolant supply unit 1000 to control a pressure of the coolant and allowing the coolant with the controlled pressure to pass through the flow regulation unit 2000. A specific operation related thereto will be described in more detail below.

1.4 Spraying Unit 4000

The spraying unit 4000 according to an embodiment of the present application may perform a function of discharging a fluid in the cooling device 10000 to the outside. The spraying unit 4000 according to an embodiment of the present application may perform a function of spraying a fluid in the cooling device 10000 to the outside. The spraying unit 4000 may perform a function of discharging the coolant that passes through the coolant supply unit 1000, the flow regulation unit 2000, and/or the coolant state regulating unit 3000 to the outside.

The spraying unit 4000 according to an embodiment of the present application may include a nozzle unit 4100. The nozzle unit 4100 may perform a function of jetting a coolant flowing in at least one region in the cooling device 10000 to a free space.

The jetted coolant may be in a gas-phase, liquid-phase, and/or solid-phase. In other words, the coolant may be in a gas phase, a liquid phase, or a solid phase, or may be a mixture in which coolants in at least two or more phases are distributed together. In an example, when the coolant is $CO_2$, coolants in a gas phase and a solid phase may be mixed and distributed together in the jetted coolant. In another example, when the coolant is $N_2$, coolants in a gas phase and a liquid phase may be mixed and distributed together in the jetted coolant.

The nozzle unit 4100 according to an embodiment of the present application may perform a function of providing a passage through which the coolant in the cooling device 10000 may be discharged. For example, the nozzle unit 4100 may be a tube formed to allow the coolant flowing in at least one region in the cooling device 10000 to be jetted to a free space.

The nozzle unit 4100 according to an embodiment of the present application may be a tube disposed at one end of a flow path formed in the cooling device 10000.

The nozzle unit 4100 may include a tube having a relatively small cross-sectional area. The nozzle unit 4100 may include a tube having a relatively smaller cross-sectional area as compared to at least any one of the coolant supply unit 1000, the flow regulating unit 2000, the coolant state regulating unit 3000, and/or a pipe between the elements of the cooling device 10000.

The nozzle unit 4100 may have various shapes. For example, the nozzle unit 4100 may be a straight nozzle. Here, a cross-section of the nozzle unit 4100 may have a circular shape having a hollow formed therein. As another example, the nozzle unit 4100 may be an annular nozzle. Here, a cross-section of the nozzle unit 4100 may have a circular shape and may be perforated in a circular shape smaller than the former circular shape. The annular nozzle may have a ring-shaped hollow and have a form in which a coolant is blocked at a central portion thereof and is jetted from an edge of the central portion. As still another example, the nozzle unit 4100 may be a bell nozzle. As yet another example, the nozzle unit 4100 may be an aerospike nozzle. However, the above-listed forms of the nozzle unit 4100 are merely specific examples to help in understanding, and the shape of the nozzle unit 4100 is not limited to the above-listed examples.

The nozzle unit 4100 may have a wear-resistant characteristic. In other words, the nozzle unit 4100 may be made of a material which is not damaged much due to friction. For example, the nozzle unit 4100 may be made of an aluminum alloy, a steel alloy, stainless steel, or a copper alloy, but the material of the nozzle unit 4100 is not limited thereto.

According to an embodiment of the present application, the cooling device 10000 may further include a cooling restriction unit 4500.

The cooling restriction unit 4500 may perform a function of restricting the coolant sprayed from the nozzle unit 4100. The cooling restriction unit 4500 may perform a function of restricting the coolant sprayed from the nozzle unit 4100 based on a predetermined condition. For example, the cooling restriction unit 4500 may perform a function of restricting the coolant sprayed from the nozzle unit 4100 in a case in which the temperature of the coolant sprayed from the nozzle unit 4100 is lower than a predetermined critical temperature.

Restricting the coolant sprayed from the nozzle unit 4100 may refer to restricting spraying of the coolant toward the target region TR by changing the direction of the coolant sprayed from the nozzle unit 4100 or may refer to restricting spraying of the coolant by blocking the spraying of the coolant sprayed from the nozzle unit 4100. However, these are merely some embodiments of the cooling restriction unit 4500, and embodiments of the cooling restriction unit 4500 are not limited to the above-mentioned embodiments.

The cooling restriction unit 4500 will be described in more detail below.

According to an embodiment of the present application, the cooling device 10000 may further include a cooling mitigating unit 4600.

The cooling mitigating unit 4600 may perform a function of mitigating the temperature of the coolant sprayed from the nozzle unit 4100. The cooling mitigating unit 4600 may perform a function of mitigating the temperature of the coolant before the coolant sprayed from the nozzle unit 4100 reaches the target region TR.

Mitigating the temperature of the coolant may refer to performing a heat exchange with the coolant so that the coolant sprayed from the nozzle unit 4100 reaches the target region TR while being at a temperature higher than a temperature of the coolant right after the coolant is sprayed from the nozzle unit 4100. However, this is merely one embodiment of the cooling mitigating unit 4600, and embodiments of the cooling mitigating unit 4600 are not limited to the above-mentioned embodiment.

The cooling mitigating unit 4600 will be described in more detail below.

According to an embodiment of the present application, the spraying unit 4000 may further include a spraying site limiting unit for limiting a region where the coolant discharged from the spraying unit 4000 reaches.

According to an embodiment of the present application, the spraying site limiting unit may include a guide unit 4210 which serves as a barrier that prevents the coolant from reaching a region other than the target region TR.

The guide unit 4210 may perform a function of limiting a region to which the coolant is sprayed so that the region corresponds to the target region TR. The guide unit 4210 may perform a function of limiting a region to which the coolant is sprayed so that the region corresponds to a surface area of the target region TR.

Here, the target region TR may be set to have a surface area suitable for the purpose of treatment. For example, when the purpose of cooling is to perform a cooling anesthetic function for injection, the target region TR may be set to have a surface area of an appropriate size which is large enough to find a site for injection treatment after cooling but does not cause discomfort to the patient due to excessive cold sensation caused by cooling an extremely large region.

For example, when performing a cooling anesthetic function for injection using the cooling device 10000, the guide unit 4210 may keep the surface area of the target region TR in a range of 1 mm² to 50 mm². As a specific example, the guide unit 4210 may keep the surface area of the target region TR in a range of 5 mm² to 20 mm². As a more specific example, the guide unit 4210 may keep the surface area of the target region TR in a range of 5 mm² to 10 mm².

The guide unit 4210 may have various shapes. For example, the guide unit 4210 may have a shape having a quadrilateral cross-section. In other words, the guide unit 4210 may be formed in a shape in which a cross-sectional area of one end disposed relatively adjacent to the target region TR is equal to a cross-sectional area of the other end disposed to be spaced apart from the target region TR. As another example, the guide unit 4210 may have a shape having a conical cross-section. In other words, the guide unit 4210 may be formed in a shape in which a cross-sectional area of one end disposed relatively adjacent to the target region TR is larger than a cross-sectional area of the other end disposed to be spaced apart from the target region TR. As still another example, the guide unit 4210 may have a shape in which one end disposed relatively adjacent to the target region TR has a diagonal shape. However, the above-listed forms of the guide unit 4210 are merely specific examples to help in understanding, and the shape of the guide unit 4210 is not limited to the above-listed examples.

The guide unit 4210 may be made of a material having relatively low thermal conductivity. For example, the guide unit 4210 may be made of a material having relatively low thermal conductivity as compared to the coolant supply unit 1000, the flow regulation unit 2000, the coolant state regulating unit 3000, and/or the nozzle unit 4100. As a specific example, the guide unit 4210 may be made of a material having thermal conductivity lower than or equal to 20 W/m-K. For example, the guide unit 4210 may be made of plastic, but the material of the guide unit 4210 is not limited thereto. As another specific example, the guide unit 4210 may be made of a material having thermal conductivity lower than or equal to 1 W/m-K. For example, the guide unit 4210 may be made of natural rubber, silicone rubber, or the like, but the material of the guide unit 4210 is not limited thereto. The guide unit 4210 may further include at least one periphery hole 4211. Through the periphery hole 4211 formed in the guide unit 4210, an external gas may flow into an inner space of the guide unit 4210. Through the periphery hole 4211 formed in the guide unit 4210, the coolant discharged from the nozzle unit 4100 may be discharged to the outside of the spraying site limiting unit. Through the periphery hole 4211 formed in the guide unit 4210, the coolant discharged from the nozzle unit 4100 may be discharged to the outside of the guide unit 4210.

The number of periphery holes 4211 formed in the guide unit 4210 and the sizes and positions of the periphery holes 4211 may affect the degree of inflow of the external gas. The number of periphery holes 4211 formed in the guide unit 4210 and the sizes and positions of the periphery holes 4211 may affect the time during which the coolant discharged from the nozzle unit 4100 stays in the inner space of the spraying site limiting unit. As a result, the number of periphery holes 4211 formed in the guide unit 4210 and the sizes and positions of the periphery holes 4211 may affect the extent to which the target region TR is cooled.

According to an embodiment of the present application, when the same amount of coolant is sprayed from the spraying unit 4000 of the cooling device 10000, the temperature of the target region TR may be lower in a case in which cooling is performed using the cooling device 10000 in which the size of the periphery hole 4211 formed in the guide unit 4210 is relatively small as compared to the case in which cooling is performed using the cooling device 10000 including the guide unit 4210 in which the size of the periphery hole 4211 formed therein is relatively large. In other words, the smaller the size of the periphery hole 4211 formed in the guide unit 4210, the smaller the amount of coolant required to lower the temperature of the target region TR to a certain temperature.

According to an embodiment of the present application, in a case in which a plurality of periphery holes 4211 are formed in the guide unit 4210, when the same amount of coolant is sprayed from the spraying unit 4000 of the cooling device 10000, the temperature of the target region TR may be lower in a case in which cooling is performed using the cooling device 10000 in which the sum of the cross-sectional areas of the plurality of periphery holes 4211 formed is relatively small as compared to the case in which cooling is performed using the cooling device 10000 in which the sum of the cross-sectional areas of the plurality of periphery holes 4211 formed is relatively large. In other words, the smaller the sum of the cross-sectional areas of the plurality of periphery holes 4211 formed in the guide unit 4210, the smaller the amount of coolant required to lower the temperature of the target region TR to a certain temperature.

According to an embodiment of the present application, the number of periphery holes 4211 in the guide unit 4210 and the sizes and positions thereof may be determined to an extent that the efficiency of the cooling device 10000 is not significantly degraded. As a specific example, the guide unit 4210 of the cooling device 10000 may be formed such that the sum of the cross-sectional areas of the periphery holes 4211 is less than 100 mm$^2$.

Also, the number of periphery holes 4211 formed in the guide unit 4210 and the sizes and positions thereof may affect the extent to which the target region TR is cooled and may affect the phase of the coolant discharged to the outside via the periphery hole 4211 formed in the guide unit 4210. In a preferred embodiment, the periphery hole 4211 formed in the guide unit 4210 may have the size and position that allows 90% or more by volume of the coolant discharged to the outside through the periphery hole 4211 formed in the guide unit 4210 to be in a gas phase. Accordingly, it is possible to derive the effect of facilitating the discharge of the coolant through the hole. As a specific example, the guide unit 4210 of the cooling device 10000 may be formed such that the sum of the cross-sectional areas of the periphery holes 4211 is greater than 10 mm$^2$.

According to an embodiment of the present disclosure, the guide unit 4210 may perform a function of applying a pressure to a region related to the target region TR. The guide unit 4210 may perform a function of applying a pressure to at least a partial region of the target region TR. The guide unit 4210 may perform a function of applying a pressure to a boundary region of the target region TR.

According to an embodiment of the present application, the spraying unit 4000 may include a pressing portion 4300.

The pressing portion 4300 may perform a function of, when coming in contact with a surface of the target region TR, applying a pressure due to the contact to one region related to the target region TR. For example, the pressing portion 4300 may be configured to have a relatively protruding shape and may use such a shape to apply a pressure to one region related to the target region TR.

By applying a pressure to one region related to the target region TR, the pressing portion 4300 may perform a function of leaving a mark on the one region even after the pressing portion 4300 is separated and removed from the target region TR so that, when performing a subsequent injection after cooling by the cooling device 10000, the cooled region is able to be easily recognized.

The pressing portion 4300 may be one configuration included in the nozzle unit 4100 or the spraying site limiting unit. The pressing portion 4300 may be a separate configuration distinct from the nozzle unit 4100 and the spraying site limiting unit.

For example, the pressing portion 4300 may be one region of the guide unit 4210. The pressing portion 4300 may be one region of a contact portion of the guide unit 4210 that comes in contact with the target region TR. The pressing portion 4300 may be one relatively protruding region of a contact portion of the guide unit 4210 that comes in contact with the target region TR.

As another example, the pressing portion 4300 may be one region of a cooling tip. The pressing portion 4300 may be one region of a cooling tip of the cooling device 10000. The pressing portion 4300 may be one region of a contact portion of the cooling tip that comes in contact with the target region TR in a case in which the cooling tip is mounted on the cooling device 10000 and then cooling is performed by the cooling device 10000. The pressing portion 4300 may be one relatively protruding region of a contact portion of the cooling tip that comes in contact with the target region TR in a case in which the cooling tip is mounted on the cooling device 10000 and then cooling is performed by the cooling device 10000.

As still another example, the pressing portion 4300 may be one region of a housing of the cooling device 10000. The pressing portion 4300 may be one region of a contact portion of the housing that comes in contact with the target region TR in a case in which cooling is performed by the cooling device 10000. The pressing portion 4300 may be one relatively protruding region of a contact portion of the housing that comes in contact with the target region TR in a case in which cooling is performed by the cooling device 10000.

According to an embodiment of the present application, the spraying site limiting unit may further include a boundary heat providing unit configured to provide heat to a region other than the target region TR in order to limit a region where the coolant discharged from the nozzle unit 4100 reaches.

The boundary heat providing unit according to an embodiment of the present application may use convection to supply heat to the boundary of the target region TR and perform a function of discharging a heated fluid to a region other than the target region TR. The heated fluid may come into contact with a region other than the target region TR to provide heat to the region other than the target region TR.

The boundary heat providing unit according to an embodiment of the present application may use conduction to supply heat to the boundary of the target region TR and perform a function of causing a heating element to come into contact with a region other than the target region TR. The heating element may come into contact with a region other than the target region TR to provide heat to the region other than the target region TR.

The boundary heat providing unit according to an embodiment of the present application may use radiation to supply heat to the boundary of the target region TR and perform a function of providing radiant energy to a region other than the target region TR. The radiant energy may be provided to the region other than the target region TR to provide heat to the region other than the target region.

1.5 Control Unit 5000

The control unit 5000 according to an embodiment of the present application may perform a function of controlling operations of the elements of the cooling device 10000. The control unit 5000 may perform a function of controlling the coolant supply unit 1000, the flow regulating unit 2000, the coolant state regulating unit 3000, and/or the spraying unit 4000.

The control unit 5000 according to an embodiment of the present application may be implemented using a computer or a device similar thereto according to hardware, software, or a combination thereof. In terms of hardware, the control unit 5000 may be provided in the form of an electronic circuit such as a central processing unit (CPU) chip that processes an electrical signal to perform a control function. In terms of software, the control unit 5000 may be provided in the form of a program for driving the hardware of the control unit 5000.

The control unit 5000 according to an embodiment of the present application may control driving of the flow regulating unit 2000. As a more specific example, the control unit 5000 may control the opening and closing of the valve 2100 and control the opening and closing of the valve 2100 to have a repetitive cycle as necessary. A specific embodiment related thereto will be described in more detail below.

The control unit 5000 according to an embodiment of the present application may control driving of the coolant state regulating unit 3000. As a more specific example, the control unit 5000 may control whether a heating element is driven and control the on/off of the heating element in consideration of association with the opening and closing of the valve 2100 as necessary. A specific embodiment related thereto will be described in more detail below.

The control unit 5000 according to an embodiment of the present application may perform a function of controlling at least one of the coolant supply unit 1000, the flow regulating unit 2000, the coolant state regulating unit 3000, and/or the spraying unit 4000 on the basis of a detection signal of the sensor unit 6000 which will be described below.

As a more specific example, the control unit 5000 may control the opening and closing of the valve 2100 on the basis of a detection signal acquired from at least one of a temperature sensor 6100, a pressure sensor, an input sensor 6300, an identification sensor, and/or a gas sensor. A specific embodiment related thereto will be described in more detail below.

The control unit 5000 according to an embodiment of the present application may be implemented as a single control unit. The control unit 5000 according to another embodiment of the present application may be implemented as a plurality of control units.

Here, the cooling device 10000 including the control unit 5000 which includes a plurality of control units may be interpreted as the cooling device 10000 having a first control unit and a second control unit which operate independently. The first control unit may perform control related to at least a first function, and the second control unit may perform control related to at least a second function.

As a specific example, the first control unit may generally control a function of controlling the opening/closing of the valve 2100 when a cooling operation is performed by the cooling device 10000. The second control unit may control an operation for blocking a flow of a coolant to be performed when a temperature in at least one region of a flow path through which the coolant flows decreases to a predetermined temperature or lower when the cooling operation is performed by the cooling device 10000. Here, the second control unit may also block the flow of the coolant by performing an operation of closing the valve 2100. Since the second control unit which operates independently of the first control unit provides a means capable of preventing super-cooling, it is possible to provide the cooling device 10000 that ensures safety of a subject receiving treatment even when the first control unit of the cooling device 10000 malfunctions.

1.6 Sensor Unit

The sensor unit 6000 according to an embodiment of the present application may perform a function of detecting an environment associated with the cooling device 10000.

The sensor unit 6000 may include the temperature sensor 6100, the pressure sensor, the input sensor 6300, the identification sensor, and/or the gas sensor.

The temperature sensor 6100 may perform a function of measuring a temperature. For example, the temperature sensor 6100 may perform a function of measuring the temperature of the coolant sprayed through the nozzle unit 4100. As another example, the temperature sensor 6100 may perform a function of measuring the temperature of the cooling tip. As still another example, the temperature sensor 6100 may perform a function of measuring the temperature of the nozzle unit 4100. As yet another example, the temperature sensor 6100 may perform a function of measuring a temperature of outside air. As yet another example, the temperature sensor 6100 may perform a function of measuring the temperature of the reservoir 1100. As yet another example, the temperature sensor 6100 may perform a function of measuring the temperature of the target region TR.

The cooling device 10000 according to an embodiment of the present application may include one or more temperature sensors 6100.

For example, the cooling device 10000 may include a single temperature sensor 6100. As a specific example, the cooling device 10000 may include a first temperature sensor 6100 configured to measure the temperature of the target region TR.

As another example, the cooling device 10000 may include two or more temperature sensors 6100. As a specific example, the cooling device 10000 may include a first temperature sensor 6100 configured to measure the temperature of the nozzle unit 4100 or cooling tip and a second temperature sensor 6100 configured to measure the temperature of outside air.

The cooling device 10000 according to an embodiment of the present application may include a contact-type or non-contact-type temperature sensor 6100. For example, the temperature sensor 6100 may be an infrared (IR) thermometer.

However, some embodiments of the temperature sensor 6100 described above are merely specific examples intended to help in understanding, and the temperature sensor 6100 according to an embodiment of the present application may be provided in various other forms for various purposes.

The pressure sensor may perform a function of measuring pressure. For example, the pressure sensor may perform a function of measuring a pressure applied by the reservoir 1100. As another example, the pressure sensor may perform a function of measuring the pressure of the coolant stored in the reservoir 1100. As still another example, the pressure sensor may perform a function of measuring the pressure applied to the target region TR. As yet another example, the pressure sensor may perform a function of measuring the pressure inside at least one pipe disposed in the cooling device 10000.

The cooling device 10000 according to an embodiment of the present application may include one or more pressure sensors.

The cooling device 10000 according to an embodiment of the present application may include a pressure sensor between the reservoir 1100 and the reservoir receiving unit 1300, and the pressure sensor may measure the pressure applied by the reservoir 1100. On the basis of a signal detected from the pressure sensor, the control unit 5000 may calculate the pressure of the coolant stored in the reservoir 1100. Here, the pressure sensor may be a piezo sensor.

However, the embodiments of the pressure sensor described above is merely a specific example intended to help in understanding, and the pressure sensor according to an embodiment of the present application may be provided in various other forms for various purposes.

The input sensor 6300 may perform a function of detecting a user input. For example, the input sensor 6300 may perform a function of detecting an input for starting spraying of the coolant. As another example, the input sensor 6300 may perform a function of detecting an input for ending the spraying of the coolant. As still another example, the input sensor 6300 may perform a function of detecting an input for checking the state of the cooling device 10000.

The cooling device 10000 according to an embodiment of the present application may include one or more input sensors 6300. For example, the cooling device 10000 may include a single input sensor 6300. As a specific example, the input sensor 6300 may detect an input for starting spraying of the coolant and an input for ending the spraying of the coolant. The input for starting and the input for ending may be distinguished on the basis of a duration of a user input detected by the input sensor 6300. Alternatively, the input for starting and the input for ending may be distinguished on the basis of a time point of a user input detected by the input sensor 6300. As another example, the cooling device 10000 may include two or more input sensors 6300. As a specific example, a first input sensor 6300 may detect an input for starting spraying of the coolant, and a second input sensor 6300 may detect an input for ending the spraying of the coolant. Here, the second input sensor 6300 may be a button formed at a different position from the first input sensor 6300 so as to be used when there is an urgent need to end a cooling operation started on the basis of a signal detected through the first input sensor 6300.

The input sensor 6300 may be a physical button or may be implemented in the form of a gesture sensor, a touch sensor, a voice recognition sensor, or the like but is not limited thereto.

Also, some embodiments of the input sensor 6300 described above are merely specific examples intended to help in understanding, and the input sensor 6300 according to an embodiment of the present application may be provided in various other forms for various purposes.

The identification sensor may perform a function of detecting a user input. For example, the identification sensor may perform a function of identifying the cooling tip mounted on the cooling device 10000. As another example, the identification sensor may perform a function of identifying a user using the cooling device 10000. As still another example, the identification sensor may perform a function of identifying the reservoir 1100 accommodated in the reservoir receiving unit 1300.

The identification sensor may perform a function of checking whether an object to be identified is present. For example, the identification sensor may perform a function of checking whether the cooling tip is mounted on the cooling device 10000. The identification sensor may perform a function of distinguishing types of objects to be identified. For example, the identification sensor may perform a function of distinguishing types of cooling tips (e.g., sizes of cooling tips). As another example, the identification sensor may perform a function of distinguishing types of guide units 4210 (e.g., sizes of spraying regions limited by the guide unit 4210). As still another example, the identification sensor may perform a function of distinguishing types of reservoirs 1100 (e.g., sizes of CO$_2$ tanks). The identification sensor may perform a function of authenticating an object to be identified. For example, the identification sensor may perform a function of checking whether a user using the cooling device 10000 is an authenticated user.

The cooling device 10000 according to an embodiment of the present application may include one or more identification sensors.

The identification sensor may be a scanner that can recognize a quick response (QR) code or may be implemented in the form of a near-field communication (NFC) reader that can read an NFC tag, but is not limited thereto.

Also, some embodiments of the identification sensor described above are merely specific examples intended to help in understanding, and the identification sensor according to an embodiment of the present application may be provided in various other forms for various purposes.

The gas sensor may perform a function of detecting a gas concentration. For example, the gas sensor may perform a function of detecting a gas concentration in an environment in which the cooling device 10000 is used. As another example, the gas sensor may perform a function of detecting a gas concentration inside the cooling device 10000.

The gas sensor may perform a function of checking a concentration of gas that flows out due to use of the cooling device 10000. For example, the gas sensor may perform a gas detecting function to measure a CO$_2$ concentration in a case in which the cooling device 10000 uses CO$_2$ as the coolant. Here, the gas sensor may be a CO$_2$ sensor. Alternatively, the gas sensor may perform a function of detecting concentrations of multiple harmful gases. For example, the gas sensor may perform a function of detecting concentrations of N$_2$ and/or nitrogen oxide (NOx), CO$_2$, hydrogen (H$_2$) and/or hydrogen oxide (HO$_x$). Here, the gas sensor may be a harmful gas sensor.

The cooling device 10000 according to an embodiment of the present application may include one or more gas sensors.

However, some embodiments of the gas sensor described above are merely specific examples intended to help in understanding, and the gas sensor according to an embodiment of the present application may be provided in various other forms for various purposes.

The elements of the cooling device 10000 according to an embodiment of the present application have been described above. However, the cooling device 10000 according to the present application does not have to include only the above elements and may further include an output unit configured to output specific information to a user, a filter configured to filter impurities of a coolant flowing through the cooling device 10000, and the like.

Hereinafter, the connection relations between the elements of the cooling device 10000 according to an embodiment of the present application and the arrangement of the elements will be described in detail.

2. Structure of Cooling Device 10000

The cooling device 10000 according to an embodiment of the present application may be implemented in the form of being integrated with the reservoir 1100 so as to be provided as a portable device. Alternatively, the cooling device 10000 according to an embodiment of the present application may be implemented in the form of a handpiece having a part connected to an external tank so as to be used by being connected to the external tank.

The cooling device 10000 according to an embodiment of the present application may include at least one element of the above-described coolant supply unit 1000, flow regulating unit 2000, coolant state regulating unit 3000, spraying unit 4000, and control unit 5000.

For example, the cooling device 10000 may include the coolant supply unit 1000, the flow regulating unit 2000, the spraying unit 4000, and the control unit 5000. The cooling device 10000 according to an embodiment of the present application may form a flow path by the coolant supply unit 1000, the flow regulating unit 2000, and the spraying unit 4000 connected in that order, and the control unit 5000 may be implemented to control at least the flow regulating unit 2000.

As another example, the cooling device 10000 may include the coolant supply unit 1000, the flow regulating unit 2000, the coolant state regulating unit 3000, the spraying unit 4000, and the control unit 5000. The cooling device 10000 according to an embodiment of the present application may form a flow path by the coolant supply unit 1000, the flow regulating unit 2000, the coolant state regulating unit 3000, and the spraying unit 4000 connected in that order, and the control unit 5000 may be implemented to control at least the flow regulating unit 2000 and the coolant state regulating unit 3000.

The cooling device 10000 according to an embodiment of the present application may include at least one element of the above-described coolant supply unit 1000, flow regulating unit 2000, coolant state regulating unit 3000, spraying unit 4000, and control unit 5000 in a plurality. For example, the cooling device 10000 may include at least two valves 2100 as flow regulating units 2000. As another example, the cooling device 10000 may include at least two coolant cooling units 3200.

The cooling device 10000 according to an embodiment of the present application may include at least one element of the above-described coolant supply unit 1000, flow regulating unit 2000, coolant state regulating unit 3000, spraying unit 4000, and control unit 5000 in a plurality. Here, a plurality of a certain element may each perform a different function.

For example, the cooling device 10000 may include at least the coolant cooling unit 3200 and the spraying temperature regulating unit 3100 as coolant state regulating units 3000. The cooling device 10000 according to an embodiment of the present application may form a flow path by the coolant supply unit 1000, the coolant cooling unit 3200, the valve 2100, the spraying temperature regulating unit 3100, and the nozzle unit 4100 connected in that order, and the control unit 5000 may be implemented to control at least the valve 2100, the coolant cooling unit 3200, and the spraying temperature regulating unit 3100.

The cooling device 10000 according to an embodiment of the present application may be implemented as various forms of housings.

For example, the cooling device 10000 may have an elongated body (not illustrated). In a case in which the cooling device 10000 according to an embodiment of the present application has an elongated body, all of the elements of the cooling device 10000 may be disposed in the elongated body extending in a first direction. According to an embodiment of the present application, the elements of the cooling device 10000 disposed in the elongated body may be arranged in an order consistent with the direction of movement of a fluid.

Figure 2:
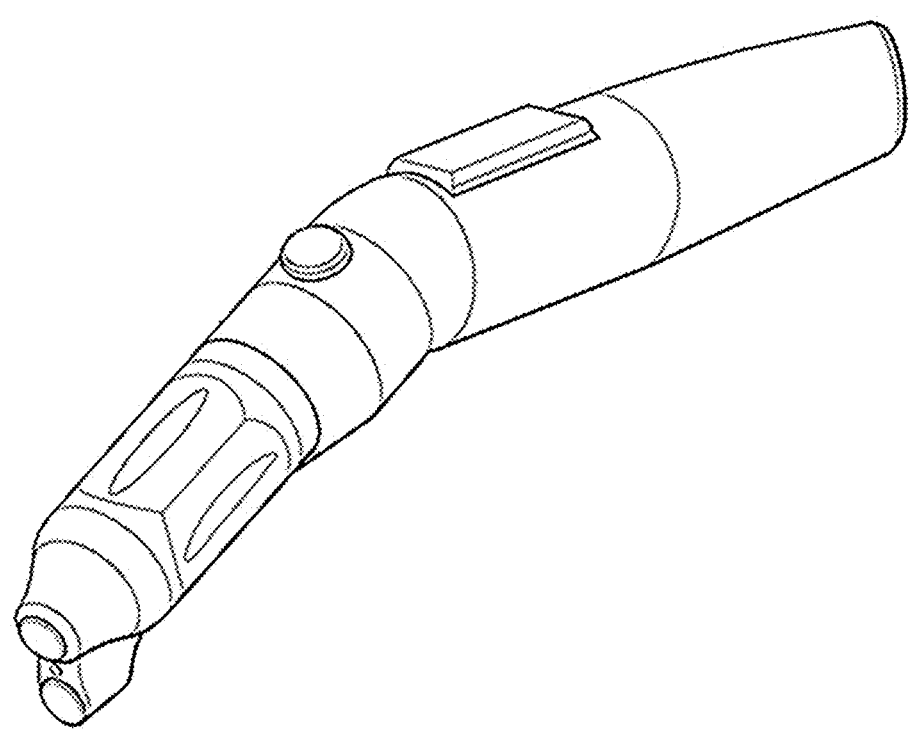
FIGS. 2 and 3 are diagrams for describing a structure of the cooling device 10000 according to an embodiment of the present application.

As another example, the cooling device 10000 may have a C-shaped body (see FIG. 2). In a case in which the cooling device 10000 according to an embodiment of the present application has a C-shaped body, all of the elements of the cooling device 10000 may be disposed in the C-shaped body. According to an embodiment of the present application, the elements of the cooling device 10000 disposed in the C-shaped body may be arranged in an order consistent with the direction of movement of a fluid.

Figure 3:
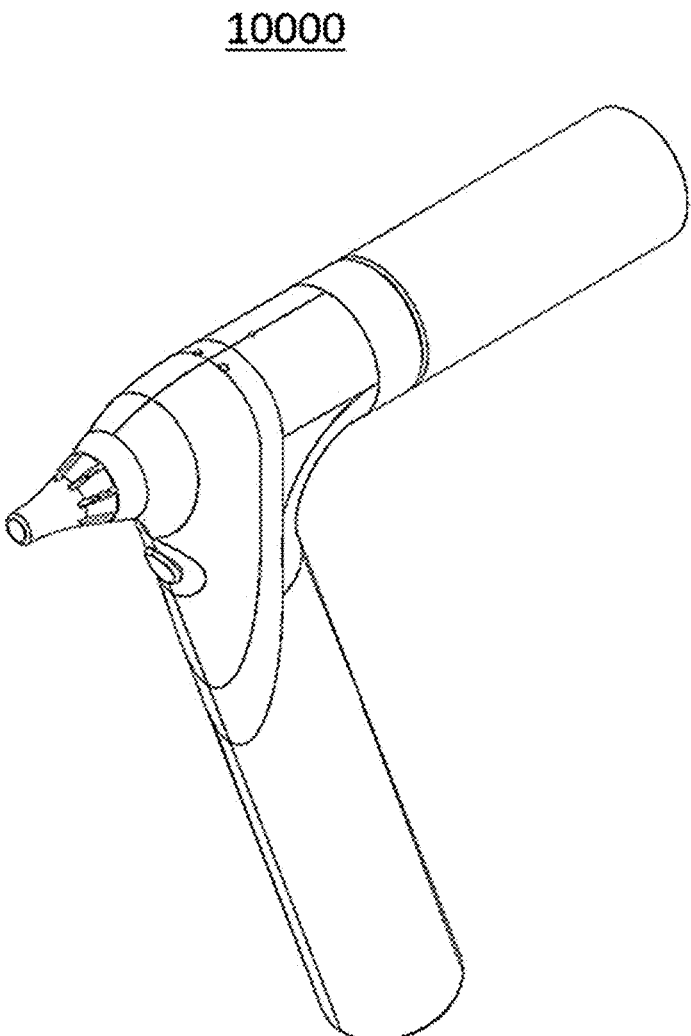

As still another example, the cooling device 10000 may have a T-shaped body (see FIG. 3). In a case in which the cooling device 10000 according to an embodiment of the present application has a T-shaped body, all of the elements of the cooling device 10000 may be disposed in a region of the T-shaped body extending in the first direction. Alternatively, in the case in which the cooling device 10000 according to an embodiment of the present application has a T-shaped body, some of the elements of the cooling device 10000 may be disposed in the region of the T-shaped body extending in the first direction, and the remaining elements may be disposed in a region of the T-shaped body extending in a second direction.

In addition, the cooling device 10000 may be formed in a pen shape, a pistol shape, a polygonal shape, or other shapes for ease of operation during use. Also, the cooling device 10000 may provide a gripping portion that may be gripped by a user. Also, the cooling device 10000 may be formed in a non-elongated structure. The non-elongated structure may include an open structure, a closed structure, a polygonal structure, and a curved structure.

The cooling device 10000 according to some embodiments of the present application has been described in detail above. However, the above-described embodiments only disclose specific embodiments intended to help in understanding of the present specification, and thus the scope of the present application should be determined on the basis of the claims below.

3. Basic Configuration of Cooling Device 10000 According to First Embodiment

Figure 4:
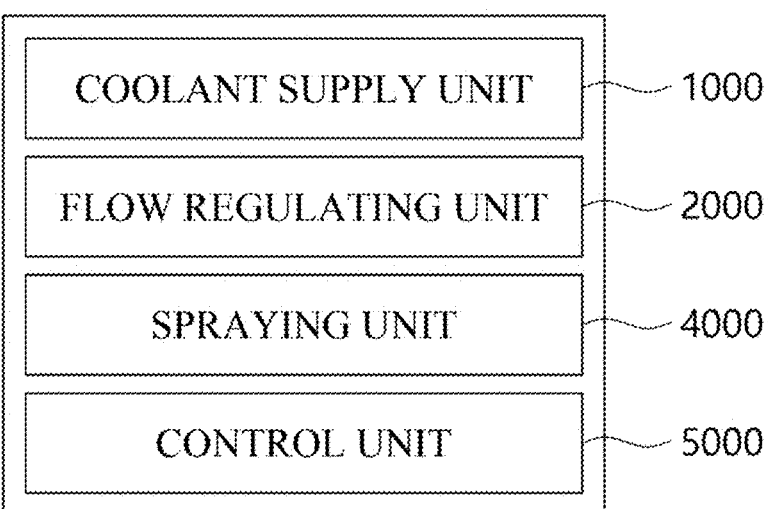
FIG. 4 is a diagram for describing a cooling device 10000 according to a first embodiment of the present application.

FIG. 4 is a diagram for describing a cooling device 10000 according to a first embodiment of the present application.

The cooling device 10000 according to the first embodiment of the present application may include the coolant supply unit 1000, the flow regulating unit 2000, the spraying unit 4000, and the control unit 5000.

As a more specific example, the cooling device 10000 according to the first embodiment of the present application may include the reservoir receiving unit 1300 as the coolant supply unit 1000. The cooling device 10000 according to the first embodiment of the present application may include the solenoid valve 2100 as the flow regulating unit 2000. The cooling device 10000 according to the first embodiment of the present application may include the nozzle unit 4100 as the spraying unit 4000. The cooling device 10000 according to the first embodiment of the present application may include a microcontroller unit (MCU) as the control unit 5000.

Figure 5:
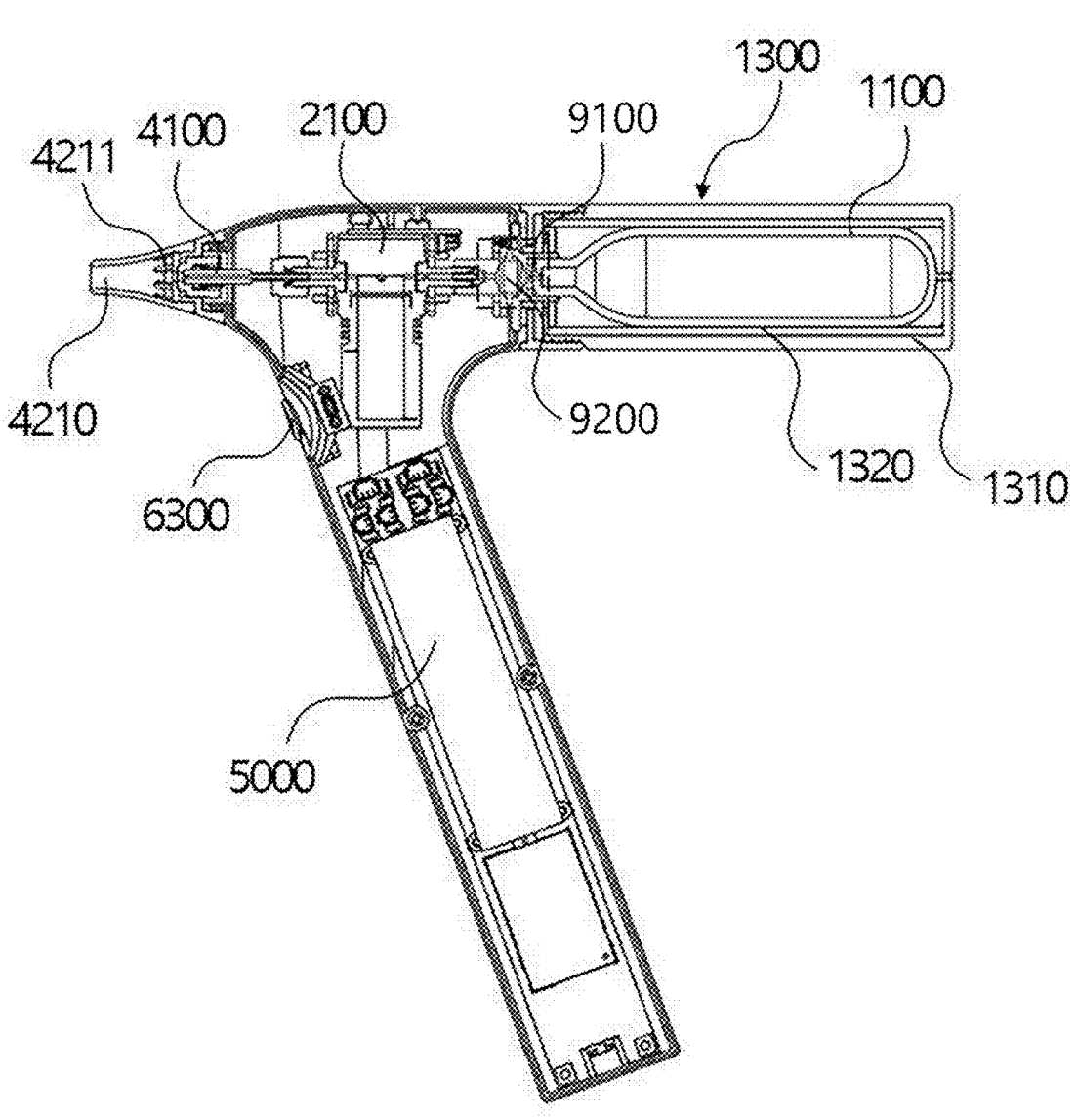
FIG. 5 is a diagram for describing a cross-section of the cooling device 10000 according to the first embodiment of the present application.

FIG. 5 is a diagram for describing a cross-section of the cooling device 10000 according to the first embodiment of the present application.

The cooling device 10000 may include the reservoir receiving unit 1300. The cooling device 10000 may include the reservoir 1100. As a specific example, the cooling device 10000 may include the reservoir receiving unit 1300 and the reservoir 1100 in a form in which the reservoir receiving unit 1300 is formed and the reservoir 1100 is mounted on the reservoir receiving unit 1300.

The reservoir receiving unit 1300 may include an receiving housing 1310 and a protective portion 1320. The receiving housing 1310 may be one element of the housing of the cooling device 10000. The receiving housing 1310 may be a region exposed to the outside of the cooling device 10000. The protective portion 1320 may be disposed at an inner side of the receiving housing 1310. The protective portion 1320 may be disposed between the receiving housing 1310 and the reservoir 1100. The protective portion 1320 may be disposed between the receiving housing 1310 and the reservoir 1100 when the reservoir 1100 is accommodated in the reservoir receiving unit 1300.

The receiving housing 1310 according to an embodiment of the present application may be made of a material having relatively low electrical conductivity or a material without electrical conductivity (e.g., nonconductor). The receiving housing 1310 may be made of a material having relatively low electrical conductivity or a material without electrical conductivity (e.g., nonconductor) for safety of a user of the cooling device 10000 and/or a patient. The receiving housing 1310 may be made of a material having relatively low electrical conductivity or a material without electrical conductivity (e.g., nonconductor) in order to prevent an electric shock that may occur when at least a portion of the cooling device 10000 comes in contact with a patient. The receiving housing 1310 may be made of a material having relatively low electrical conductivity or a material without electrical conductivity (e.g., nonconductor) in order to satisfy conditions of a withstand voltage test that is performed for commercial use of the cooling device 10000.

The protective portion 1320 according to an embodiment of the present application may be made of a material having high heat resistance. The protective portion 1320 according to an embodiment of the present application may be made of a material having high wear resistance. The protective portion 1320 according to an embodiment of the present application may be made of a material having high pressure resistance. The protective portion 1320 may have a characteristic in that at least one property of heat resistance, durability, and pressure resistance is relatively higher as compared to one element of the cooling device 10000. As a specific example, the protective portion 1320 may be made of a material having high heat resistance and/or pressure resistance in order to prevent explosion to the outside of the cooling device 10000 even when a fluid in the reservoir 1100 or a fluid flowing out from the reservoir 1100 is formed at a high temperature. As another specific example, the protective portion 1320 may be made of a material having high wear resistance in order to prevent wear or the like of the reservoir receiving unit 1300 in a process of mounting or removing the reservoir 1100 on or from the cooling device 10000.

The cooling device 10000 according to an embodiment of the present application may include an receiving housing 1310 made of a plastic material and a protective portion 1320 made of a metal material. The protective portion 1320 may be disposed inside the receiving housing 1310 to prevent damage to the receiving housing 1310 due to a phenomenon that may occur at a position where the reservoir 1100 is received. The receiving housing 1310 may be disposed outside the protective portion 1320 to prevent a user or patient from getting an electric shock via the receiving housing 1310 even when the receiving housing 1310 acts as a charged body to the protective portion 1320.

The reservoir 1100 may be a cartridge containing a coolant. As a specific example, the reservoir 1100 may be a cartridge containing $CO_2$.

The reservoir 1100 according to an embodiment of the present application may include a region coming in contact with the protective portion 1320 when the reservoir 1100 is mounted on the reservoir receiving unit 1300. The reservoir 1100 according to another embodiment of the present application may be spaced apart from the protective portion 1320 so that the reservoir 1100 does not have a region coming in contact with the protective portion 1320 when the reservoir 1100 is mounted on the reservoir receiving unit 1300.

The cooling device 10000 may include the solenoid valve 2100. The solenoid valve 2100 may perform discharge of a fluid and blockage of the fluid discharge in response to an electrical signal. As a more specific example, the solenoid valve 2100 may include an inlet into which the fluid flows, an outlet from which the fluid flows out, a plunger configured to reciprocate to block a flow of the fluid, and an armature configured to generate an induced magnetic force.

The cooling device 10000 may include the nozzle unit 4100. The nozzle unit 4100 may be provided in the form in which a cross-sectional area of a first end is different from a cross-sectional area of a second end. The nozzle unit 4100 may be provided in the form in which a cross-sectional area of a first end which is relatively more spaced apart from the cartridge is smaller than a cross-sectional area of a second end. Here, since resistance applied to the fluid flow increases due to a decrease in the cross-sectional area of the first end, the nozzle unit 4100 may perform a function of allowing a constant amount of coolant to be jetted to the outside of the cooling device 10000.

The cooling device 10000 may include the control unit 5000 (e.g., MCU). The control unit 5000 may generate a control signal for controlling the on/off and/or the opening/closing amount of the solenoid valve 2100 and transmit the generated control signal to the solenoid valve 2100.

The cooling device 10000 may include at least one pipe. The pipe may be used in forming a flow path to jet the coolant discharged from the reservoir 1100 in the cooling device 10000 to the outside through the nozzle unit 4100.

According to an embodiment of the present application, the cooling device 10000 may include a pipe that involves in forming a flow path between a coolant discharge port of the reservoir 1100 and the inlet of the solenoid valve 2100. At least one pipe may be disposed between the coolant discharge port of the reservoir 1100 and the inlet of the solenoid valve 2100.

In a case in which a plurality of pipes are disposed between the coolant discharge port of the reservoir 1100 and the inlet of the solenoid valve 2100 according to an embodiment of the present application, a first pipe and a second pipe may be connected in a form that does not cause much outflow of coolant and form a flow path. As a specific example, the first pipe and the second pipe may be connected in the form of being fitted and coupled.

According to an embodiment of the present application, the cooling device 10000 may include a pipe that involves in forming a flow path between the outlet of the solenoid valve 2100 and a coolant discharge port of the nozzle unit 4100.

In a case in which a plurality of pipes are disposed between the outlet of the solenoid valve 2100 and the coolant discharge port of the nozzle unit 4100 according to an embodiment of the present application, a third pipe and a fourth pipe may be connected in a form that does not cause much outflow of coolant and form a flow path. As a specific example, the third pipe and the fourth pipe may be connected in the form of being fitted and coupled.

A perforation structure 9100 for perforating the reservoir 1100 may be formed in the cooling device 10000. In a case in which the cooling device 10000 includes the reservoir 1100, the reservoir 1100 is provided in a replaceable form in some cases. In this case, when the reservoir 1100 is mounted on the cooling device 10000, the cooling device 10000 has to perform an operation of perforating to allow outflow of a fluid stored in the reservoir 1100. Thus, the perforation structure 9100 for perforating the reservoir 1100 may be formed in the cooling device 10000.

According to an embodiment of the present application, the cooling device 10000 may include, as the perforation structure 9100, a region in which an outer diameter of one end of the flow path gradually decreases. A region in which the outer diameter of the one end of the flow path is the smallest may be formed at a position more adjacent to the reservoir 1100 than a region in which the outer diameter of the one end of the flow path is the largest.

As a specific example, the perforation structure 9100 may have a structure in which an outer diameter gradually decreases. The structure in which the outer diameter gradually decreases may form an inclined surface at an outer surface of the perforation structure 9100. The inclined outer surface of the perforation structure 9100 may directly come in close contact with a perforated portion of the reservoir 1100. Since the inclined outer surface of the perforation structure 9100 comes in close contact with the perforated portion of the reservoir 1100, even without a separate O-ring, it is possible to prevent outflow of the coolant stored in the reservoir 1100 to the outside. In a case in which the perforation structure 9100 directly forms a sealing with the reservoir 1100, even when the reservoir 1100 is separated from the perforation structure 9100, it is possible to derive an effect of allowing the coolant remaining in the reservoir 1100 to smoothly come out.

The perforation structure 9100 may be made of a material with a relatively high stiffness. The perforation structure 9100 may be made of a material with a relatively high wear resistance. An outer side of the perforation structure 9100 may be made of a material with a relatively higher stiffness or wear resistance as compared to the reservoir 1100.

The perforation structure 9100 may have a form in which it is coated with a material having a relatively high stiffness or wear resistance. The perforation structure 9100 may have a form in which an inner side of the perforation structure 9100 is made of the same material as the pipe of the cooling device 10000 and the outer side of the perforation structure 9100 is coated with a material having a high stiffness.

According to an embodiment of the present application, a passage through which a coolant may flow may be formed in one region of the perforation structure 9100. The perforation structure 9100 may have a specific shape in one region of the pipe to form a region where outflow of coolant is possible in the reservoir 1100 when the reservoir 1100 is accommodated in the reservoir receiving unit 1300. In this way, the cooling device 10000 may include the perforation structure 9100 that allows the coolant to flow from the region where the outflow of coolant is possible in the reservoir 1100 toward the inlet of the valve 2100 via the passage formed inside the perforation structure 9100.

Figure 6:
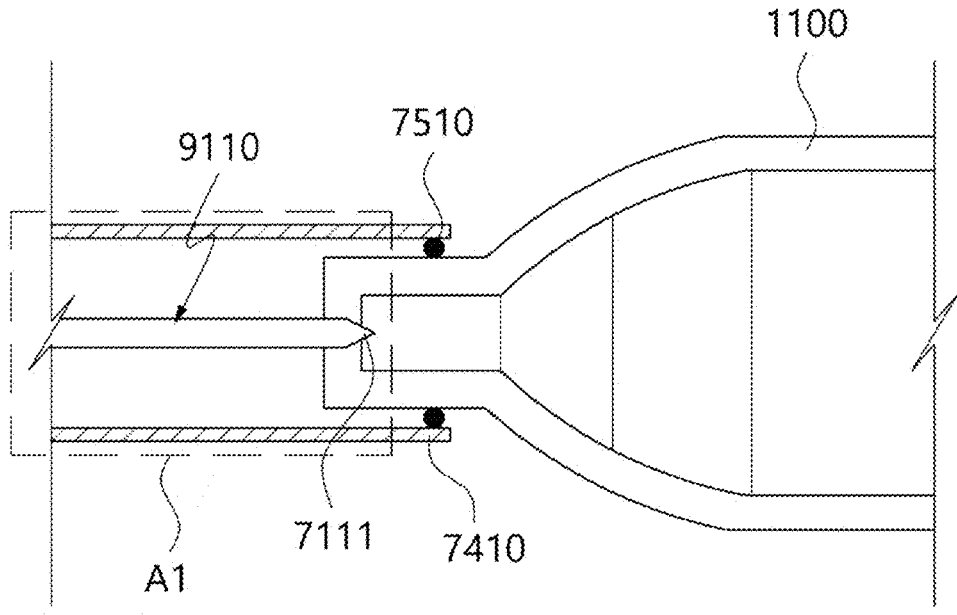
FIG. 6 is a diagram for describing a perforation structure 9100 according to another embodiment of the present application.

FIG. 6 is a view for describing a perforation structure 9100 according to another embodiment of the present application.

Referring to FIG. 6, the cooling device 10000 may include a pipe 7410 configured to provide a passage for a fluid flowing between the valve 2100 and the reservoir 1100 and a fin 9110 used in perforating at least one region of the reservoir 1100.

The fin 9110 may be disposed inside the pipe 7410. The fin 9110 may be disposed in a space of the pipe 7410 where a coolant flows. The fin 9110 may be disposed to come in contact with one region of the reservoir 1100 when the reservoir 1100 is accommodated in the reservoir receiving unit 1300.

The fin 9110 may include, as the perforation structure 9100, a region 7111 in which an outer diameter gradually decreases. The fin 9110 may be disposed inside the pipe 7410 so that a region with the smallest outer diameter is the most adjacent to the reservoir 1100.

The fin 9110 may be made of a material with a relatively high stiffness. The fin 9110 may be made of a material with a relatively high wear resistance. An outer side of the fin 9110 may be made of a material with a relatively higher stiffness or wear resistance as compared to the reservoir 1100. The fin 9110 may have a form in which it is coated with a material having a relatively high stiffness or wear resistance. As a specific example, the fin 9110 may have a form in which an inner side of the fin 9110 is made of the same material as the pipe of the cooling device 10000 and an outer side of the fin 9110 is coated with a material having a high stiffness.

According to an embodiment of the present application, at least a portion of the reservoir 1100 may enter the pipe 7410. The pipe 7410 may be disposed so that at least a portion of the reservoir 1100 enters the pipe 7410. The pipe 7410 may be disposed so that at least a portion of the reservoir 1100 enters the pipe 7410 when the reservoir 1100 is mounted. At least a portion of the reservoir 1100 may enter the space of the pipe 7410 where the coolant flows.

According to an embodiment of the present application, when the reservoir 1100 has entered the pipe 7410, a sealing member 7510 may be disposed between the reservoir 1100 and the pipe 7410. As a specific example, an O-ring-shaped sealing member 7510 may be disposed inside the pipe 7410, and in a case in which the reservoir 1100 is inserted into the pipe 7410 and the reservoir 1100 is perforated, the coolant flowing out from the reservoir 1100 may flow into the pipe 7410. Here, the sealing member 7510 may minimize outflow of the coolant to the outside of the pipe 7410.

An embodiment of the present application may provide the cooling device 10000 that cools a target region using a coolant, the cooling device 10000 including the coolant supply unit 1000 configured to supply the coolant, the spraying unit 4000 configured to spray the coolant, and the valve 2100 disposed between the coolant supply unit 1000 and the spraying unit 4000. A first region A1 in which a movement speed of the coolant is controlled may be included between the valve 2100 and the coolant supply unit 1000. The first region A1 may be a region in which the fin 9110 is disposed inside the pipe 7410 formed between the valve 2100 and the coolant supply unit 1000. An outer diameter of the pipe 7410 where the fin 9110 is not disposed and an outer diameter of the pipe 7410 where the fin 9110 is disposed may be the same, and a cross-sectional area of a region in which a fluid is movable in the pipe 7410 where the fin 9110 is not disposed may be larger than a cross-sectional area of a region in which a fluid is movable in the pipe 7410 where the fin 9110 is disposed.

Since the cross-sectional area of the region in which a fluid is movable in the pipe 7410 where the fin 9110 is not disposed is different from the cross-sectional area of the region in which a fluid is movable in the pipe 7410 where the fin 9110 is disposed, the first region A1 may serve as a section in which a movement speed of a fluid is changed.

Referring back to FIG. 5, the coolant flowing out from the reservoir 1100 may flow into the inlet of the valve 2100.

According to an embodiment of the present application, the cooling device 10000 may further include a limited-capacity coolant reservoir 9200 capable of accommodating a coolant by a specific volume. The limited-capacity coolant reservoir 9200 may accommodate a predetermined amount of coolant.

The limited-capacity coolant reservoir 9200 may be disposed between the solenoid valve 2100 and the reservoir 1100. An inflow port of the limited-capacity coolant reservoir 9200 may be connected to the reservoir 1100 to allow a fluid to move. An outflow port of the limited-capacity coolant reservoir 9200 may be connected to the solenoid valve 2100 to allow the fluid to move.

According to an embodiment of the present application, a first pipe connected to the inflow port of the limited-capacity coolant reservoir 9200 may have a relatively smaller cross-sectional area as compared to a second pipe connected to the outflow port of the limited-capacity coolant reservoir 9200. The resistance loaded to the flow of the coolant in the first pipe may be higher than the resistance loaded to the flow of the coolant in the second pipe. That is, a pressure drop of the coolant in the first pipe may be greater than a pressure drop of the coolant in the second pipe. Here, a temperature drop of the coolant in the first pipe may be greater than a temperature drop of the coolant in the second pipe.

According to another embodiment of the present application, the first pipe connected to the inflow port of the limited-capacity coolant reservoir 9200 may have substantially the same cross-sectional area as the second pipe connected to the outflow port of the limited-capacity coolant reservoir 9200. The flow of the coolant in the first pipe may be substantially the same as the flow of the coolant in the second pipe. The pressure of the coolant in the first pipe may be substantially the same as the pressure of the coolant in the second pipe.

Figure 7:
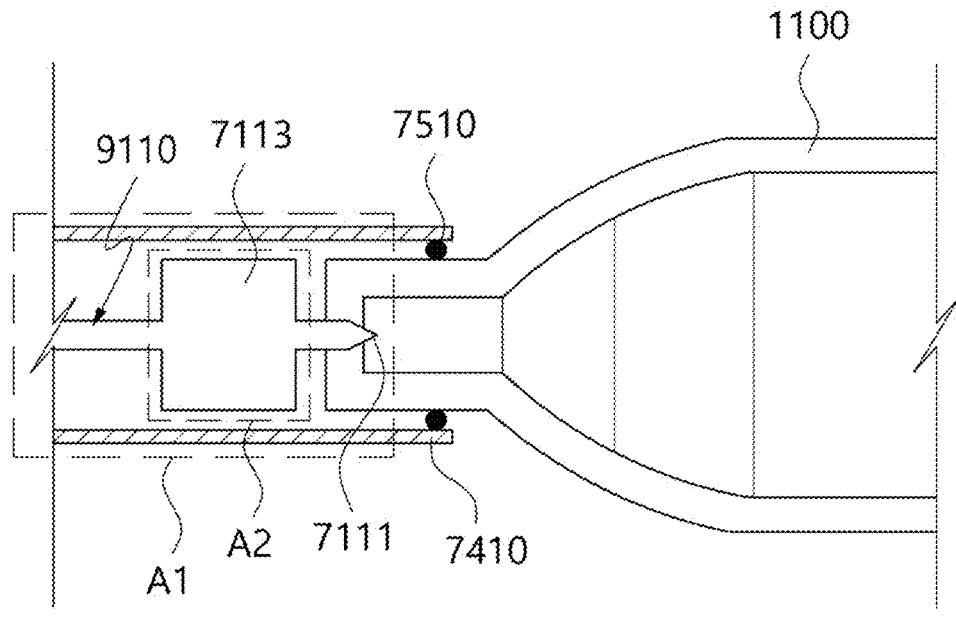
FIG. 7 is a diagram for describing the perforation structure 9100 and a limited-capacity coolant reservoir 9200 according to another embodiment of the present application.

FIG. 7 is a view for describing a perforation structure 9100 and a limited-capacity coolant reservoir 9200 according to another embodiment of the present application.

Referring to FIG. 7, the cooling device 10000 may include a pipe 7410 configured to provide a passage to a fluid flowing between the valve 2100 and the reservoir 1100 and a fin 9110 used in perforating at least one region of the reservoir 1100.

As described above with reference to FIG. 6, the fin 9110 may be disposed inside the pipe 7410. The fin 9110 may include, as the perforation structure 9100, a region 7111 in which an outer diameter gradually decreases. The fin 9110 may be made of a material with a relatively high stiffness. The pipe 7410 may be disposed so that the reservoir 1100 enters the pipe 7410. When the reservoir 1100 has entered the pipe 7410, a sealing member 7510 may be disposed between the reservoir 1100 and the pipe 7410.

Since this has already been described in detail above in describing the cooling device 10000 according to FIG. 6, description thereof will be omitted to avoid redundant description.

The fin 9110 according to an embodiment of the present application may include a region 7113 having a relatively large outer diameter. The fin 9110 may include, as the perforation structure 9100, the region 7111 in which the outer diameter gradually decreases and may include, as a flow restriction unit, the region 7113 having a relatively large outer diameter.

According to an embodiment of the present application, the cooling device 10000 that cools a target region using a coolant may include the coolant supply unit 1000 configured to supply the coolant, the spraying unit 4000 configured to spray the coolant, and the valve 2100 disposed between the coolant supply unit 1000 and the spraying unit 4000. A second region A2 in which a movement speed of the coolant is controlled may be included between the valve 2100 and the coolant supply unit 1000. The second region A2 may be a region in which a fin with a relatively large outer diameter is disposed in the first region A1 disposed between the valve 2100 and the coolant supply unit 1000. The cooling device 10000 may be provided so that an outer diameter of the pipe 7410 in the first region A1 and an outer diameter of the pipe 7410 in the second region A2 are the same, and a cross-sectional area of a region in which a fluid is movable in the pipe 7410 of the first region A1 is larger than a cross-sectional area of a region in which a fluid is movable in the pipe 7410 of the second region A2.

The second region A2 may serve as a section in which a movement speed of a fluid is changed.

The cooling device 10000 according to an embodiment of the present application may further include a filter configured to filter impurities of a coolant flowing in the cooling device 10000. The filter may be installed in at least one region of the flow path through which the coolant flows in the cooling device 10000. The filter may have a form corresponding to the cross-sectional shape of the pipe. The filter may be made of a porous material. The filter may be made of a metal mesh. The filter may be made of a material made of paper or fiber. The filter may be made of a hydrophobic material.

As a specific example, the filter may be disposed in the limited-capacity coolant reservoir 9200. The cooling device 10000 may further include an input sensor 6300. The input sensor 6300 may acquire a signal corresponding to a user input. The input sensor 6300 may be implemented using a keyboard, a keypad, a button, a jog/shuttle, a wheel, and the like. The input sensor 6300 may be a key pad utilized as a switch.

The cooling device 10000 may include a switch configured to generate an electrical signal in response to user contact. The switch may perform a function of generating an electrical signal in response to generation of an electrical or electrostatic signal according to user contact. Alternatively, the switch may perform a function of generating an electrical signal in response to generation of a pressure of a predetermined numerical value or higher according to user contact.

The cooling device 10000 may further include a temperature sensor 6100 (not illustrated). As a specific example, the temperature sensor 6100 may be a contact-type temperature sensor configured to measure temperature outside the pipe disposed between the nozzle unit 4100 and the valve 2100.

The cooling device 10000 may include a guide unit 4210. As a specific example, the guide unit 4210 may be mounted on the cooling device 10000 in order to limit the spraying range of the coolant sprayed through the nozzle unit 4100. The guide unit 4210 may be disposed on a movement path of the coolant sprayed from the nozzle unit 4100.

The cooling device 10000 may further include a power source unit. The cooling device 10000 may further include a power source unit configured to supply power for driving the cooling device 10000. The power source unit may include at least one of a direct-current power source for supplying direct current and an alternating-current power source for supplying alternating current. For example, the power source unit may be a secondary battery.

The power source unit may supply power to the control unit 5000. The power source unit may supply power to the solenoid valve 2100. The power source unit may supply power for controlling the opening and closing of the solenoid valve 2100.

The cooling device 10000 according to the first embodiment of the present application has been disclosed above. However, the above description only discloses one specific embodiment intended to help in understanding, and thus the form of the cooling device 10000 disclosed by the present application is not limited to the cooling device 10000 according to the first embodiment that has been described above, and the scope of the present application should be determined on the basis of the claims below.

4. Basic Configuration of Cooling Device 10000 According to Second Embodiment FIG. 8 is a view for describing a cooling system 1 including a cooling device 10000 according to a second embodiment of the present application.

The cooling device 10000 according to the second embodiment of the present application may include the coolant supply unit 1000, the flow regulating unit 2000, the coolant state regulating unit 3000, the spraying unit 4000, and the control unit 5000.

The cooling device 10000 according to the second embodiment of the present application may include the transfer unit 1200, the solenoid valve 2100, the coolant cooling unit 3200, the spraying temperature regulating unit 3100, the nozzle unit 4100, and the control unit 5000.

Figure 9:
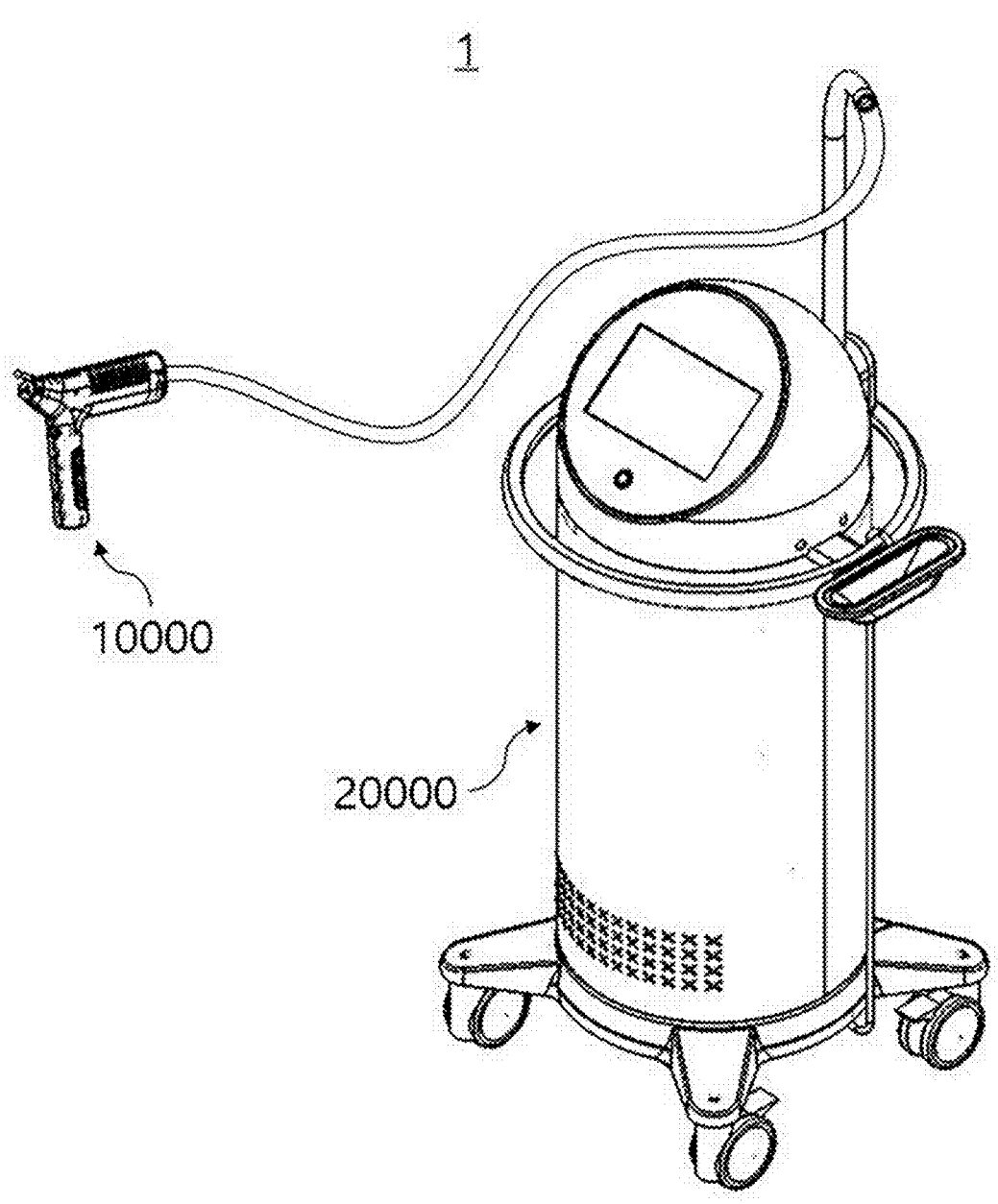
FIG. 9 illustrates the cooling system 1 according to an embodiment of the present application.

FIG. 9 illustrates the cooling system 1 according to an embodiment of the present application.

The cooling system 1 according to an embodiment of the present application may include the cooling device 10000, a hose connected to the cooling device 10000, and a coolant storage tank.

According to an embodiment of the present application, the coolant storage tank may be in the form of being kept inside a main body 20000. According to an embodiment of the present application, the main body 20000 may be connected to a wheel for convenience of movement. According to an embodiment of the present application, the main body 20000 may include a display panel for informing a user of a state of the cooling system 1. According to an embodiment of the present application, the main body 20000 may include a mounting region on which the cooling device 10000 may be mounted. However, these are merely examples relating to the main body 20000 according to an embodiment of the present application, and of course, the main body 20000 may be implemented in a form in which some elements are omitted, added, or overlap.

Figure 10:
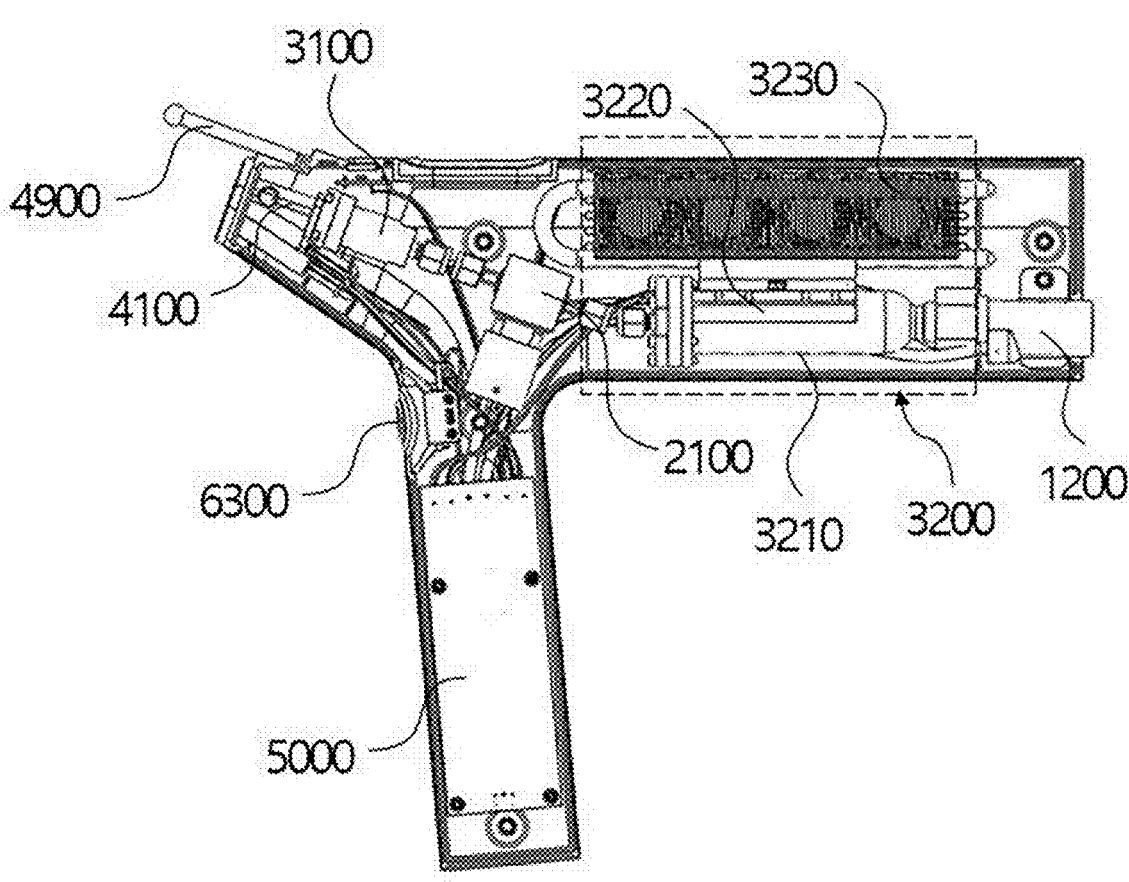
FIG. 10 is a diagram for describing a cross-section of the cooling device 10000 according to the second embodiment of the present application.

FIG. 10 is a cross-sectional view of the cooling device 10000 according to the second embodiment of the present application.

The cooling device 10000 may include the transfer unit 1200. The transfer unit 1200 may be an inflow port configured to receive the coolant from the tank. As a specific example, the transfer unit 1200 may receive $CO_2$ from the coolant storage tank accommodating $CO_2$ and transfer the received $CO_2$ to one element of the cooling device 10000.

The cooling device 10000 may include the coolant cooling unit 3200. The coolant cooling unit 3200 may change a state of the coolant that passed through the transfer unit 1200. The coolant cooling unit 3200 may perform a function of cooling the coolant that passed through the transfer unit 1200.

The cooling device 10000 may include the solenoid valve 2100. The solenoid valve 2100 may perform discharge of a fluid and blockage of the discharge of the fluid in response to an electrical signal. As a more specific example, the solenoid valve 2100 may include an inlet into which the fluid flows, an outlet from which the fluid flows out, a plunger configured to reciprocate to block a flow of the fluid, and an armature configured to generate an induced magnetic force.

In response to an electrical signal applied thereto, the solenoid valve 2100 may generate an electromagnetic force at the armature and change the plunger to an open state. The solenoid valve 2100 may eliminate the electromagnetic force generated at the armature and change the plunger to a closed state.

According to an embodiment of the present application, the coolant cooling unit 3200 may perform a function of cooling the coolant that passed through the transfer unit 1200.

The coolant cooling unit 3200 may include a reservoir 3210 configured to accommodate the coolant, a cooling element 3220 configured to cool the reservoir 3210, and a heat dissipater 3230 configured to dissipate heat generated in the cooling element.

The coolant flowing into the transfer unit 1200 may pass through the transfer unit 1200 and flow into the reservoir 3210. The coolant accommodated in the reservoir 3210 may be cooled using the cooling element 3220 disposed to allow a heat exchange with the reservoir 3210.

According to an embodiment of the present application, according to a cooling operation of the cooling element 3220, the proportion of liquid in the coolant accommodated in the reservoir 3210 may increase. In other words, as compared to the proportion of liquid/gas in the coolant when the coolant flows into the reservoir 3210, the proportion of liquid/gas in the coolant when the coolant is accommodated in the reservoir 3210 and cooled by the cooling element 3220 may be greater.

In a case in which the cooling element 3220 is a thermo-electric element, as an endothermic reaction is performed at one side of the cooling element 3220 that is at the reservoir 3210 side, an exothermic reaction may be performed at the other side of the cooling element 3220 that is opposite to the reservoir 3210 side. Therefore, the heat dissipater 3230 configured to dissipate heat according to the exothermic reaction may be disposed at the side opposite to the reservoir 3210 side.

The heat dissipater 3230 may perform a function of dissipating heat generated in a partial region of the cooling element 3220 to the outside. The heat dissipater 3230 may include a structure for emitting heat. As a specific example, the heat dissipater 3230 may include a radial structure. The heat dissipater 3230 may include a structure for circulating air. As a specific example, the heat dissipater 3230 may include a ventilator.

The heat dissipater 3230 according to an embodiment of the present application may include the radial structure and a ventilator that allows outside air to circulate in the radial structure.

Figure 11:
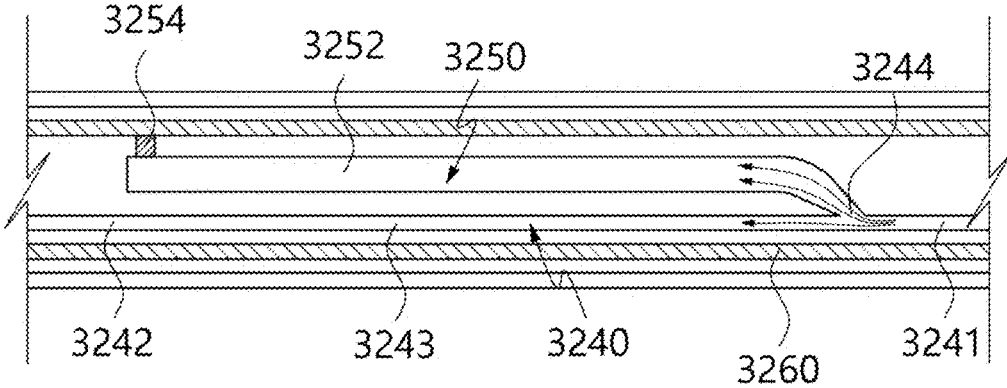
FIG. 11 is a diagram for describing a coolant cooling unit 3200 according to another embodiment of the present application.

FIG. 11 is a diagram for describing a coolant cooling unit 3200 according to another embodiment of the present application.

The coolant cooling unit 3200 according to another embodiment of the present application has a structure in which the coolant stored in the reservoir 1100 is utilized to cool the coolant that passed through the transfer unit 1200. In the case of the cooling device 10000 to which the coolant cooling unit 3200 according to another embodiment of the present application is applied, an energy saving effect may be derived due to a decrease in the total amount of power necessary for performing a cooling operation, and an effect of reducing the size of the cooling device 10000 may be induced because a space for implementing the heat dissipater 3230 or the like may be omitted.

The coolant cooling unit 3200 according to another embodiment of the present application may include a coolant movement passage 3240 and a coolant cooling passage 3250.

The coolant movement passage 3240 may perform a function of receiving the coolant from the transfer unit 1200 and providing an intermediate path to allow the coolant to be discharged to the target region TR. The coolant that passed through the coolant movement passage 3240 may be transferred to the target region TR.

According to an embodiment of the present application, the coolant movement passage 3240 may include at least a transfer unit connection inlet 3241 for receiving the coolant from the transfer unit 1200, a valve connection outlet 3242 for allowing the coolant flowing into the transfer unit connection inlet 3241 to flow out to the valve 2100, and a connection pipe 3243 disposed between the transfer unit connection inlet 3241 and the valve connection outlet 3242 to connect the two so that a fluid may move.

An outflow groove 3244 for allowing a portion of the coolant flowing into the coolant movement passage 3240 to flow into the coolant cooling passage 3250 may be formed in the coolant cooling unit 3200 according to an embodiment of the present application. For example, the outflow groove 3244 may be formed in at least one position of the coolant movement passage 3240. According to an embodiment of the present application, the outflow groove 3244 may be disposed closer to the transfer unit connection inlet 3241 than the valve 2100.

In still another embodiment, the coolant supplied to the coolant cooling passage 3250 may be supplied from a second coolant supply unit 1000, which is independent of the coolant supply unit 1000 storing the coolant to be supplied to the coolant movement passage 3240, instead of flowing in through the outflow groove 3244 after flowing into the transfer unit connection inlet 3241

The coolant may flow into the coolant cooling passage 3250 through the outflow groove 3244.

The coolant cooling passage 3250 according to an embodiment of the present application may include at least a discharge pipe 3252 in which the coolant flowing in from the outflow groove 3244 expands and a control valve 3254 configured to control a coolant flow so that the coolant inside the discharge pipe 3252 flows out of the discharge pipe 3252 under the predetermined condition. The control valve 3254 may be present between the outflow groove 3244 and an end of the coolant cooling passage 3250 from which the coolant is sprayed.

In the discharge pipe 3252, the coolant may perform cooling through expansion. In other words, a pressure of the coolant before the coolant passes through the outflow groove 3244 and a pressure of the coolant after the coolant passes through the outflow groove 3244 may be different. The pressure of the coolant before the coolant passes through the outflow groove 3244 may be higher than the pressure of the coolant after the coolant passes through the outflow groove 3244. Therefore, the coolant may perform cooling by expansion in the discharge pipe 3252 after passing through the outflow groove 3244.

According to an embodiment of the present application, a cross-sectional area of the discharge pipe 3252 may be larger than a cross-sectional area of the connection pipe 3243 so that the coolant expands.

The control valve 3254 may control a coolant flow so that the coolant inside the discharge pipe 3252 flows out of the discharge pipe 3252 under the predetermined condition. For example, the control valve 3254 may include a control valve 3254 configured to control a coolant flow so that, when the pressure in the discharge pipe 3252 increases to a predetermined numerical value or more, the coolant inside the discharge pipe 3252 flows out of the discharge pipe 3252. As another example, the control valve 3254 may include a control valve 3254 configured to control a coolant flow so that, when the temperature in the discharge pipe 3252 increases to a predetermined numerical value or more, the coolant inside the discharge pipe 3252 flows out of the discharge pipe 3252.

The control valve 3254 may be connected to a separate pressure sensor configured to measure the pressure inside the discharge pipe 3252. Alternatively, the control valve 3254 may have a form combined with the pressure sensor configured to measure the pressure inside the discharge pipe 3252. Likewise, the control valve 3254 may be connected to a separate temperature sensor configured to measure the temperature inside the discharge pipe 3252. Alternatively, the control valve 3254 may have a form combined with the temperature sensor configured to measure the temperature inside the discharge pipe 3252.

The control valve 3254 may be electrically connected to the control unit 5000 configured to control an outflow of a coolant or blockage of the outflow of the coolant on the basis of the confirmed pressure or temperature in the discharge pipe 3252. As a specific example, the cooling device 10000 may include the control unit 5000, and the control unit 5000 may control the valve 2100 and the control valve 3254. As another specific example, the cooling device 10000 may include a plurality of control units 5000, and one control unit 5000 may control the valve 2100 while another control unit 5000 controls the control valve 3254.

The coolant movement passage 3240 may be disposed to allow a heat exchange with the coolant cooling passage 3250. The coolant cooling passage 3250 including the discharge pipe 3252 may be disposed to allow a heat exchange with the coolant movement passage 3240 including the connection pipe 3243.

According to an embodiment of the present application, the cooling device 10000 may further include an adiabatic passage 3260 to prevent a region in which a heat exchange occurs between the coolant movement passage 3240 and the coolant cooling passage 3250 from being heated by outside air. As a specific example, the coolant movement passage 3240 and the coolant cooling passage 3250 may be disposed adjacent to each other in a single sealed space due to the adiabatic passage 3260, and the coolant movement passage 3240 and/or the coolant cooling passage 3250 may be prevented from being heated by outside air.

In the adiabatic passage 3260, the discharge pipe 3252 may be disposed more adjacent to the valve connection outlet 3242 than to the transfer unit connection inlet 3241 disposed at an end of the coolant movement passage 3240. Specifically, a position in the discharge pipe 3252 where the coolant is sprayed to the outside may be within 300 mm from an inlet portion of the valve 2100 controlling spraying of the coolant moving in the coolant movement passage 3240.

For example, the coolant cooling passage 3250 may perform a function of lowering the temperature of the coolant flowing in the coolant movement passage 3240. Here, the coolant cooling passage 3250 may perform a function of increasing the proportion of liquid with respect to gas in the coolant flowing in the coolant movement passage 3240. As a specific example, the coolant expanded in the discharge pipe 3252 may have a lower temperature than at least the coolant passing through the connection pipe 3243 and may, through a heat exchange between the coolant cooling passage 3250 and the coolant movement passage 3240, perform a function of increasing the proportion of liquid with respect to gas in the coolant flowing in the coolant movement passage 3240.

According to an embodiment of the present application, coolants flowing out from the same reservoir 1100 may flow into the coolant cooling passage 3250 and the coolant movement passage 3240. The coolant flowing into the coolant movement passage 3240 may be sprayed to the target region TR, and the coolant flowing into the coolant cooling passage 3250 may not be sprayed to the target region TR. According to an embodiment of the present application, the coolants flowing into the coolant movement passage 3240 and the coolant cooling passage 3250 may be coolants flowing out from the same reservoir 1100, and the coolant that passed through the coolant movement passage 3240 may be sprayed to the target region TR through the nozzle unit 4100 while the coolant that passed through the coolant cooling passage 3250 is discharged to the outside via the control valve 3254.

The coolant cooling unit 3200 according to another embodiment of the present application has been described in detail above. However, although the coolant cooling unit 3200 has been described above on the basis of the drawing in which the coolant movement passage 3240 and the coolant cooling passage 3250 each form a single flow path, the coolant movement passage 3240 may be formed to have a plurality of flow paths, and the coolant cooling passage 3250 may also be formed to have a plurality of flow paths.

For example, the coolant cooling passage 3250 may form a single flow path, the coolant movement passage 3240 may be formed in a form surrounding the coolant cooling passage 3250, the coolant movement passage 3240 may include a plurality of connection pipes 3243, a coolant flowing into one transfer unit connection inlet 3241 may flow into the plurality of connection pipes 3243, and coolants flowing out of the plurality of connection pipes 3243 may be discharged to one valve connection outlet 3242 to be transferred to the valve 2100.

The cooling device 10000 may include the nozzle unit 4100. The nozzle unit 4100 may be provided in the form in which a cross-sectional area of a first end is different from a cross-sectional area of a second end. The nozzle unit 4100 may be provided in the form in which the cross-sectional area of the first end, which is relatively more spaced apart from the transfer unit 1200, is smaller than the cross-sectional area of the second end. Here, because of the phenomenon in which, due to the decrease of the cross-sectional area at the first end, the pressure increases and the pressure energy changes to speed energy, the nozzle unit 4100 may perform a function of allowing the coolant to flow out of the cooling device 10000.

The cooling device 10000 may include the spraying temperature regulating unit 3100. The spraying temperature regulating unit 3100 may perform a function of controlling the temperature of a coolant being sprayed. As a specific example, the spraying temperature regulating unit 3100 may include a heating element configured to regulate the temperature of a coolant in a flow path, through which the coolant may move, around the flow path.

According to an embodiment of the present application, the heating element may be a thermoelectric element. The thermoelectric element may include a first side thermally connected to the coolant to heat the coolant and a second side configured to perform an endothermic reaction according to an exothermic reaction of the first side. Here, the first side may be disposed more adjacent to the nozzle unit 4100 than the second side. In other words, the first side may be disposed more adjacent to the fluid through which the coolant moves than the second side.

The cooling device 10000 according to an embodiment of the present application may be configured to have a form in which the spraying temperature regulating unit 3100 is disposed between the valve 2100 and the nozzle unit 4100, and the spraying temperature regulating unit 3100 may perform an operation of heating the temperature of the coolant discharged through the outlet of the valve 2100 to allow the coolant to be sprayed through the nozzle unit 4100.

The cooling device 10000 may include at least one pipe. The pipe may be used in forming a flow path to allow the coolant transferred from the transfer unit 1200 in the cooling device 10000 to flow out through the nozzle unit 4100.

The cooling device 10000 may include a pipe that involves in forming a flow path used in moving the coolant to the solenoid valve 2100 from the transfer unit 1200 via the coolant cooling unit 3200. At least one pipe may be disposed between the transfer unit 1200 and the inlet of the solenoid valve 2100.

In a case in which a plurality of pipes are disposed between the transfer unit 1200 and the inlet of the solenoid valve 2100, a first pipe and a second pipe may be connected in a form that does not cause much outflow of coolant and form a flow path. As a specific example, the first pipe and the second pipe may be connected in the form of being fitted and coupled.

The cooling device 10000 may include a pipe that involves in forming a flow path used in moving the coolant to a coolant discharge port of the nozzle unit 4100 from the outlet of the solenoid valve 2100 via the spraying temperature regulating unit 3100.

In a case in which a plurality of pipes are disposed between the outlet of the solenoid valve 2100 and the coolant discharge port of the nozzle unit 4100, a third pipe and a fourth pipe may be connected in a form that does not cause much outflow of coolant and form a flow path. As a specific example, the third pipe and the fourth pipe may be connected in the form of being fitted and coupled.

The cooling device 10000 may further include a filter configured to filter impurities from a coolant flowing in the cooling device 10000. The filter may be installed in at least one region of the flow path through which the coolant flows in the cooling device 10000. The filter may have a form corresponding to the cross-sectional shape of the pipe. The filter may be made of a porous material. The filter may be made of a hydrophobic material.

The cooling system 1 may further include the input sensor 6300. The input sensor 6300 may acquire a signal corresponding to a user input. The input sensor 6300 may be implemented using a keyboard, a keypad, a button, a jog/shuttle, a wheel, and the like. The input sensor 6300 may be a key pad utilized as a switch.

The input sensor 6300 may be included in the cooling device 10000 according to the second embodiment of the present application. Alternatively, the input sensor 6300 may be formed in a main body that is separately present outside the cooling device 10000. Here, the main body may be electrically connected to the cooling device 10000 and control the cooling device 10000 on the basis of information input through the input sensor 6300.

The cooling device 10000 according to the second embodiment of the present application may include a switch configured to generate an electrical signal in response to user contact. The switch may perform a function of generating an electrical signal in response to generation of an electrostatic signal according to user contact. Alternatively, the switch may perform a function of generating an electrical signal in response to generation of a pressure of a predetermined numerical value or higher according to user contact.

The cooling system 1 may include the control unit 5000. The cooling system 1 may include a microcontroller. The microcontroller may generate a control signal for controlling the on/off and/or the opening/closing amount of the solenoid valve 2100 and transmit the generated control signal to the solenoid valve 2100. The microcontroller may generate a control signal for controlling the on/off of a cooling element of the coolant cooling unit 3200 and/or the amount of current applied to the cooling element of the coolant cooling unit 3200 and transmit the generated control signal to the cooling element. The microcontroller may generate a control signal for controlling the on/off of a heating element of the spraying temperature regulating unit 3100 and/or the amount of current applied to the heating element of the spraying temperature regulating unit and transmit the generated control signal to the heating element.

The microcontroller may be included in the cooling device 10000 according to the second embodiment of the present application. Alternatively, the microcontroller may be formed in a main body that is separately present outside the cooling device 10000. Here, the main body may be electrically connected to the cooling device 10000 and perform a function of providing the control signal generated by the microcontroller to at least one region of the cooling device 10000.

The cooling system 1 may further include a power source unit. The cooling system 1 may further include a power source unit configured to supply power for driving the cooling device 10000. The power source unit may include at least one of a direct-current power source for supplying direct current and an alternating-current power source for supplying alternating current. For example, the power source unit may be in the form of a battery or a dry cell. As another example, the power source unit may be in the form of a power line that continuously receives power.

The power source unit may be included in the cooling device 10000 according to the second embodiment of the present application. Alternatively, the power source unit may be formed in a main body that is separately present outside the cooling device 10000. Here, the main body may be electrically connected to the cooling device 10000 and perform a function of providing the power input through the power source unit to at least one region of the cooling device 10000.

The power source unit may supply power to the control unit 5000. The power source unit may supply power to the solenoid valve 2100. The power source unit may supply power for controlling the opening and closing of the solenoid valve 2100.

The cooling device 10000 according to an embodiment of the present application may include a distance maintaining unit 4900 configured to guide a distance between the target region TR and the cooling device 10000. For example, the distance maintaining unit 4900 may perform a function of constantly maintaining the distance between the target region TR and the cooling device 10000 to a predetermined distance. As a specific example, the distance maintaining unit 4900 may be implemented in the form of a rod having a predetermined length to maintain the distance between the target region TR and the cooling device 10000 to the same distance at all times. As another example, the distance maintaining unit 4900 may perform a function of determining the distance between the target region TR and the cooling device 10000 according to an operation mode of the cooling device 10000 to maintain the distance between the target region TR and the cooling device 10000 to a determined distance. As a specific example, the distance maintaining unit 4900 may be implemented in the form of a length-adjustable rod, and the length thereof may be adjusted according to an electrical signal applied from the control unit 5000.

The cooling device 10000 according to the second embodiment of the present application has been disclosed above. However, the above description only discloses one specific embodiment intended to help in understanding, and thus the form of the cooling device 10000 disclosed by the present application is not limited to the cooling device 10000 according to the second embodiment that has been described above, and the scope of the present application should be determined on the basis of the claims below.

5. Basic Configuration of Cooling Device 10000 According to Third Embodiment A cooling device according to a third embodiment of the present application is identical to the cooling device described above in sections 1. Elements of cooling device, 2. Structure of cooling device, 3. Basic configuration according to first embodiment, and 4. Basic configuration according to second embodiment, except that the cooling device according to the third embodiment of the present application includes a spraying unit 4000. Hereinafter, the spraying unit 7000 will be described.

The cooling device according to the third embodiment of the present application relates to a cooling device that, in a case in which cooling therapy is performed for pain relief and anesthesia of mucous membranes such as the skin and eye of a patient, brings a cooling tip 7200 cooled by a sprayed coolant in contact with the body of the patient. Hereinafter, the spraying unit 7000 will be mainly described.

3-1 Embodiment

Figure 12:
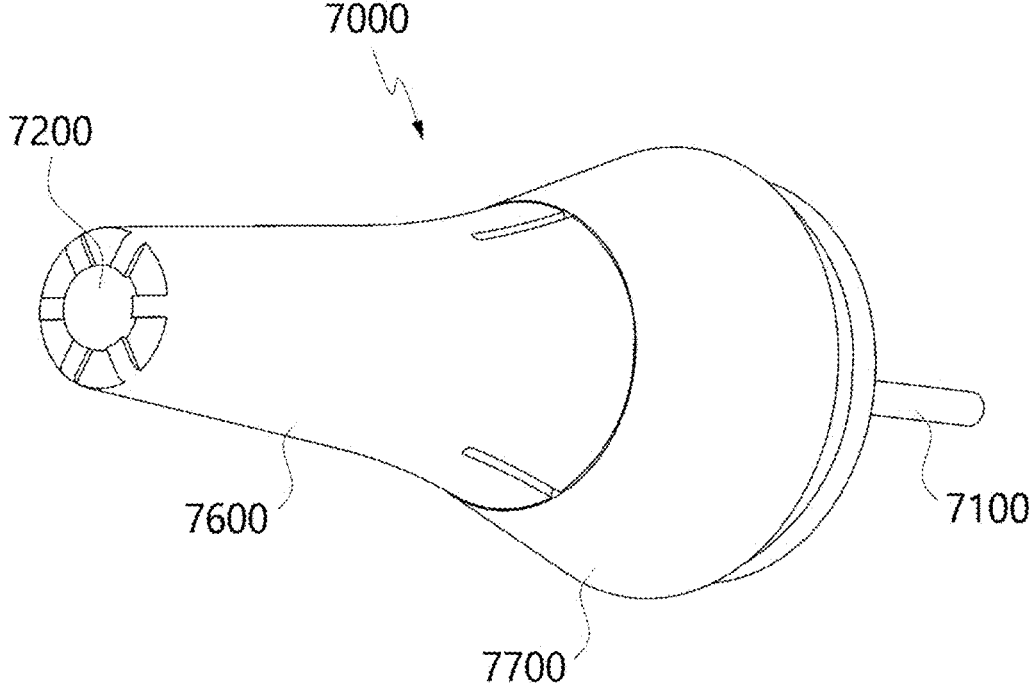
FIG. 12 is a perspective diagram illustrating a spraying unit 7000 according to a 3-1 embodiment of the present application.
Figure 13:
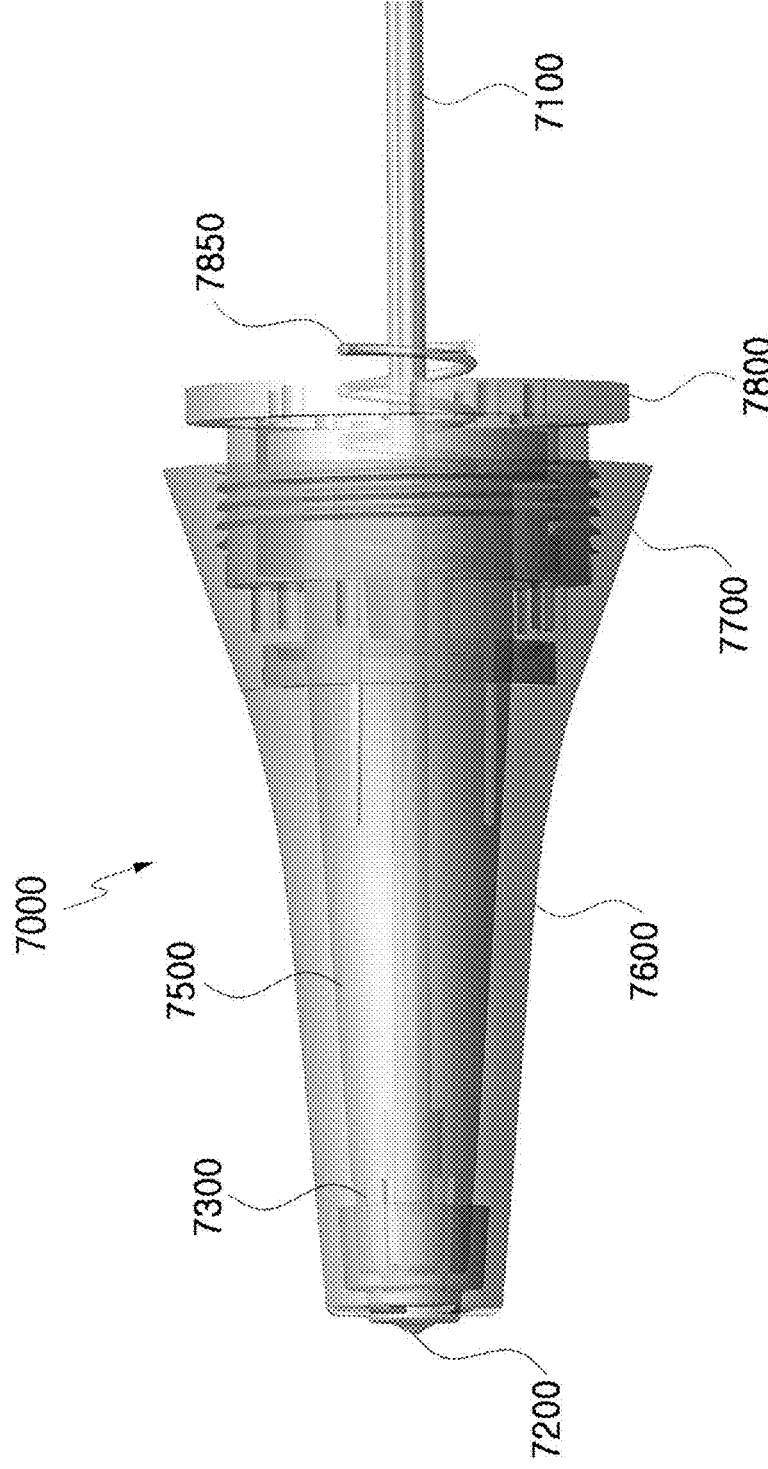
FIG. 13 is a translucent diagram illustrating the spraying unit 7000 according to the 3-1 embodiment of the present application.
Figure 14:
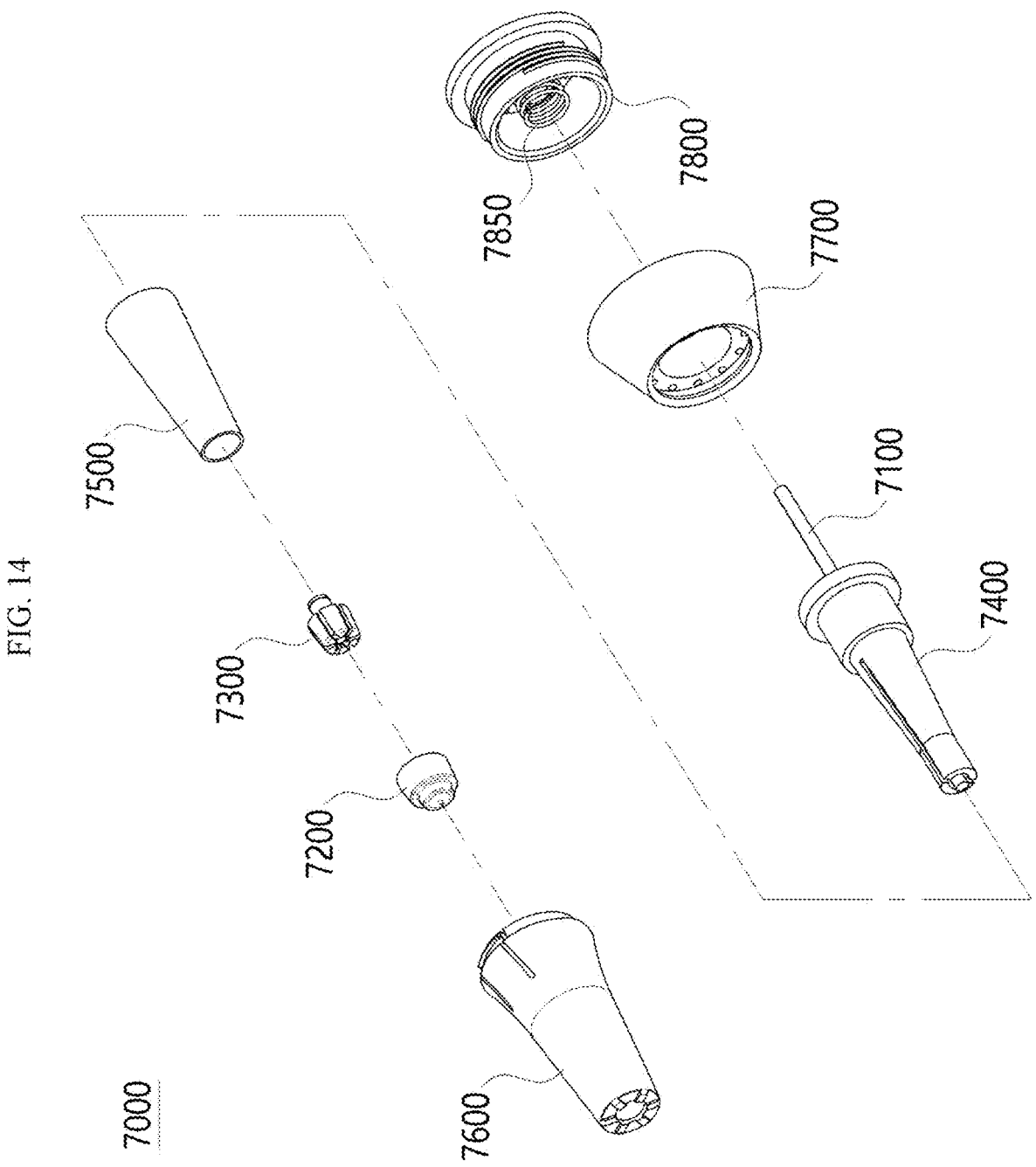
FIG. 14 is a disassembled diagram illustrating the spraying unit 7000 according to the 3-1 embodiment of the present application.
Figure 15:
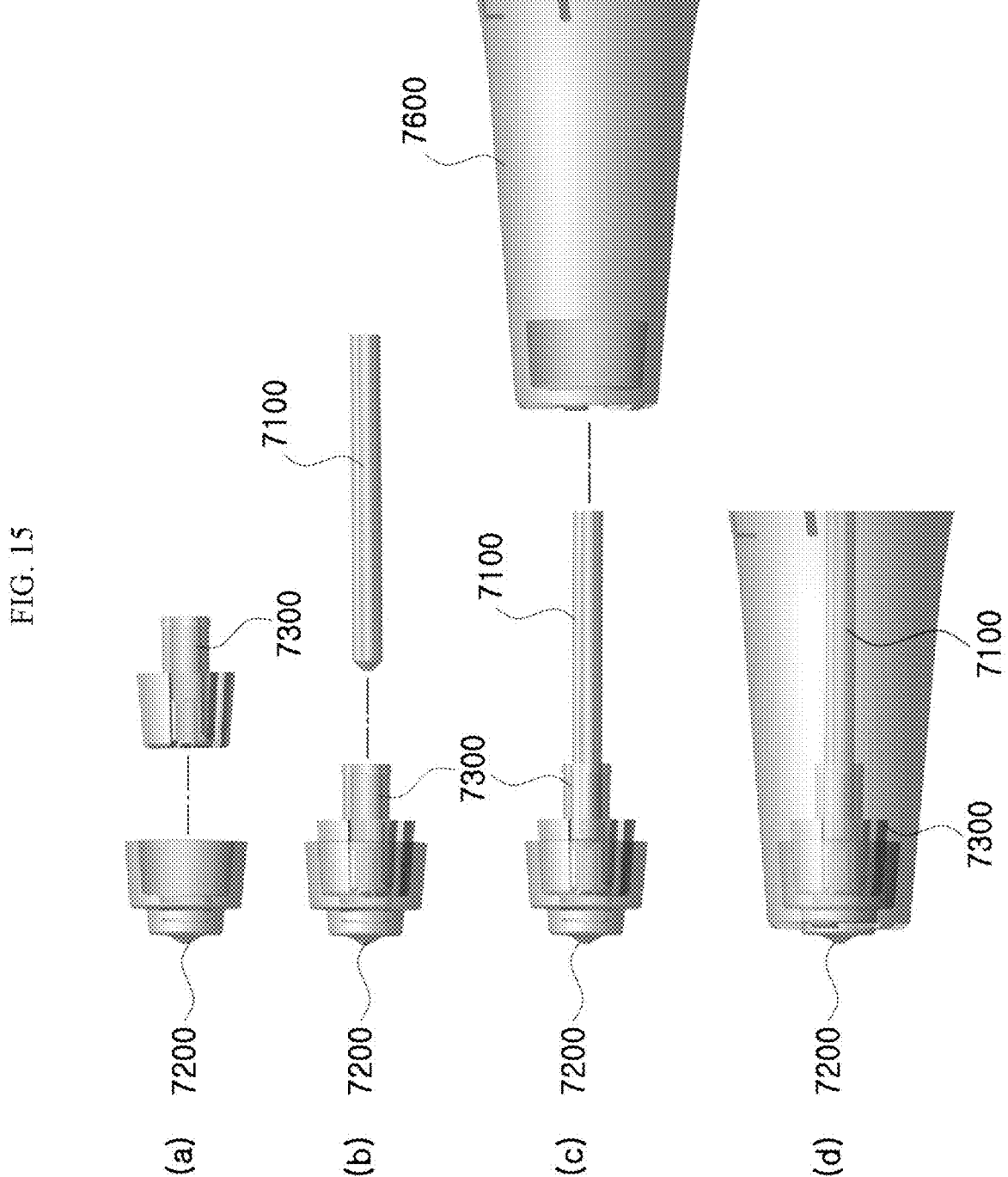
FIG. 15 is a diagram for describing a coupling process of the spraying unit 7000 according to the 3-1 embodiment of the present application.
Figure 16:
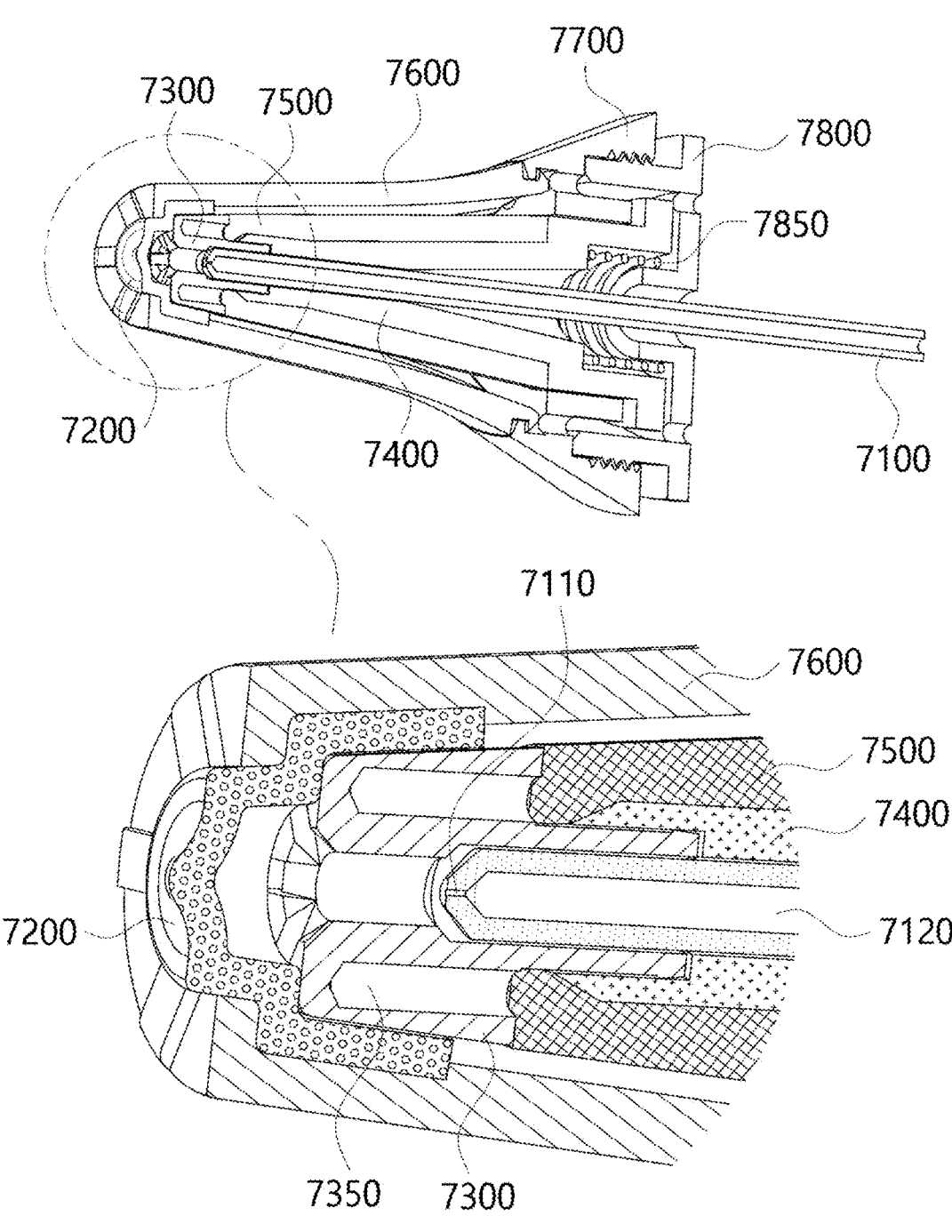
FIG. 16 is a diagram illustrating a cross-section of the spraying unit 7000 according to the 3-1 embodiment of the present application.

FIG. 12 is a diagram illustrating the spraying unit 7000 according to a 3-1 embodiment of the present application, FIG. 13 is a diagram illustrating the spraying unit 7000 according to the 3-1 embodiment of the present application, and FIG. 14 is a diagram illustrating the spraying unit 7000 according to the 3-1 embodiment of the present application. FIG. 15 is a diagram for describing a coupling process of the spraying unit 7000 according to the 3-1 embodiment of the present application. FIG. 16 is a cross-sectional view illustrating the spraying unit 7000 according to the 3-1 embodiment of the present application.

Referring to FIGS. 12 to 16, the spraying unit 7000 according to the 3-1 embodiment of the present application may include a nozzle unit 7100, a cooling tip 7200, a cooling medium 7300, a nozzle unit insulator 7400, an insulator cover 7500, a front end cover 7600, a rear end cover 7700, and an elastic coupling portion 7800. As compared to other embodiments described above, the cooling device according to the 3-1 embodiment of the present application may selectively further include at least any one element of the coolant supply unit 1000, the flow regulating unit 2000, the coolant state regulating unit 3000, the control unit 5000, and the sensor unit 6000, except for the spraying unit 7000.

The nozzle unit 7100 may perform a function of providing a passage through which the coolant in the cooling device 10000 may be discharged. For example, the nozzle unit 7100 may be a tube formed to allow the coolant flowing in at least one region in the cooling device 10000 to be jetted to a free space. The nozzle unit 7100 may receive a coolant from a solenoid valve and transfer the coolant to the cooling medium 7300 and the cooling tip 7200. The valve may control the flow of coolant transferred to the nozzle unit by using a pulse width modulation (PWM) method.

The nozzle unit 7100 may be a tube disposed at one end of a flow path formed in the cooling device 10000.

The nozzle unit 7100 may include a tube having a relatively small cross-sectional area.

The nozzle unit 7100 may have various shapes. For example, the nozzle unit 7100 may be a straight nozzle. The nozzle unit 7100 may be a straight nozzle having a hollow formed therein in the longitudinal direction.

A passage through which the coolant flows in the nozzle unit 7100 may be referred to as a first channel. The first channel may be divided into a front end and a region excluding the front end, and in the first channel, a diameter/width/area of the front end region 7110 may be smaller than a diameter/width/area of the region 7120 excluding the front end. The coolant flowing through the region excluding the front end in the nozzle unit 7100 may receive high pressure upon entering the front end region of the nozzle unit 7100. Then, the coolant flowing through the front end region of the nozzle unit 7100 may adiabatically expand in a wide space while moving to the cooling medium, and the temperature of the coolant may be lowered due to the Joule-Thomson effect.

The nozzle unit 7100 may have wear resistance and pressure resistance. In other words, the nozzle unit 7100 may be made of a material which is not damaged much due to friction or the pressure of the coolant. For example, the nozzle unit 7100 may be made of an aluminum alloy, a steel alloy, tungsten, stainless steel, or a copper alloy, but the material of the nozzle unit 7100 is not limited thereto.

Figure 17A:
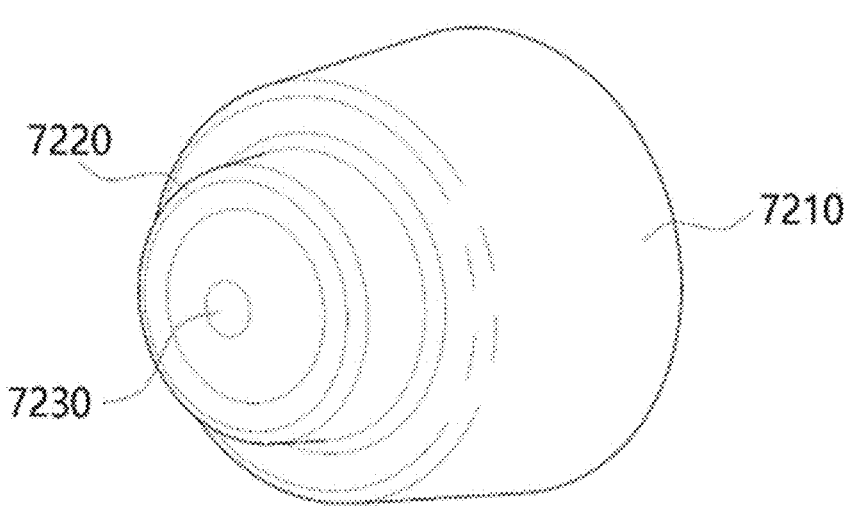
FIGS. 17A and 17B are perspective diagrams illustrating a cooling tip 7200 according to the 3-1 embodiment of the present application.
Figure 17B:
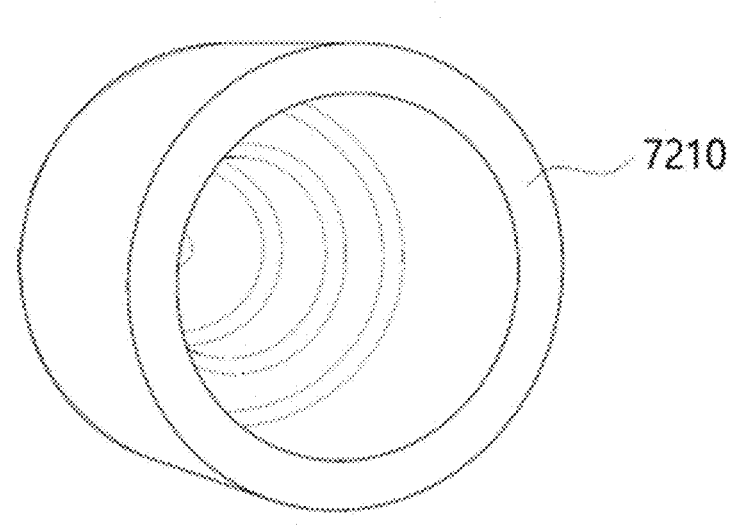

The spraying unit 7000 according to the 3-1 embodiment of the present application may include the cooling tip 7200. FIGS. 17A and 17B are diagrams illustrating the cooling tip 7200 according to the 3-1 embodiment of the present application.

Referring to FIGS. 12 to 16 together with FIGS. 17A and 17B are, the cooling tip 7200 may be cooled by the cooling medium 7300. The cooling tip 7200 may be cooled by a coolant. More specifically, when the coolant that passed through the nozzle unit 7100 is cooled as the coolant passes through the cooling medium 7300, the cooling tip 7200 which is in direct physical contact with the cooling medium 7300 may be cooled due to receiving a flow of heat transmitted from the cooling medium 7300 by conduction. Also, the cooling tip 7200 may come in direct contact with the coolant that passed through the cooling medium 7300 and may be cooled due to receiving a flow of heat transmitted by at least any one of conduction or convection. The cooling tip 7200 may be cooled by the cooling medium 7300, which is cooled by the coolant, and coolants.

The cooling tip 7200 may include a cooling medium coupling portion 7210 which is coupled to the cooling medium 7300 and a coolant contact portion 7220 which is disposed at a front end of the cooling medium coupling portion 7210 and includes an outer surface whose diameter/width/area is smaller than that of the cooling medium coupling portion 7210. The cooling medium coupling portion 7210 may have a cylindrical shape. The cooling medium coupling portion 7210 may have a diameter/width/area that allows coupling to a front end of the cooling medium 7300. The inside of the cooling medium coupling portion 7210 may be configured as an empty space to allow coupling to the cooling medium 7300. The cooling medium 7300 may be coupled to the cooling medium coupling portion 7210 by being fitted thereto. The structure of the cooling medium coupling portion 7210 is not limited to specific shapes and methods as long as the cooling medium coupling portion 7210 is able to come in direct physical contact with the cooling medium 7300 to receive a flow of heat well from the cooling medium 7300.

The coolant contact portion 7220 may be integrally configured with the cooling medium coupling portion 7210. The coolant contact portion 7220 may be disposed at a front end of the cooling medium coupling portion 7210 and have an outer surface or outer circumferential surface whose diameter/width/area is smaller than that of the cooling medium coupling portion 7210. The coolant contact portion 7220 may have a cylindrical shape. A front end of the coolant contact portion 7220 may include a closed surface as a place that comes in contact with the human body. The inside of the coolant contact portion 7220 may be configured as an empty space. The coolant that passed through the cooling medium 7300 may be discharged to the inside of the coolant contact portion 7220, and the coolant may cool the coolant contact portion 7220. The coolant that reached the coolant contact portion 7220 may exit the cooling device through a coolant discharge path 7320 of the cooling medium 7300.

In the cooling tip 7200, a front surface of the coolant contact portion 7220 that faces the outside of the cooling device may serve as a marker. In this case, when the cooling tip 7200 comes in contact with an eye or the skin of a patient to cool or anesthetize the eye or skin of the patient, a mark corresponding to the front surface of the coolant contact portion 7220 may be formed on the body of the patient. The width/diameter of the front surface of the coolant contact portion 7220 may be 3 mm or more. Also, the cooling tip 7200 may include a separate marker 7230 on the front surface of the coolant contact portion 7220. When the cooling tip 7200 comes in contact with an eye or the skin of a patient to cool or anesthetize the eye or skin of the patient, the marker 7230 may form a mark on the patient's body. The marker 7230 has a front end protruding from the coolant contact portion to apply a pressure to the patient's body. The diameter of the marker 7230 may be about 3 mm or less. All of the coolant contact portion 7220, the cooling medium coupling portion 7210, and the marker 7230 may be integrally configured.

The cooling tip 7200 may be a component that is replaceable after being used one time. The cooling tip 7200 may be a component that is replaceable together with the front end cover 7600 which will be described below. The cooling tip 7200 may be replaced together with the front end cover 7600 when the front end cover 7600 is replaced or may be separately replaced while the front end cover 7600 is still in use. The cooling tip 7200 may be separated from the front end cover 7600 after the front end cover 7600 is separated from the rear end cover 7700. The cooling tip 7200 may be replaced together with the front end cover 7600 after the front end cover 7600 is separated from the rear end cover 7700.

The cooling tip 7200 may be made of a metal having high thermal conductivity. Typically, the cooling tip 7200 may be made of aluminum.

Figure 18A:
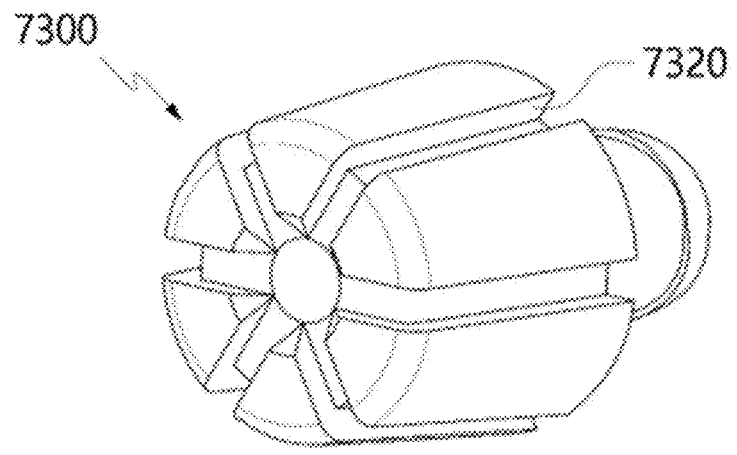
FIGS. 18A and 18B are perspective diagrams illustrating a cooling medium 7300 according to the 3-1 embodiment of the present application.
Figure 18B:
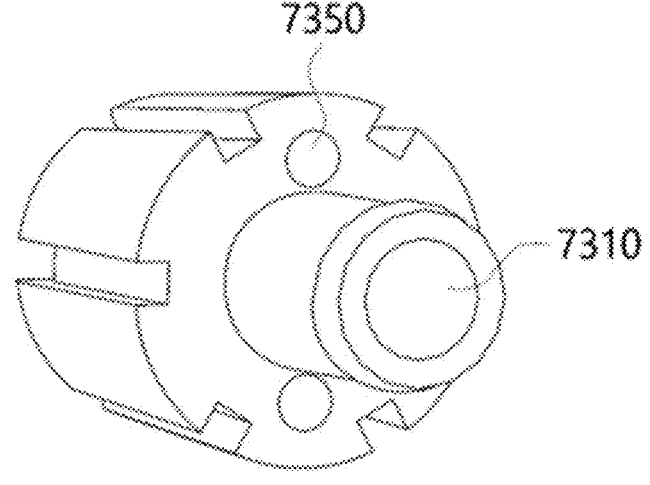

The spraying unit 7000 according to the 3-1 embodiment of the present application may include the cooling medium 7300. FIGS. 18A and 18B are diagrams illustrating the cooling medium 7300 according to the 3-1 embodiment of the present application.

Referring to FIGS. 12 and 16 together with FIGS. 18A and 18B, the cooling medium 7300 may be cooled as the coolant that passed through the nozzle unit 7100 passes through the cooling medium 7300. The cooling medium 7300 may transfer the coolant that passed through the nozzle unit 7100 to the cooling tip 7200. A spraying temperature regulating unit configured to control the temperature of the coolant being transferred to the cooling medium may be further included between the nozzle unit and the cooling medium. The spraying temperature regulating unit may be a Peltier element.

The cooling medium 7300 may include a long hollow formed therein at the center. The hollow may be referred to as a second channel 7310. The coolant that passed through the nozzle unit 7100 may cool the cooling medium 7300 as the coolant passes through the second channel 7310. After passing through the cooling medium 7300, the coolant may reach the cooling tip 7200, more specifically, the coolant contact portion 7220, to cool the cooling tip 7200.

The cooling medium 7300 may be coupled to the cooling medium coupling portion 7210, which is the rear end of the cooling tip 7200, by being fitted thereto. The front end of the cooling medium 7300 may have a cylindrical shape in which one or more coolant discharge paths 7320 are formed in the shape of a long recess on an outer surface. The rear end of the cooling medium 7300 may have a cylindrical shape in which the front end of the nozzle unit 7100 is coupled to the inside of the second channel 7310.

The cooling medium 7300 may be made of a metal having high thermal conductivity. Typically, the cooling medium 7300 may be made of aluminum, copper, iron, or an alloy containing at least one or more thereof.

The cooling medium 7300 may include a groove 7350 formed around the long hollow at the center. The cooling device may include a temperature sensor disposed in the groove 7350 of the cooling medium 7300. The cooling device should precisely control the temperature of the cooling device according to a method of treating a patient, and to this end, the cooling device should measure a temperature of a component coming in contact with an affected area of a patient or a component adjacent thereto. Although the cooling tip is a portion of the cooling device that comes in direct contact with an affected area of the human body, since the cooling tip 7200 is a component that is replaced after being used one time, installing a temperature sensor in the cooling tip 7200 is not efficient in terms of product design.

Therefore, it may be efficient to measure a temperature by installing a temperature sensor in the cooling medium 7300 that is disposed closest to the cooling tip 7200 and comes in contact therewith and that comes in direct contact with the cooling tip 7200 and transmits a flow of heat through coolant transfer. In this case, even when the temperature of the cooling tip 7200 is not measured directly, the temperature of the cooling tip 7200 may be estimated/controlled by measuring the temperature of the cooling medium 7300 and controlling the amount of coolant.

Here, before the cooling temperature of the cooling tip 7200 and the cooling medium 7300 reaches a normal state, in order to make a dynamic temperature change to occur within a predetermined range, the cooling tip 7200 and the cooling medium 7300 may have heat capacities within a predetermined ratio range. Also, materials of the cooling tip 7200 and the cooling medium 7300 may be selected to have heat capacities of the predetermined ratio. For example, the heat capacity of the cooling tip 7200 may be 0.1 to 5 times the heat capacity of the cooling medium 7300. When the heat capacity of the cooling tip 7200 is not equal to the heat capacity of the cooling medium 7300, a portion where the cooling tip 7200 comes in contact with a coolant may be increased or decreased, or an area in which the cooling tip 7200 and the cooling medium 7300 come in contact with each other may be controlled to make a temperature response occur within a predetermined range. When the heat capacity of the cooling tip 7200 is lower than 0.1 times the heat capacity of the cooling medium 7300 or higher than 5 times the same, since a heat capacity difference between the cooling tip 7200 and the cooling medium 7300 is too large, it may not be easy to control the temperature by controlling the contact area between the cooling tip 7200 and the cooling medium 7300 or controlling the area in which the coolant comes in contact with the cooling tip 7200. In order to improve dynamic temperature responsiveness of the cooling medium 7300, the cooling medium 7300 may be thermally separated from other elements of the cooling device, and to this end, the cooling medium 7300 may be insulated from the other elements through the nozzle unit insulator 7400.

Hereinafter, a cooling method according to the 3-1 embodiment of the present application will be described in more detail with reference to FIGS. 15 and 16.

Referring to FIGS. 15 and 16, by the sprayed coolant cooling the cooling tip 7200, which is at the foremost end of the cooling device, and the cooling tip 7200 coming in contact with the human body, more specifically, an eye, the cooling device may relieve pain of an affected area or anesthetize the affected area. The cooling tip 7200 may be cooled by two cooling means, the cooling medium 7300 and a coolant. More specifically, the coolant transferred through the nozzle unit 7100 may cool the cooling medium 7300, and the cooled cooling medium 7300 may cool the cooling tip 7200 again. Also, the coolant that passed through the nozzle unit 7100 and the cooling medium 7300 is transferred to the cooling tip 7200 again, and thus the cooling tip 7200 may be additionally cooled by the coolant. When the cooling device operates, the coolant may be discharged to an empty space between the cooling tip 7200 and the cooling medium 7300 which are coupled to each other. The empty space may be an inner space of the coolant contact portion 7220 in the cooling tip 7200. The coolant in contact with the cooling tip 7200 may exit to the outside through the coolant discharge path 7320 of the cooling medium 7300.

In the nozzle unit 7100, a diameter of a front end of a first channel may be less than a diameter of a region of the first channel excluding the front end thereof. By making the diameter of the front end of the first channel smaller than the diameter of the region of the first channel excluding the front end thereof, when the coolant is discharged from the nozzle unit 7100, the temperature of the coolant may be dropped due to the Joule-Thomson effect.

In the cooling medium 7300, the diameter of the second channel 7310 may be larger than the diameter of the first channel of the nozzle unit 7100 and may be substantially the same as the outer diameter of the nozzle unit 7100. By making the diameter of the second channel 7310 larger than the diameter of the first channel, the coolant discharged from the nozzle unit 7100 may diffuse from the second channel 7310 and cool the cooling medium 7300. Also, by making the diameter of the second channel 7310 substantially the same as the outer diameter of the nozzle unit 7100, a gap between the cooling medium 7300 and the nozzle unit 7100 may be minimized.

Hereinafter, the nozzle unit insulator 7400, the insulator cover 7500, the front end cover 7600, the rear end cover 7700, and the elastic coupling portion 7800 of the spraying unit 7000 according to the 3-1 embodiment of the present application will be described.

Referring to FIGS. 14 and 16, the nozzle unit insulator 7400 may electrically insulate the nozzle unit 7100 from other components. The nozzle unit insulator 7400 may block heat from the outside to prevent the coolant flowing in the nozzle unit 7100 from being affected by an external environment.

The nozzle unit insulator 7400 may have a cylindrical shape surrounding the nozzle unit 7100. The nozzle unit insulator 7400 may have a width/area/diameter that increases in a direction toward a rear end thereof. A front end of the nozzle unit insulator 7400 may be coupled to surround the rear end of the cooling medium 7300. The rear end of the cooling medium 7300 may be coupled to surround the front end of the nozzle unit 7100, and the nozzle unit insulator 7400 may be coupled to surround the rear end of the cooling medium 7300. The nozzle unit 7100 may be positioned at its correct position by the cooling medium 7300 and the nozzle unit insulator 7400.

The nozzle unit insulator 7400 may be made of plastic.

The insulator cover 7500 may block heat from the outside to prevent the coolant flowing in the nozzle unit 7100 from being affected by an external environment. The insulator cover 7500 may prevent heat of the nozzle unit 7100 from exiting to the outside to minimize heat loss. Also, the insulator cover 7500 may eliminate a risk or an inconvenience that may occur due to the coolant being jetted to the outside unintentionally.

The insulator cover 7500 may be disposed to surround the nozzle unit insulator 7400 and have a cylindrical shape. The insulator cover 7500 may have a width/area/diameter that increases in a direction toward a rear end thereof. The insulator cover 7500 may receive an elastic force, which is provided from the elastic coupling portion 7800 which will be described below, from the nozzle unit insulator 7400 and transmit the elastic force to the cooling tip 7200 and the cooling medium 7300 to increase a coupling force between the cooling tip 7200 and the cooling medium 7300. The cooling tip 7200 and the cooling medium 7300 may be pressed against each other due to the elastic force.

The insulator cover 7500 may be made of plastic.

The front end cover 7600 may be disposed to surround the insulator cover 7500 and the cooling tip 7200. The front end cover 7600 may have a cylindrical shape. The front end cover 7600 may have a width/area/diameter that increases in a direction toward a rear end thereof.

The front end cover 7600 may protect components within the front end cover 7600 from physical impact in an external environment. A hole may be formed in a front end of the front end cover 7600. The coolant contact portion 7220 and the marker 7230 of the cooling tip 7200 may be exposed to the outside of the cooling device through the hole of the front end cover 7600.

The front end cover 7600 may be a disposable component that may be replaced. The front end cover 7600 may be coupled to the rear end cover 7700, which will be described below, by male-female coupling. To facilitate replacement of the front end cover 7600, the front end cover 7600 may be separated from the rear end cover 7700 by, for example, a physical external force caused by pressing.

The front end cover 7600 may be made of plastic.

The rear end cover 7700 may be disposed at a rear end of the front end cover 7600 and may be coupled to the rear end of the front end cover 7600 and the rear end of the nozzle unit insulator 7400. The rear end cover 7700 may be coupled to the elastic coupling portion 7800, which will be described below, by screw fastening.

The rear end cover 7700 may have a cylindrical shape and have a width/area/diameter that increases in a direction toward a rear end thereof. The rear end cover 7700 may have a hollow having a size that allows the nozzle unit 7100 and the nozzle unit insulator 7400 to pass through the hollow. The rear end of the nozzle unit insulator 7400 may be coupled to a rear end of the rear end cover 7700 after the nozzle unit insulator 7400 passes through the rear end cover 7700.

The rear end cover 7700 may be made of metal having high strength and wear resistance to prevent deformation even when the front end cover 7600 is frequently replaced.

The elastic coupling portion 7800 may be coupled to the nozzle unit insulator 7400 and the rear end cover 7700. The elastic coupling portion 7800 may be coupled to the rear end of the nozzle unit insulator 7400 and the rear end of the rear end cover 7700. The elastic coupling portion 7800 may be coupled to a main body portion of the cooling device that includes a coolant supply unit, a flow regulation unit, a coolant state regulating unit, a control unit, and a sensor unit.

The elastic coupling portion 7800 may include a spring 7850. The spring 7850 may be disposed in an inner space of the nozzle unit insulator 7400. The spring 7850 may be disposed between the nozzle unit 7100 and the elastic coupling portion 7800 to provide an elastic force to the nozzle unit insulator 7400. When all of the cooling tip 7200, the cooling medium 7300, the nozzle unit 7100, the nozzle unit insulator 7400, the insulator cover 7500, the front end cover 7600, the rear end cover 7700, and the elastic coupling portion 7800 of the spraying unit 7000 are coupled, the elastic coupling portion 7800 may serve to minimize a gap between the cooling tip 7200 and the cooling medium 7300 by the elastic force of the spring 7850. The spring 7850 may directly provide the elastic force to the nozzle unit insulator 7400 and the insulator cover 7500, and the nozzle unit insulator 7400 and the insulator cover 7500 may transmit the elastic force to the cooling medium 7300 to increase the coupling force between the cooling tip 7200 and the cooling medium 7300.

The spraying unit 7000 according to the 3-1 embodiment of the present application may selectively further include a nozzle guide unit 7150 and an orifice 7900. The nozzle guide unit 7150 may be disposed between the cooling medium 7300 and a nozzle to induce coupling of the cooling medium 7300 and the nozzle and alignment thereof. The orifice 7900 may be disposed between the nozzle guide unit 7150 and the nozzle unit 7100 to transfer the coolant to the cooling medium 7300. The nozzle guide unit 7150 and the orifice 7900 will be described in detail below in describing a 3-2 embodiment of the present application.

3-2 Embodiment

Figure 19:
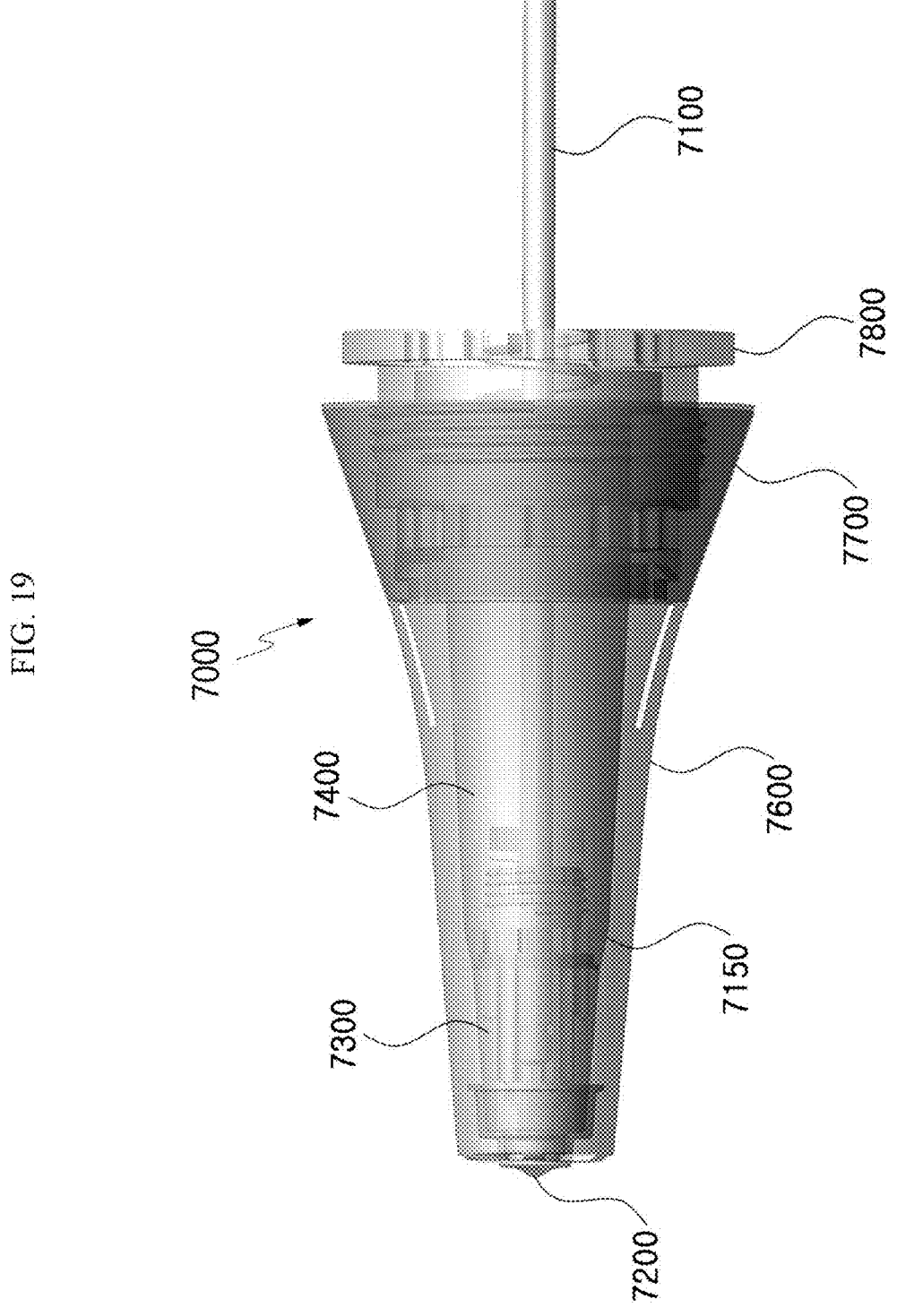
FIG. 19 is a translucent diagram illustrating a spraying unit 7000 according to a 3-2 embodiment of the present application.
Figure 20:
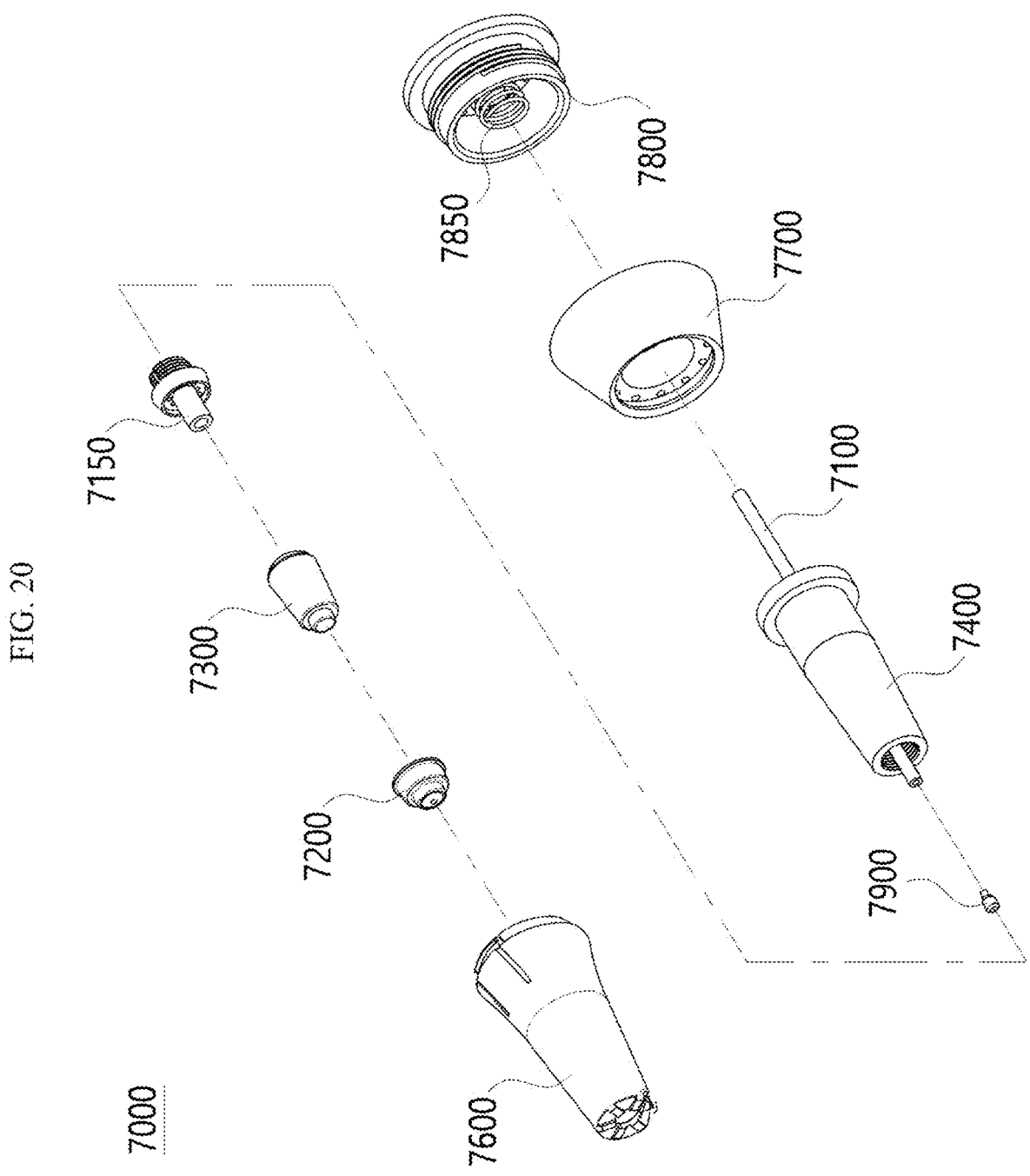
FIG. 20 is a disassembled diagram illustrating the spraying unit 7000 according to the 3-2 embodiment of the present application.
Figure 21:
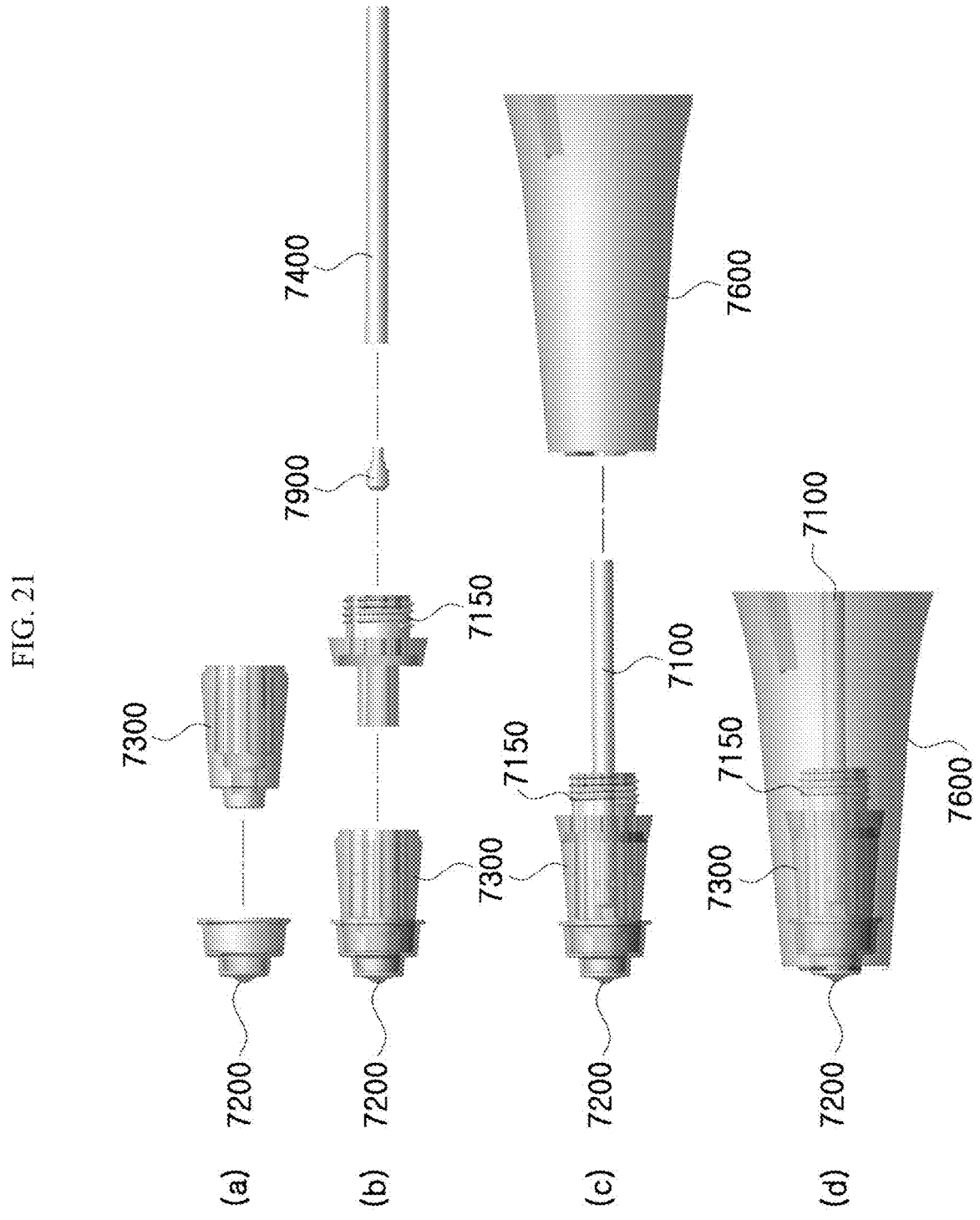
FIG. 21 is a diagram for describing a coupling process of the spraying unit 7000 according to the 3-2 embodiment of the present application.
Figure 22:
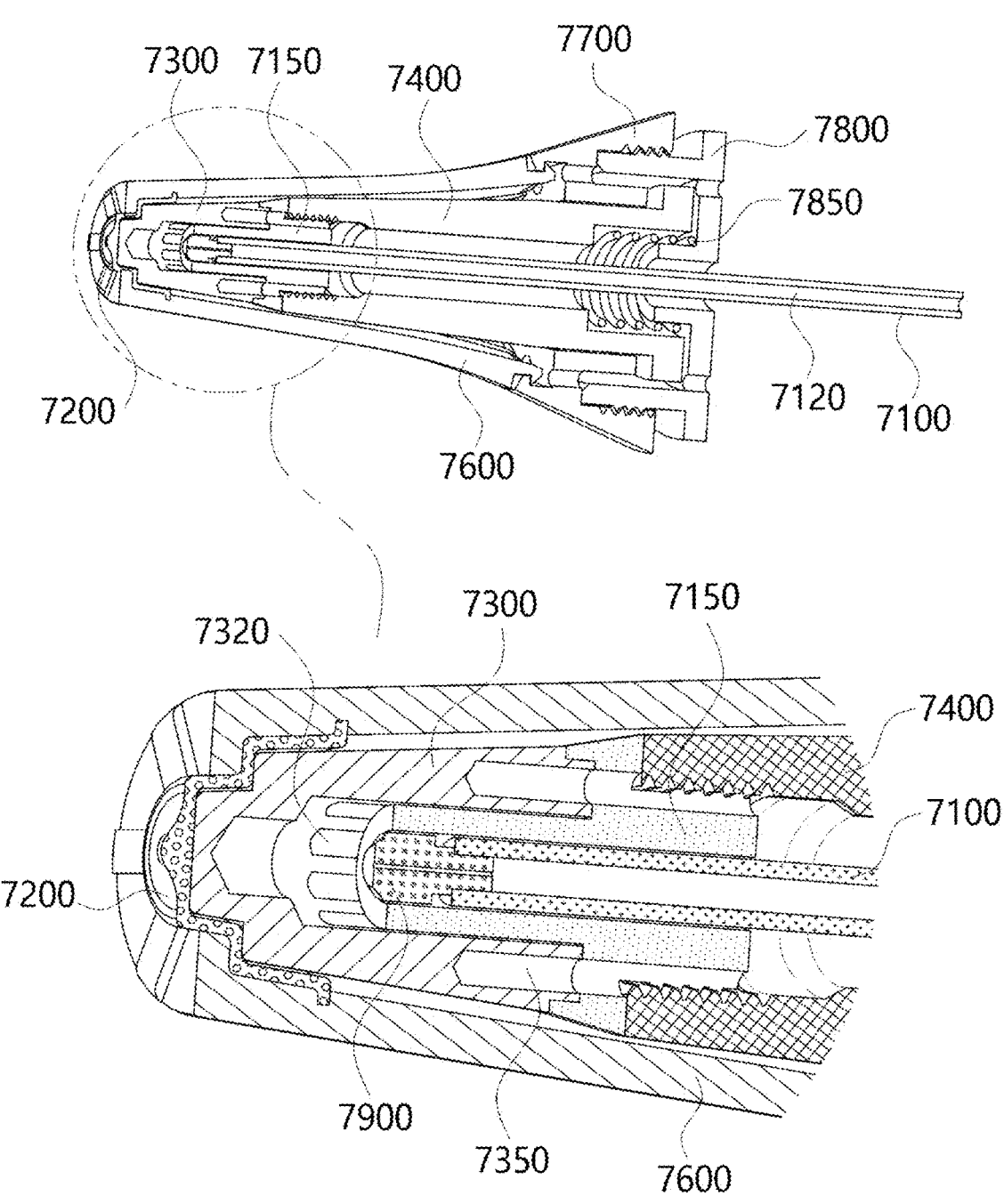
FIG. 22 is a diagram illustrating a cross-section of the spraying unit 7000 according to the 3-2 embodiment of the present application.

FIG. 19 is a see-through view illustrating a spraying unit 7000 according to a 3-2 embodiment of the present application. FIG. 20 is an exploded view illustrating the spraying unit 7000 according to the 3-2 embodiment of the present application. FIG. 21 is a view for describing a coupling process of the spraying unit 7000 according to the 3-2 embodiment of the present application. FIG. 22 is a cross-sectional view illustrating the spraying unit 7000 according to the 3-2 embodiment of the present application.

Referring to FIGS. 19 to 22, the spraying unit 7000 according to the 3-2 embodiment of the present application may include the nozzle unit 7100, the cooling tip 7200, the cooling medium 7300, the nozzle guide unit 7150, the orifice 7900, the nozzle unit insulator 7400, the insulator cover 7500, the front end cover 7600, the rear end cover 7700, and the elastic coupling portion 7800.

Hereinafter, differences between the cooling device according to the 3-2 embodiment of the present application and the cooling device according to the 3-1 embodiment of the present application will be mainly described. The cooling device according to the 3-2 embodiment of the present application may also selectively further include at least any one element of the coolant supply unit 1000, the flow regulation unit 2000, the coolant state regulating unit 3000, the control unit 5000, and the sensor unit 6000, except for the spraying unit 7000.

The cooling device according to the 3-2 embodiment of the present application may be configured to have a structure in which the cooling medium 7300 comes in direct physical contact with the cooling tip 7200 and the cooling tip 7200 is cooled by the cooling medium 7300. More specifically, a front surface of the cooling medium 7300 may be configured as a closed surface, and the coolant transferred to the cooling medium 7300 through the nozzle unit 7100 may not come in direct contact with the cooling tip 7200. The cooling tip 7200 may be cooled by receiving heat from the cooling medium 7300 by conduction. Alternatively, the cooling device according to the 3-2 embodiment of the present application may further include the nozzle guide unit 7150 and the orifice 7900 which are disposed between the cooling medium 7300 and the nozzle unit 7100. The nozzle guide unit 7150 and the orifice 7900 are components that may be selectively added in designing the cooling device and thus may also be applied to the cooling device according to the 3-1 embodiment that has been described above.

The nozzle unit 7100 may perform a function of providing a passage through which the coolant in the cooling device 10000 may be discharged. For example, the nozzle unit 7100 may be a tube formed to allow the coolant flowing in at least one region in the cooling device 10000 to be jetted to a free space. The nozzle unit 7100 may receive a coolant from a solenoid valve and transfer the coolant to the cooling medium 7300. The valve may control the flow of coolant transferred to the nozzle unit by using the PWM method. The nozzle unit 7100 may transfer the coolant to the cooling medium 7300 through the orifice 7900. The nozzle unit 7100 may transfer the coolant to the cooling medium 7300 through the orifice 7900 and the nozzle guide unit 7150.

The nozzle unit 7100 may be a tube disposed at one end of a flow path formed in the cooling device 10000. The nozzle unit 7100 may include a tube having a relatively small cross-sectional area.

The nozzle unit 7100 may have various shapes. For example, the nozzle unit 7100 may be a straight nozzle. The nozzle unit 7100 may be a straight nozzle having a hollow formed therein in the longitudinal direction.

A passage through which the coolant flows in the nozzle unit 7100 may be referred to as a first channel. The first channel may be divided into a front end and a region excluding the front end, and in the first channel, a diameter/width/area of a front end region may be smaller than a diameter/width/area of a region excluding the front end. The coolant flowing through the region excluding the front end in the nozzle unit 7100 may receive high pressure upon entering the front end region of the nozzle unit 7100. Then, the coolant flowing through the front end region of the nozzle unit 7100 may adiabatically expand in a wide space while moving to the cooling medium, and the temperature of the coolant may be lowered due to the Joule-Thomson effect. The diameter/width/area of the first channel may be the same throughout the entire region of the nozzle unit 7100. The nozzle unit 7100 may be coupled to the orifice 7900 which will be described below, and a diameter/width/area of a passage 7910 through which the coolant flows in the orifice 7900 may be less than the diameter/width/area of the first channel. The coolant flowing in the nozzle unit 7100 may receive high pressure upon entering the orifice 7900. Then, the coolant flowing along the passage of the orifice 7900 may adiabatically expand in a wide space while moving to the cooling medium, and the temperature of the coolant may be lowered due to the Joule-Thomson effect.

Figure 23A:
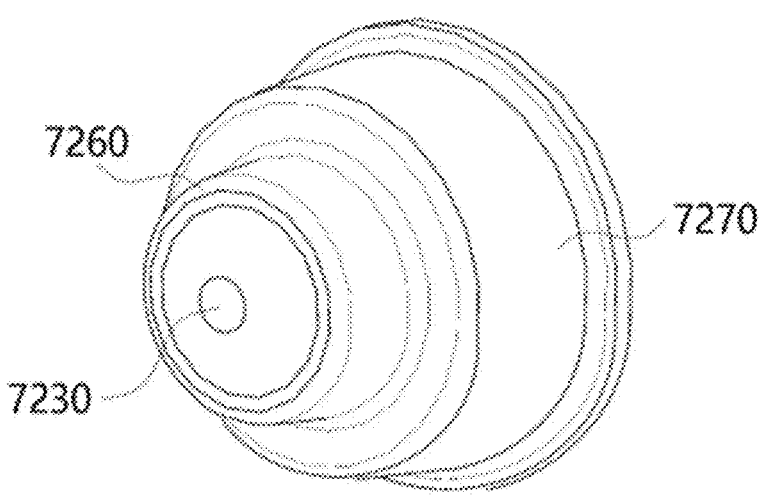
FIGS. 23A and 23B are perspective diagrams illustrating the cooling tip 7200 according to the 3-2 embodiment of the present application.
Figure 23B:
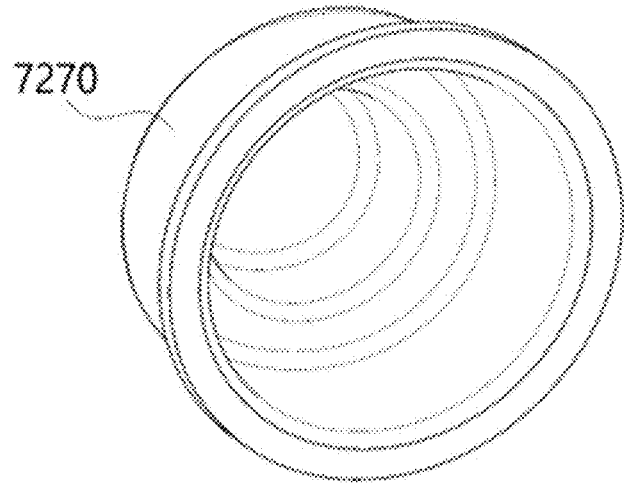
Figure 24A:
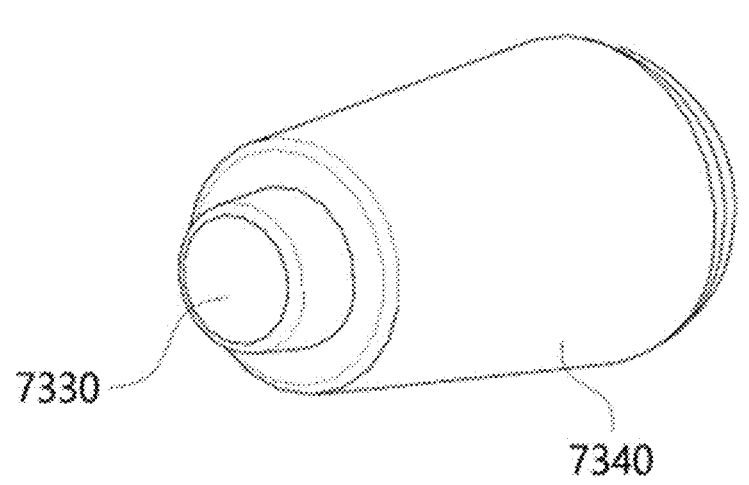
FIGS. 24A and 24B are perspective diagrams illustrating the cooling medium 7300 according to the 3-2 embodiment of the present application.
Figure 24B:
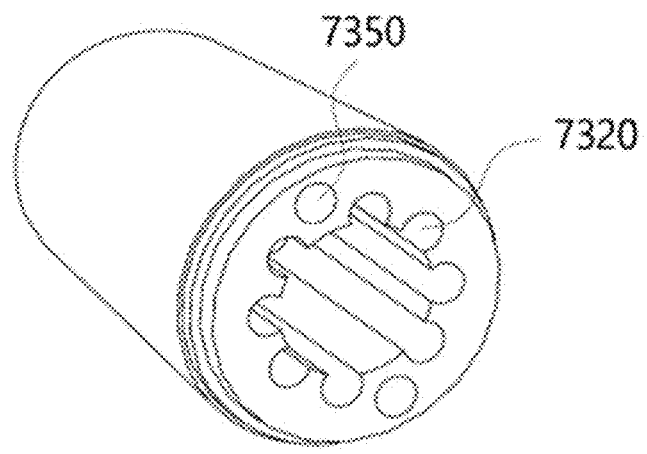

FIGS. 23A and 23B are diagrams illustrating the cooling tip 7200 according to the 3-2 embodiment of the present application. FIGS. 24A and 24B are diagrams illustrating the cooling medium 7300 according to the 3-2 embodiment of the present application.

Referring to FIGS. 23A, 23B, 24A and 24B together with FIGS. 19 to 22, the cooling tip 7200 may be cooled by the cooling medium 7300. More specifically, when the coolant that passed through the nozzle unit 7100 is cooled as the coolant passes through the cooling medium 7300, the cooling tip 7200 which is in direct physical contact with the cooling medium 7300 may be cooled due to receiving a flow of heat transmitted from the cooling medium 7300 by conduction. A spraying temperature regulating unit configured to control the temperature of the coolant being transferred to the cooling medium may be further included between the nozzle unit and the cooling medium. The spraying temperature regulating unit may be a Peltier element.

The cooling tip 7200 may include a first front end portion 7260 and a first rear end portion 7270. The first front end portion 7260 and the first rear end portion 7270 may each have a cylindrical shape a diameter/width/area that increases in a direction toward a rear end thereof. The first front end portion 7260 may be disposed at a front end of the first rear end portion 7270 and have an outer surface or outer circumferential surface whose diameter/width/area is smaller than that of the first rear end portion 7270. The first front end portion 7260 of the cooling tip 7200 may be integrally configured with the first rear end portion 7270. The first front end portion 7260 and the first rear end portion 7270 may be configured as an empty space to allow coupling to the cooling medium 7300.

The cooling medium 7300 may include a second front end portion 7330 and a second rear end portion 7340. The second front end portion 7330 and the second rear end portion 7340 may each have a cylindrical shape a diameter/width/area that increases in a direction toward a rear end thereof. The second front end portion 7330 may be disposed at a front end of the second rear end portion 7340 and have an outer surface or outer circumferential surface whose diameter/width/area is smaller than that of the second rear end portion 7340. The cooling medium 7300 may have a hollow to allow coupling to the nozzle guide unit 7150 which will be described below, and one or more coolant discharge paths 7320 may be formed along the circumference of the hollow around the hollow.

The second front end portion 7330 of the cooling medium 7300 may be inserted into and coupled to the first front end portion 7260 of the cooling tip 7200, and the second rear end portion 7340 of the cooling medium 7300 may be inserted into and coupled to the first rear end portion 7270 of the cooling tip 7200. Only a portion of the second rear end portion 7340 of the cooling medium 7300 may be inserted into and coupled to the first rear end portion 7270 of the cooling tip 7200.

A front surface of the first front end portion 7260 of the cooling tip 7200 may include a closed front surface as a place that comes in contact with the human body. The front surface of the cooling tip 7200 may serve as a marker. In this case, when the cooling tip 7200 comes in contact with an eye or the skin of a patient to cool or anesthetize the eye or skin of the patient, a mark corresponding to the front surface of the first front end portion 7260 may be formed on the body of the patient. The width/diameter of the front surface of the first front end portion 7260 may be 3 mm or more. Alternatively, the cooling tip 7200 may include a separate marker 7230 on the front surface of the first front end portion 7260. When the cooling tip 7200 comes in contact with an eye or the skin of a patient to cool or anesthetize the eye or skin of the patient, the marker 7230 may form a mark thereon. The marker 7230 has a front end protruding from the coolant contact portion to apply a pressure to the patient's body. The diameter of the marker 7230 may be about 3 mm or less.

The second front end portion 7330 of the cooling medium 7300 may include a closed front surface. The coolant that reached the cooling medium 7300 may be blocked by the second front end portion 7330 and not be able to reach the cooling tip 7200 and may exit the cooling device through the coolant discharge path 7320 formed at the second rear end portion 7340.

The cooling medium 7300 may be cooled by the coolant that passed through the nozzle unit 7100. The cooling medium 7300 may come in direct physical contact with the cooling tip 7200 and cool the cooling tip 7200.

The cooling medium 7300 may include a groove 7350 formed in the second rear end portion 7340. The cooling device may include a temperature sensor disposed in the groove 7350 of the cooling medium 7300. The cooling device should precisely control the temperature of the cooling device according to a method of treating a patient, and to this end, the cooling device should measure a temperature of a component coming in contact with an affected area of a patient or a temperature of a component adjacent the affected area. Although the cooling tip is a portion of the cooling device that comes in direct contact with an affected area of the human body, since the cooling tip 7200 is a component that is replaced after being used one time, installing a temperature sensor in the cooling tip 7200 is not efficient in terms of product design.

Therefore, it may be efficient to measure a temperature by installing a temperature sensor in the cooling medium 7300 that is disposed closest to the cooling tip 7200 and comes in contact therewith and that comes in direct contact with the cooling tip 7200 and transmits a flow of heat through coolant transfer. In this case, even when the temperature of the cooling tip 7200 is not measured directly, the temperature of the cooling tip 7200 may be estimated/controlled by measuring the temperature of the cooling medium 7300 and controlling the amount of coolant.

Here, before the cooling temperature of the cooling tip 7200 and the cooling medium 7300 reaches a normal state, in order to make a dynamic temperature change to occur within a predetermined range, the cooling tip 7200 and the cooling medium 7300 may have heat capacities within a predetermined ratio range. Also, materials of the cooling tip 7200 and the cooling medium 7300 may be selected to have heat capacities of the predetermined ratio. For example, the heat capacity of the cooling tip 7200 may be 0.1 to 5 times the heat capacity of the cooling medium 7300. When the heat capacity of the cooling tip 7200 is not equal to the heat capacity of the cooling medium 7300, an area in which the cooling tip 7200 and the cooling medium 7300 come in contact with each other may be increased or decreased to make a temperature response occur within a predetermined range. When the heat capacity of the cooling tip 7200 is lower than 0.1 times the heat capacity of the cooling medium 7300 or higher than 5 times the same, since a heat capacity difference between the cooling tip 7200 and the cooling medium 7300 is too large, it may not be easy to control the temperature by controlling the contact area between the cooling tip 7200 and the cooling medium 7300. In order to improve dynamic temperature responsiveness of the cooling medium 7300, the cooling medium 7300 may be thermally separated from other elements of the cooling device, and to this end, the cooling medium 7300 may be insulated from the other elements through the nozzle unit insulator 7400.

Figure 25:
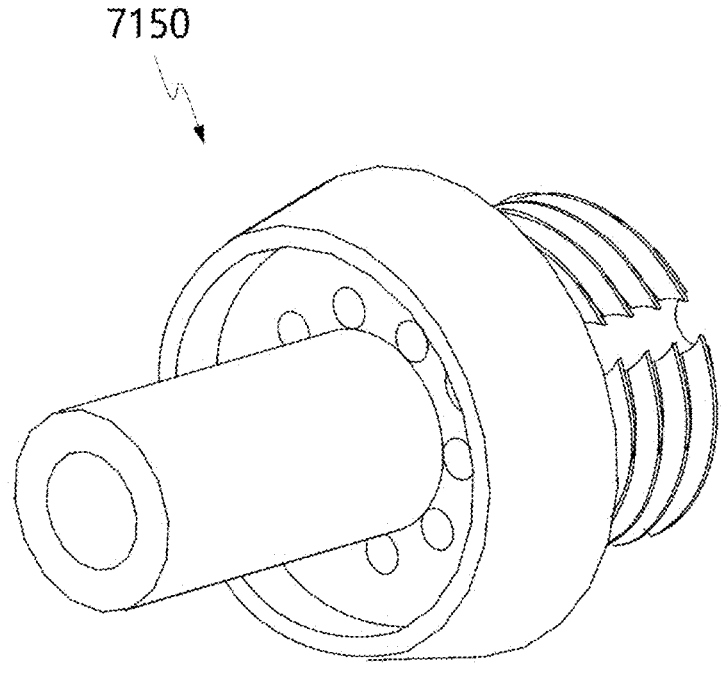
FIG. 25 is a disassembled diagram illustrating a nozzle guide unit 7150 according to the 3-2 embodiment of the present application.
Figure 26A:
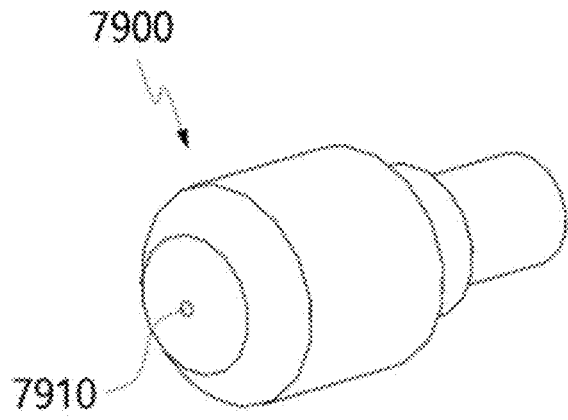
FIGS. 26A and 26B are perspective diagrams illustrating an orifice 7900 according to the 3-2 embodiment of the present disclosure.
Figure 26B:
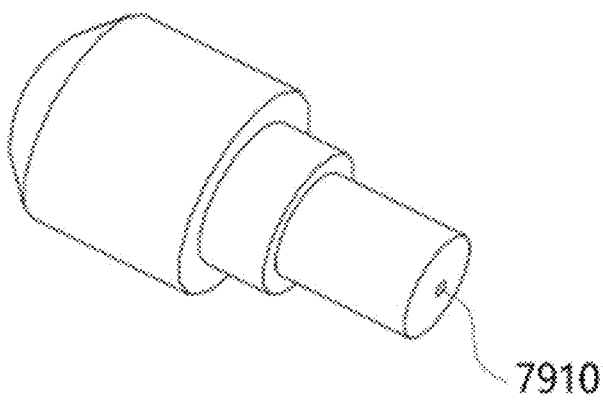

FIG. 25 is a view illustrating the nozzle guide unit 7150 according to the 3-2 embodiment of the present application. FIGS. 26A and 26B are diagrams illustrating the orifice 7900 according to the 3-2 embodiment of the present disclosure.

Referring to FIGS. 25, 26A and 26B together with FIGS. 19 to 22, the nozzle guide unit 7150 may serve to guide the cooling medium 7300 and the nozzle to be coupled at a correct position. The nozzle guide unit 7150 may induce coupling and alignment of the cooling medium and the nozzle unit 7100. Also, the nozzle guide unit 7150 may transmit an elastic force provided from the elastic coupling portion 7800 to the cooling medium 7300 to increase a coupling force between the cooling medium 7300 and the cooling tip 7200.

A front end of the nozzle guide unit 7150 may be inserted into and coupled to the second rear end portion 7340 of the cooling medium 7300. A rear end of the nozzle guide unit 7150 may be coupled to the nozzle unit insulator 7400 which will be described below.

The nozzle guide unit 7150 may be made of a metal having high thermal conductivity. Although cooling of the cooling medium 7300 is substantially performed by a coolant, the nozzle guide unit 7150 may also be cooled by the coolant to cool the cooling medium 7300. The cooling medium 7300 may be cooled by receiving a flow of heat by conduction and convection by the coolant and receiving a flow of heat by conduction by the nozzle guide unit 7150.

The nozzle guide unit 7150 may further include one or more coolant discharge holes through which the coolant discharged along the coolant discharge path 7320 of the cooling medium 7300 passes.

The nozzle guide unit 7150 may be selectively applied to the cooling device. That is, the nozzle unit 7100 may be coupled to the cooling medium 7300 without the nozzle guide unit 7150.

The orifice 7900 may be disposed at the front end of the nozzle unit 7100 to be coupled to the nozzle unit 7100. The orifice 7900 may be disposed between the nozzle unit 7100 and the nozzle guide unit 7150 to transfer a coolant to the cooling medium 7300 or the nozzle guide unit 7150. Also, when the orifice 7900 is coupled to the nozzle unit 7100 and the nozzle guide unit 7150, the front end of the orifice may be disposed to pass through the front end of the nozzle guide unit 7150 to transfer the coolant to the cooling medium 7300.

The diameter of the passage 7910 through which the coolant flows in the orifice 7900 may be less than the diameter of the first channel of the nozzle unit 7100.

The orifice 7900 may be integrally configured with the nozzle unit 7100. When the orifice 7900 is integrally configured with the nozzle unit 7100, as described above in relation to the nozzle unit 7100 according to the 3-1 embodiment, the diameter of the front end of the nozzle unit 7100 may be less than the diameter of the region of the nozzle unit 7100 excluding the front end thereof.

The orifice 7900 may be made of a metal having excellent wear resistance and pressure resistance. The orifice 7900 may be made of stainless steel.

The spraying unit 7000 according to the 3-2 embodiment of the present application may also include the nozzle unit insulator 7400, the insulator cover 7500, the front end cover 7600, the rear end cover 7700, and the elastic coupling portion 7800. The present embodiment has been illustrated as a configuration excluding the insulator cover 7500 as compared to the 3-1 embodiment, but the cooling device according to the present embodiment may further include the insulator cover 7500. Since the nozzle unit insulator 7400, the insulator cover 7500, the front end cover 7600, the rear end cover 7700, and the elastic coupling portion 7800 are the same as those described above in relation to the 3-1 embodiment, descriptions thereof will be omitted.

The cooling device 10000 according to the third embodiment of the present application has been disclosed above. However, the above description only discloses one specific embodiment intended to help in understanding, and thus the form of the cooling device 10000 disclosed by the present application is not limited to the cooling device 10000 according to the third embodiment that has been described above, and the scope of the present application should be determined on the basis of the claims below.

Hereinafter, operations that may be performed by the cooling device 10000 according to an embodiment of the present application will be disclosed in detail.

However, in describing specific operations of the cooling device 10000, for convenience of description, unless there is a specific limitation, the electronic valve 2100 that performs opening and closing in response to an electrical signal will be specified and described as the flow regulating unit 2000, the spraying temperature regulating unit 3100 that performs cooling and/or heating according to applied current to control the temperature of the coolant being sprayed will be specified and described as the coolant state regulating unit 3000, and the reservoir 1100 that is mounted on the cooling device 10000 to supply a coolant will be specified and described as the coolant supply unit 1000.

However, such an example of the cooling device 10000 is only described to prevent unnecessary redundant description, and of course, any other examples of the cooling device 10000 disclosed by the present application may be interpreted as being able to perform the following operations.

<Operations of Cooling Device 10000>

1. Cooling Control

The cooling device 10000 according to an embodiment of the present application may perform cooling of a target region TR.

For example, the cooling device 10000 may spray a coolant through the nozzle unit 4100 to perform cooling of the target region TR using the sprayed coolant. As another example, the cooling device 10000 may perform cooling of the target region TR in the form of cooling the cooling tip which comes in contact with the target region TR by spraying a coolant through the nozzle unit 4100 to the cooling tip and using the sprayed coolant.

The cooling device 10000 according to an embodiment of the present application may spray a coolant to perform cooling.

For example, the cooling device 10000 may perform cooling by causing the valve 2100 to be open for a predetermined amount of time. As a specific example, the cooling device 10000 may apply continuous current to the valve 2100. The control unit 5000 may transmit a signal for opening the valve 2100 to the valve 2100 and, when the predetermined amount of time elapses, may transmit a signal for closing the valve 2100 to the valve 2100. As another example, the cooling device 10000 may perform cooling by causing the valve 2100 to repeat opening and closing for a predetermined amount of time. As a specific example, the cooling device 10000 may apply current in the form of PWM to the valve 2100. The control unit 5000 may transmit a signal for opening the valve 2100 and a signal for closing the valve 2100 to the valve 2100 a predetermined number of times at predetermined intervals.

The cooling device 10000 according to an embodiment of the present application may control the amount of coolant being sprayed to control the cooling temperature of the target region TR. The cooling device 10000 according to an embodiment of the present application may control the opening and closing of the valve 210 to control the cooling temperature of the target region TR.

For example, the cooling device 10000 may control the opening/closing time and/or frequency of the valve to control the temperature of the target region TR. As a specific example, the cooling device 10000 may extend the opening time of the valve 2100 to control the temperature of the target region TR to be relatively lower. As another specific example, the cooling device 10000 may increase the frequency of opening the valve 2100 within a certain amount of time to control the temperature of the target region TR to be relatively lower.

The cooling device 10000 according to an embodiment of the present application may induce heat generation and/or heat absorption in the coolant being sprayed and control the cooling temperature of the target region TR.

For example, the cooling device 10000 may include the spraying temperature regulating unit 3100 configured to perform a heat exchange with the coolant being sprayed so as to induce heat generation and/or heat absorption in the coolant being sprayed and control the cooling temperature of the target region TR.

As a specific example, the control unit 5000 of the cooling device 10000 according to an embodiment of the present application may apply an electrical signal to the spraying temperature regulating unit 3100 to heat the coolant passing through the spraying temperature regulating unit 3100 so that the temperature of the coolant being sprayed is controlled be relatively higher. As a specific example, the control unit 5000 of the cooling device 10000 according to an embodiment of the present application may apply an electrical signal to the spraying temperature regulating unit 3100 to cool the coolant passing through the spraying temperature regulating unit 3100 so that the temperature of the coolant being sprayed is controlled be relatively lower.

The cooling device 10000 according to an embodiment of the present application may cool the temperature of the target region TR to a target cooling temperature when performing a cooling operation. The cooling device 10000 may cool the temperature of the target region TR to the target cooling temperature for a predetermined amount of time when performing a cooling operation. The cooling device 10000 may end the cooling operation after cooling the temperature of the target region TR to the target cooling temperature for the predetermined amount of time upon start of the cooling operation.

When starting the cooling operation, the cooling device 10000 according to an embodiment of the present application may be operated before cooling heat is applied to the target region TR. For example, when the cooling device 10000 performs a cooling operation in which the target cooling temperature is −15° C., upon start of the cooling operation, the temperature of the cooling tip may be controlled to reach −7° C. before the cooling tip is brought in contact with the target region TR, and when the temperature of the cooling tip reaches −7° C., a notification to bring the cooling tip in contact with the target region TR may be provided.

When ending the cooling operation, the cooling device 10000 according to an embodiment of the present application may cool the target region TR to a temperature higher than the target cooling temperature. For example, when the cooling device 10000 performs a cooling operation in which the target cooling temperature is −15° C., upon start of the cooling operation, the temperature of the target region TR may be maintained at −15° C. for a predetermined amount of time, and then, to detach between the cooling tip and the target region TR, the temperature of the cooling tip may be controlled to temporarily reach a temperature higher than −15° C. When the temperature of the cooling tip reaches a detaching temperature, the cooling device 10000 may provide a notification to separate the cooling tip from the target region TR.

2. Feedback Control According to Temperature

The cooling device 10000 according to an embodiment of the present application may perform feedback control according to temperature.

The cooling device 10000 may perform feedback control according to temperature in the form in which the temperature of the coolant being sprayed is controlled through the spraying temperature regulating unit 3100 on the basis of temperature. The cooling device 10000 may perform feedback control according to temperature in the form in which the amount of coolant being sprayed is controlled through the valve 2100 on the basis of temperature. As a specific example, the cooling device 10000 may control the spraying temperature regulating unit 3100 and the valve 2100 on the basis of the temperature of the target region TR in order to perform feedback control.

In the case of the cooling device 10000 that performs cooling using a coolant, performing feedback control according to temperature is very important. This is because, for example, in a case in which the cooling device 10000 is used to cool the human skin, when cooling is continuously performed despite a significant drop in the temperature of the target region TR, there may be a serious side effect in which skin necrosis occurs and skin restoration is not possible.

Therefore, the cooling device 10000 according to an embodiment of the present application may perform feedback control for the temperature of the target region TR that is directly/indirectly calculated.

The cooling device 10000 according to an embodiment of the present application may measure the temperature of the target region TR to perform feedback control according to temperature, may measure the temperature of the cooling tip coming in contact with the target region TR to perform feedback control according to temperature, may measure the temperature of the coolant being sprayed to perform feedback control according to temperature, or may calculate the temperature of the reservoir 1100 to perform feedback control according to temperature.

3. Cooling Mode Control According to Identification

The cooling device 10000 according to an embodiment of the present application may perform a function of identifying a component mounted on the cooling device 10000 to control a cooling mode. The cooling device 10000 according to an embodiment of the present application may perform a function of identifying a cooling label of a component mounted on the cooling device 10000 to control a cooling mode. Here, the identification of the cooling label may be performed by an identification sensor.

Here, the cooling label of the component may be an NFC tag included in the guide unit 4210. Here, an NFC reader may be included in one region of a contact surface of the cooling device 10000 that comes in contact with the guide unit 4210 when the guide unit 4210 is mounted. Alternatively, the cooling label of the component may be a barcode included in the cooling tip. Here, a barcode reader may be included in one region of a contact surface of the cooling device 10000 that comes in contact with the cooling tip when the cooling tip is mounted.

The cooling device 10000 according to an embodiment of the present application may determine a target cooling temperature for the target region TR on the basis of the identification of the cooling label.

For example, in a case in which a value identified by the identification sensor corresponds to a guide unit 4210 for necrosis, the control unit 5000 of the cooling device 10000 may determine the target cooling temperature of the target region TR as −40° C. and may operate to cool the target region TR to −40° C. In a case in which a value identified by the identification sensor corresponds to a cooling tip for anesthesia, the control unit 5000 of the cooling device 10000 may determine the target cooling temperature of the target region TR as −15° C. and may operate to cool the target region TR to −15° C.

The cooling device 10000 according to an embodiment of the present application may determine an extent to which the coolant is sprayed, on the basis of the identification of the cooling label.

For example, in a case in which a value identified by the identification sensor corresponds to a guide unit 4210 that should spray a coolant to a relatively wide area, the control unit 5000 of the cooling device 10000 may operate to spray a larger amount of coolant through the nozzle unit 4100 as compared to a case in which a value identified by the identification sensor corresponds to a guide unit 4210 that should spray a coolant to a narrow area. As a specific example, to allow a large amount of coolant to be sprayed through the nozzle unit 4100, the control unit 5000 of the cooling device 10000 may increase the number of times the valve 2100 is opened. As another specific example, to allow a large amount of coolant to be sprayed through the nozzle unit 4100, the control unit 5000 of the cooling device 10000 may extend the time during which the valve 2100 is open.

The cooling device 10000 according to an embodiment of the present application may determine a coolant spraying mode on the basis of the identification of the cooling label.

For example, in a case in which a value identified by the identification sensor corresponds to a cooling tip having a contact area for a target region TR having a relatively wide area, which is a cooling tip having a target cooling temperature of 10° C. to give a cooling sensation to the target region TR, the control unit 5000 of the cooling device 10000 may control the valve 2100 to repeat opening and closing. As another example, in a case in which a value identified by the identification sensor corresponds to a cooling tip having a contact area for a target region TR having a relatively narrow area, which is a cooling tip having a target cooling temperature of −40° C. to control a specific tissue in the target region TR, the control unit 5000 of the cooling device 10000 may control the valve 2100 to be open for a certain amount of time.

4. Provision of Radiant Energy

The cooling device 10000 according to an embodiment of the present application may perform a function of providing radiant energy to the target region TR and/or the periphery of the target region TR. For example, the cooling device 10000 may provide radiant energy to the target region TR and/or the periphery of the target region TR to provide heat. As another example, the cooling device 10000 may provide radiant energy to the target region TR and/or the periphery of the target region TR to mark a cooling region.

According to an embodiment of the present application, the cooling device 10000 may include a radiant energy provision unit 4230 configured to provide radiant energy to the target region TR and/or the periphery of the target region TR.

The radiant energy provision unit 4230 may provide radiant energy to a barrier of the target region TR. The radiant energy provision unit 4230 may provide radiant energy to the barrier of the target region TR to serve as a boundary heat providing unit configured to provide heat to the barrier of the target region TR. The radiant energy provision unit 4230 may perform a function of providing radiant energy to the periphery of the target region TR to allow a region other than the target region TR to have a relatively high temperature as compared to when radiant energy due to the radiant energy provision unit 4230 is not provided. In this way, the radiant energy provision unit 4230 may derive an effect of preventing supercooling of the region other than the target region TR when the cooling device 10000 performs cooling.

The radiant energy provision unit 4230 may provide radiant energy to the target region TR and a barrier of the target region TR. The radiant energy provision unit 4230 may perform a function of providing radiant energy to the target region TR and the periphery of the target region TR to allow a temperature of a region, in which an extent to which it is cooled is a predetermined cooling amount or less, to be relatively high as compared to when radiant energy due to the radiant energy provision unit 4230 is not provided. In this way, the radiant energy provision unit 4230 may derive an effect of preventing supercooling of the region other than the target region TR when the cooling device 10000 performs cooling.

5. Emergency Stop Control

The cooling device 10000 according to an embodiment of the present application may perform a function of stopping performance of a cooling operation in response to a specific event during performance of the cooling operation. For example, when an input for emergency stop is detected through the input sensor 6300 during performance of a cooling operation, the cooling device 10000 may close the valve 2100 to stop spraying of a coolant that was being performed.

Generally, the cooling device 10000 performing a cooling operation is implemented to perform a cooling operation for a predetermined amount of time upon start of the cooling operation and then end the cooling operation. However, in a case in which the cooling device 10000 performs cooling on the living body as the target region TR, it may be necessary to arbitrarily end the cooling operation at the discretion of a more specialized operator. For example, in a case in which the temperature of the target region TR is sharply decreased excessively or a subject receiving treatment complains of excessive pain, there may be an urgent need to end the cooling operation regardless of whether a predetermined amount of time has elapsed after the start of the cooling operation.

The cooling device 10000 according to an embodiment of the present application may perform an emergency stop function to address the above-described problems.

According to an embodiment of the present application, the cooling device 10000 may perform an operation for ending the cooling operation in a case in which an input for emergency stop is detected.

For example, in a case in which an input for emergency stop is detected, the cooling device 10000 may transmit a signal for closing the valve 2100 to the valve 2100. As a specific example, in a case in which an input for emergency stop is detected, even when a coolant is being sprayed through the nozzle unit 4100, the cooling device 10000 may transmit a signal for closing the valve 2100 to the valve 2100 to end the spraying of the coolant through the nozzle unit 4100.

As another example, in a case in which an input for emergency stop is detected, the cooling device 10000 may slightly increase the temperature of the target region TR as compared to the temperature right before ending the cooling operation. As a specific example, in a case in which an input for emergency stop is detected, the cooling device 10000 may, even when the target region TR is being cooled through the cooling tip, transmit a signal for closing the valve to the valve so that spraying of the coolant to the cooling tip is stopped and the cooling tip reaches a detaching temperature. As another specific example, in a case in which an input for emergency stop is detected, the cooling device 10000 may, even when a coolant is being sprayed through the nozzle unit 4100, control the spraying temperature regulating unit 3100 and the valve 2100 so that the coolant heated to the detaching temperature is sprayed through the nozzle unit 4100 for a certain amount of time.

The cooling device 10000 according to an embodiment of the present application may detect an input for emergency stop. The input for emergency stop may have various forms. For example, a plurality of input sensors 6300 may be provided in the cooling device 10000. One input sensor 6300 may detect an input for starting a cooling operation of the cooling device 10000, and the other input sensor 6300 may detect an input for arbitrary stop (that is, emergency stop) of the cooling operation of the cooling device 10000. As another example, a single input sensor 6300 may be provided in the cooling device 10000. The cooling device 10000 may distinguish an input on the basis of a timing and/or duration of a user input detected through the single input sensor 6300.

As a specific example, when a user input is detected through the single input sensor 6300, the cooling device 10000 may perform a cooling operation. In a case in which the cooling device 10000 is confirmed as already performing the cooling operation when a user input is detected through the single input sensor 6300, the cooling device 10000 may end the cooling operation.

As another specific example, in a case in which a user input detected through the single input sensor 6300 is continued during a first time, the cooling device 10000 may perform a cooling operation. Here, in a case in which a user input is detected through the single input sensor 6300 but is not continued during the first time, the cooling device 10000 may not perform the cooling operation. In a case in which a user input detected through the single input sensor 6300 is continued during a second time, the cooling device 10000 may end the cooling operation. In the case in which the user input detected through the single input sensor 6300 is continued during the second time, even in the middle of the cooling operation of the cooling device 10000, the cooling device 10000 may end the cooling operation. The first time and the second time may be different.

6. Induction of Psychological Stability

The cooling device 10000 according to an embodiment of the present application may perform a function of reducing emotions such as boredom and fear that a subject receiving treatment may feel while the cooling operation is performed. The cooling device 10000 may perform a function of inducing psychological stability of the subject receiving treatment.

According to an embodiment of the present application, the cooling device 10000 may perform a function of providing a rhythm and/or music to which a user may listen during a cooling operation so as to perform a function of inducing psychological stability of the subject receiving treatment.

In other words, in a case in which cooling is performed on the target region TR, the subject receiving treatment may feel some pain due to cooling the target region TR or feel boredom during the time taken for the cooling operation. To address this, the cooling device 10000 according to the present application may allow the subject receiving treatment to perceive a rhythm and/or music during the cooling operation.

For example, the cooling device 10000 may include an output unit configured to output sound and may perform a function of providing music to the subject receiving treatment through the output unit. As another example, the cooling device 10000 may perform a function of providing a rhythm caused by at least one of a coolant releasing sound and a valve 2100 closing sound, which are generated as the valve 2100 repeats opening and closing, to the subject receiving treatment.

According to an embodiment of the present application, the cooling device 10000 may repeatedly control the opening and closing of the valve 2100 to provide a rhythm to a subject receiving treatment.

For example, the control unit 5000 may control the opening of the valve 2100 so that the opening of the valve 2100 corresponds to a specific rhythm. As a specific example, the control unit 5000 may open the valve 2100 in a rhythm consisting of one quarter-note beat, one quarter-note beat, one quarter-note beat, one quarter-note beat, one quarter-note beat, one quarter-note beat, and one half-note beat so as to correspond to the "twinkle twinkle little star" part of the Twinkle Twinkle Little Star song. Here, the control unit 5000 may control the valve 2100 to be closed when a predetermined amount of time elapses after the valve 2100 is opened. Here, the predetermined amount of time (that is, the time taken until the valve 2100 is closed after the valve 2100 is opened) may be shorter than one quarter-note beat.

According to an embodiment of the present application, the cooling device 10000 may provide music corresponding to a frequency of opening of the valve 2100.

For example, the cooling device 10000 may provide fast-tempo music in a case in which the valve 2100 is opened and closed according to short time intervals and may provide slow-tempo music in a case in which the valve 2100 is opened and closed according to long time intervals. As another example, in a case in which the valve 2100 of the cooling device 10000 is opened to correspond to the Twinkle Twinkle Little Star song, the cooling device 10000 may play the song through the output unit.

In the cooling device 10000 according to an embodiment of the present application, target cooling temperatures and/or methods of controlling the valve 2100 may vary according to effects to be derived by cooling (e.g., anesthesia, tumor removal, skin lightening, etc.), and music and/or rhythms provided to a subject receiving treatment may vary according to the target cooling temperature and/or method of controlling the valve 2100.

7. Driving Control According to Gas Concentration

The cooling device 10000 according to an embodiment of the present application may perform a function of detecting a concentration of a gas in an environment in which the cooling device 10000 is used. The cooling device 10000 according to an embodiment of the present application may perform a function of checking a concentration of a gas that flows out due to use of the cooling device 10000. Here, the concentration of the gas flowing out may be checked by a gas sensor.

According to an embodiment of the present application, a gas sensor may measure a gas concentration while the control unit 5000 controls the valve 2100 to perform a cooling operation. For example, the gas sensor may measure a gas concentration while the valve 2100 is open. As another example, the gas sensor may measure a gas concentration while the valve 2100 repeats opening and closing.

The cooling device 10000 according to an embodiment of the present application may provide a notification when a concentration of a specific gas in an environment in which the cooling device 10000 is used is a predetermined numerical value or higher. For example, in a case in which the cooling device 10000 uses $CO_2$ as a coolant and the gas sensor measures the $CO_2$ concentration, the cooling device 10000 may provide a notification to an operator and/or a subject receiving treatment through a display or a speaker when the measured $CO_2$ concentration exceeds a reference value.

The cooling device 10000 according to an embodiment of the present application may end performance of the cooling operation when a concentration of a specific gas in an environment in which the cooling device 10000 is used is a predetermined numerical value or higher. For example, in a case in which the cooling device 10000 sprays $CO_2$ when performing a cooling operation, the gas sensor may continuously monitor the CO2 concentration and may, when the measured $CO_2$ concentration exceeds a reference value, perform a procedure for arbitrarily ending the cooling operation even when the cooling operation is not ended.

A gas sensor according to another embodiment of the present application may be disposed outside the cooling device 10000. For example, in a case in which a cradle for charging the cooling device 10000 is provided, the gas sensor may be provided in the cradle, and here, a notification may be provided on the basis of a gas concentration of the gas sensor.

Some operations that may be performed by the cooling device 10000 according to an embodiment of the present application have been disclosed above. However, the operations disclosed above are merely some typical operations that may be performed by the cooling device 10000 according to an embodiment of the present application, and operations that may be performed by the cooling device 10000 according to the present application are not limited to the operations described above.

Hereinafter, in performing a cooling operation by the cooling device 10000 according to an embodiment of the present application, the configuration and operation of the cooling device 10000 that directly sprays a coolant to a target region TR will be described in more detail.

However, the following description will be given by assuming that the cooling device 10000 includes the reservoir receiving unit 1300, the valve 2100, the nozzle unit 4100, and the control unit 5000 unless stated otherwise.

However, this is merely an example of the cooling device 10000 that is described to prevent unnecessary redundant description, and of course, any other examples of the cooling device 10000 disclosed by the present application may be implemented as a type that directly sprays a coolant to a target region TR and may perform various operations disclosed by the present specification.

<Type of Cooling Device 10000 that Sprays Coolant>

1. Configuration

Figure 27:
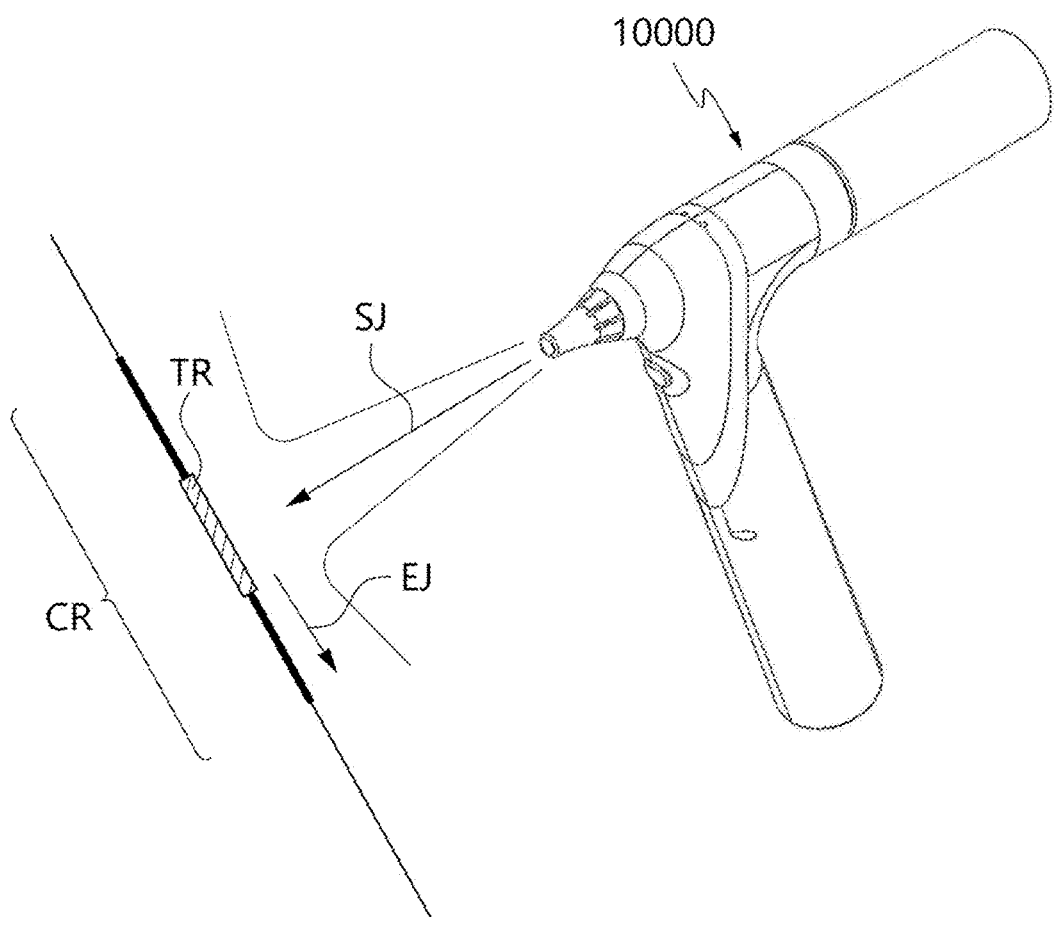
FIG. 27 is a diagram for describing a cooling operation of the cooling device 10000 according to an embodiment of the present application.

FIG. 27 is a diagram for describing a cooling operation of the cooling device 10000 according to an embodiment of the present application.

According to an embodiment of the present application, the cooling device 10000 may spray a coolant through the nozzle unit 4100. The coolant that passed through the nozzle unit 4100 may be sprayed to at least a target region TR, and the target region TR may perform a heat exchange with at least a portion of the sprayed coolant by conduction.

In a case in which the cooling device 10000 according to an embodiment of the present application sprays a coolant to a target region TR, the coolant may be sprayed in the form of a free jet FJ in which the coolant is sprayed in a direction toward the target region TR and may be sprayed in the form of a spread jet SJ in which the coolant collides with a subject to be treated, which includes the target region TR, and is emitted in a different direction from the spraying direction.

Due to the free jet FJ and/or spread jet SJ generated due to the cooling device 10000 spraying the coolant to the target region TR, a cooling region CR may be formed on a subject to be treated.

Here, the cooling region CR may be a region in which the temperature is relatively lowered in the subject to be treated that is formed due to conduction and/or convection with the free jet FJ and/or spread jet SJ.

The target region TR may be included in the cooling region CR. For example, the cooling region CR may coincide with the target region TR. As another example, the target region TR may belong to the cooling region CR.

The cooling device 10000 according to an embodiment of the present application may cool a subject to be treated including the target region TR so that the cooling region CR includes a first temperature section formed by the free jet FJ and a second temperature section formed by the spread jet SJ. For example, an operator who performs cooling using the cooling device 10000 may drive the cooling device 10000 so that the target region TR belongs to the first temperature section. In order to make the target region TR belong to the first temperature section, an angle at which a coolant is jetted through the nozzle unit 4100 and a distance between the cooling device 10000 and the target region TR may be controlled. Here, an average temperature of the first temperature section may be lower than an average temperature of the second temperature section.

According to an embodiment of the present application, the cooling device 10000 may include a straight nozzle-type nozzle unit 4100.

Figure 28:
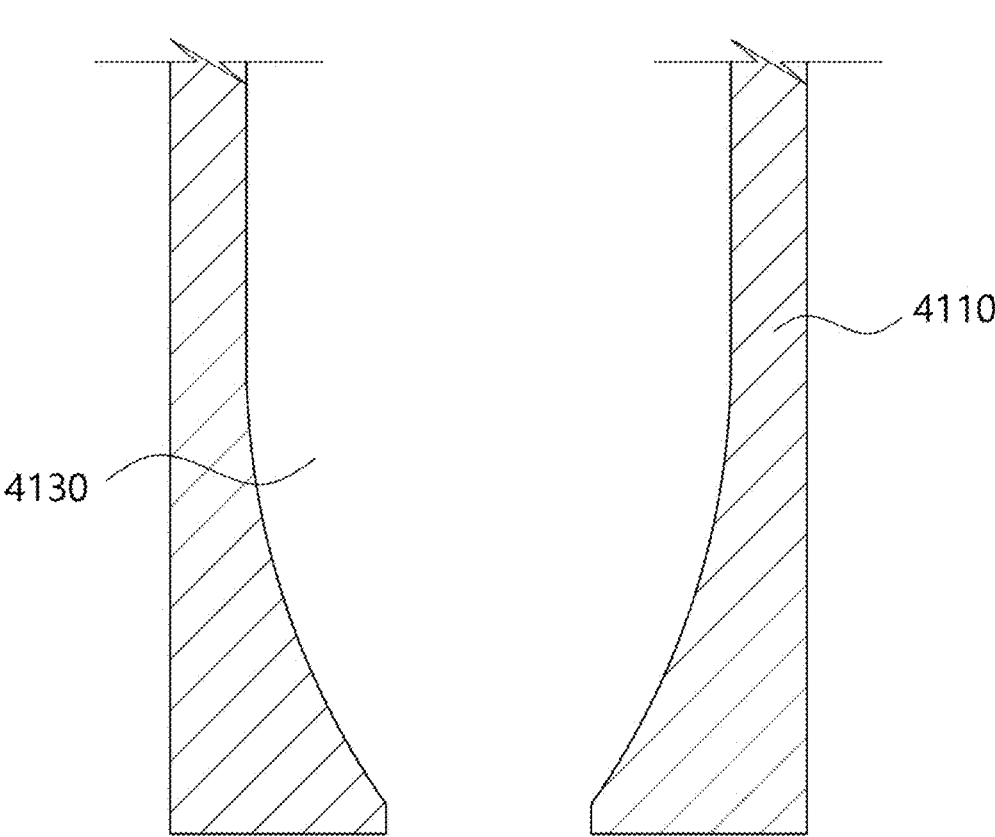
FIG. 28 is a diagram for describing the shape of a nozzle unit 4100 according to an embodiment of the present application.

FIG. 28 is a diagram for describing the shape of the nozzle unit 4100 according to an embodiment of the present application.

FIG. 28 illustrates a longitudinal cross-section of the nozzle unit 4100, and the nozzle unit 4100 according to the present embodiment may include a nozzle rod 4110 and a jetting hole 4130.

The nozzle rod 4110 may have a cylindrical exterior. The nozzle rod 4110 may include the jetting hole 4130 to allow a coolant to pass therethrough.

The jetting hole 4130 may have the same cross-sectional area in the longitudinal direction of the nozzle rod 4110. The jetting hole 4130 may be a hollow formed in a cylindrical shape. However, a cross-sectional area of the jetting hole 4130 at an outer side of the nozzle rod 4110 may be narrower than a cross-sectional area of the jetting hole 4130 at the center of the nozzle rod 4110. This is to increase a pressure of the coolant sprayed through the jetting hole 4130 to allow the coolant to be jetted to the outside of the cooling device 10000 through the jetting hole 4130 due to a phenomenon in which pressure energy is changed into speed energy.

In a case in which the cooling device 10000 including the straight nozzle-type nozzle unit 4100 performs cooling, a temperature may be relatively low at the central portion of the cooling region CR, a temperature may be relatively high at the periphery of the cooling region CR, and a temperature distribution in the form of a single Gaussian distribution may be formed in the cooling region CR.

Here, "the form of a single Gaussian distribution" may refer to a temperature gradient formed as a temperature distribution curve relating to a region is vertically symmetrical with respect to the lowest temperature point.

According to an embodiment of the present application, the cooling device 10000 may include an annular nozzle-type nozzle unit 4100.

Figure 29:
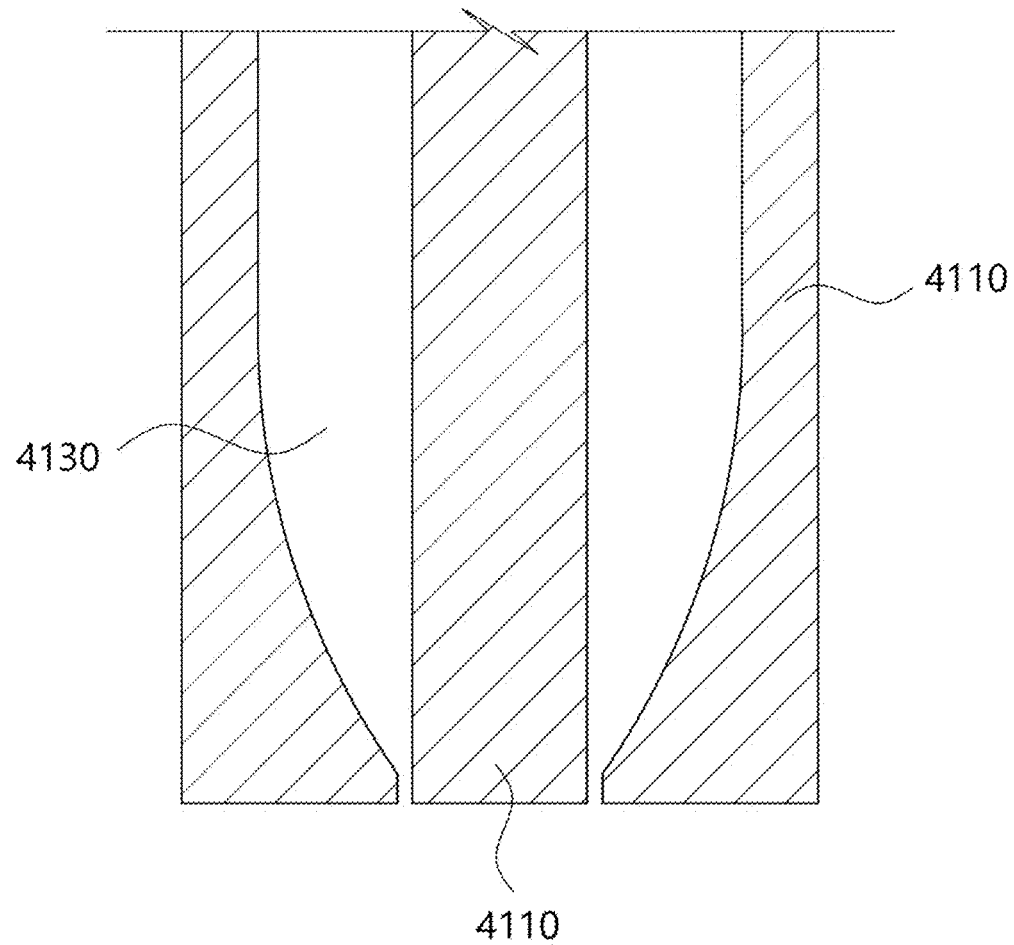
FIG. 29 is a diagram for describing the shape of a nozzle unit 4100 according to another embodiment of the present application.

FIG. 29 is a diagram for describing the shape of the nozzle unit 4100 according to another embodiment of the present application.

FIG. 29 illustrates a longitudinal cross-section of the nozzle unit 4100, and the nozzle unit 4100 according to the present embodiment may include a nozzle rod 4110 and a jetting hole 4130.

The nozzle rod 4110 may have a cylindrical exterior. The nozzle rod 4110 may include the jetting hole 4130 to allow a coolant to pass therethrough.

The jetting hole 4130 may have the same cross-sectional area in the longitudinal direction of the nozzle rod 4110. The jetting hole 4130 may be a hollow formed in a ring shape with respect to an outer side surface of the nozzle rod 4110. In other words, the jetting hole 4130 may be a hollow formed in a shape in which one ring-shaped surface extends in the longitudinal direction of the nozzle rod 4110 with respect to the outer side surface of the nozzle rod 4110.

As in the previous embodiment, a cross-sectional area of the jetting hole 4130 at an outer side of the nozzle rod 4110 may be narrower than a cross-sectional area of the jetting hole 4130 at the center of the nozzle rod 4110. This is to increase a pressure of the coolant sprayed through the jetting hole 4130 to allow the coolant to be jetted to the outside of the cooling device 10000 through the jetting hole 4130 due to a phenomenon in which pressure energy is changed into speed energy.

In a case in which the cooling device 10000 including the annular nozzle-type nozzle unit 4100 performs cooling, a temperature may be relatively low at the central portion of the cooling region CR, a temperature may be relatively high at the periphery of the cooling region CR, and a temperature distribution in the form of a model in which a plurality of Gaussian distributions are mixed may be formed in the cooling region CR.

Here, "the form of a model in which a plurality of Gaussian distributions are mixed" may refer to a temperature distribution formed by combination of a first virtual Gaussian distribution, in which a temperature gradient is formed as a temperature distribution curve relating to a region is vertically symmetrical with respect to a relatively low temperature point, and a second virtual Gaussian distribution, in which a temperature gradient is formed as a temperature distribution curve relating to a region is vertically symmetrical with respect to a relatively low temperature point.

According to an embodiment of the present application, in a case in which the cooling device 10000 including the annular nozzle-type nozzle unit 4100 performs cooling, an effect of performing uniform cooling may be derived as compared to a case in which the cooling device 10000 including the straight nozzle-type nozzle unit 4100 performs cooling.

For example, in a case in which the cooling device 10000 including the annular nozzle-type nozzle unit 4100 performs cooling, a temperature distribution in the first temperature section of the cooling region CR may be relatively more uniform as compared to a case in which the cooling device 10000 including the straight nozzle-type nozzle unit 4100 performs cooling. In this case, it may be assumed that a cross-sectional area of a jetting hole of the annular nozzle-type nozzle unit 4100 is the same as a cross-sectional area of a jetting hole of the straight nozzle-type nozzle unit 4100.

The nozzle unit 4100 according to an embodiment of the present application may be in the shape of a bell nozzle. The nozzle unit 4100 according to another embodiment of the present application may be in the shape of an aerospike nozzle. The nozzle unit 4100 according to another embodiment of the present application may be in the shape in which shapes of a bell nozzle and an aerospike nozzle are combined.

Figure 30:
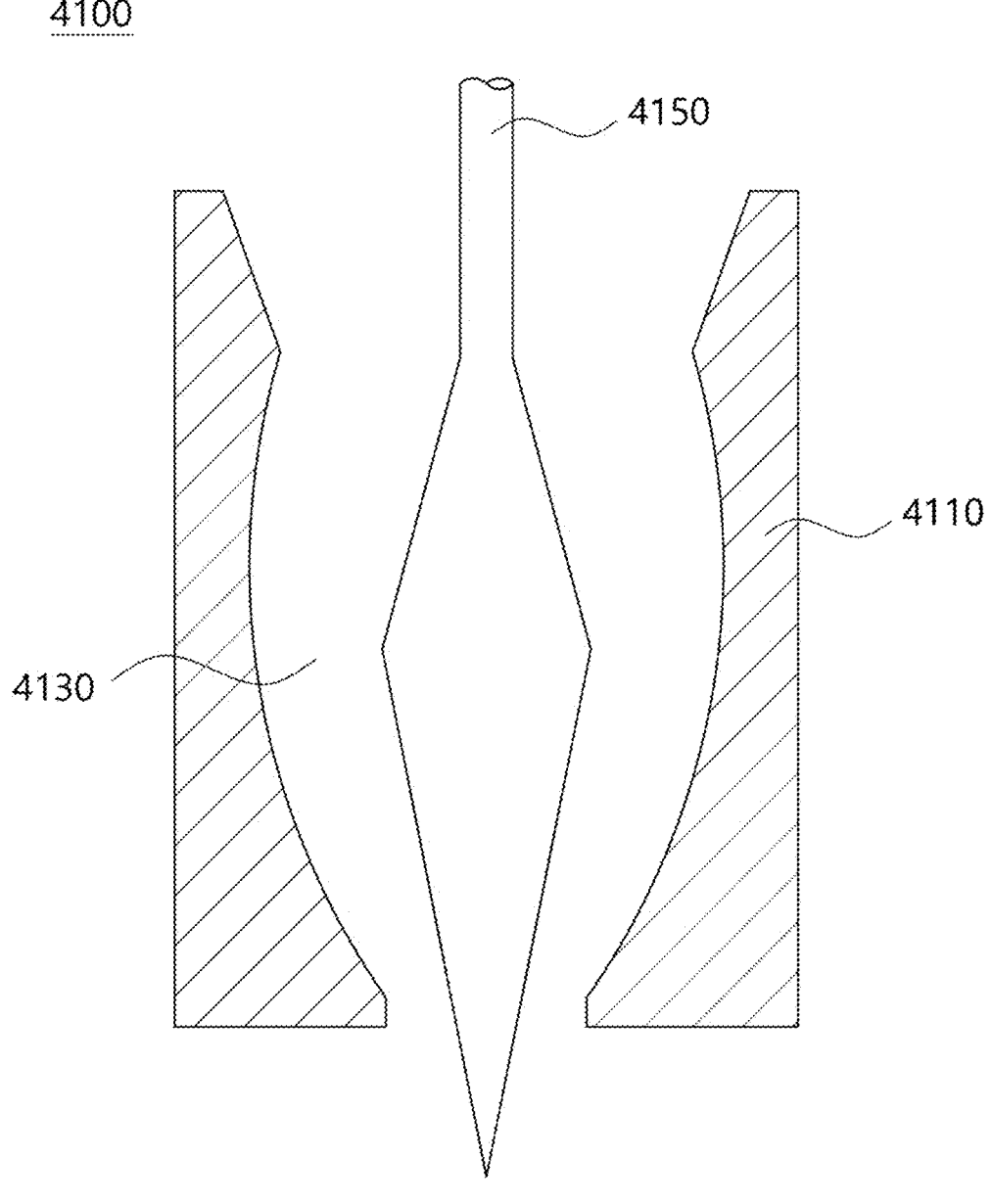
FIG. 30 is a diagram for describing the shape of a nozzle unit 4100 according to still another embodiment of the present application.

FIG. 30 is a diagram for describing the shape of the nozzle unit 4100 according to still another embodiment of the present application.

FIG. 30 illustrates a longitudinal cross-section of the nozzle unit 4100, and the nozzle unit 4100 according to the present embodiment may include a nozzle rod 4110, a jetting hole 4130, and an aero-fin 4150.

The nozzle rod 4110 may have a cylindrical exterior. The nozzle rod 4110 may include the jetting hole 4130 to allow a coolant to pass therethrough.

The jetting hole 4130 may have a cross-sectional area that varies in the longitudinal direction of the nozzle rod 4110.

For example, a cross-sectional area of the jetting hole 4130 at one end of the nozzle unit 4110 that is most spaced apart from the cooling device 10000 may be smaller than a cross-sectional area of the jetting hole 4130 at the center of the nozzle unit 4110 in the longitudinal direction. As another example, the cross-sectional area of the jetting hole 4130 may tend to increase in a direction toward one end of the nozzle unit 4110 that is most spaced apart from the cooling device 10000. As still another example, the cross-sectional area of the jetting hole 4130 may tend to decrease in a direction toward one end of the nozzle unit 4110 that is most spaced apart from the cooling device 10000.

The aero-fin 4150 may be disposed in the jetting hole 4130. The aero-fin 4150 may be at least one fin including a sharp shape that becomes thin in a direction toward one end. The sharp fin of the aero-fin 4150 may be disposed toward one end of the jetting hole 4130 that is most spaced apart from the cooling device 10000.

The cooling device 10000 may spray a coolant to a target region TR through the jetting hole 4130. The size of the cooling region CR due to the cooling device 10000 may be determined on the basis of the shape, size, or the like of the jetting hole 4130 and/or the aero-fin 4150.

The cooling device 10000 according to an embodiment of the present application may include the aero-fin 4150 configured to move in the longitudinal direction of the nozzle rod 4110. For example, the cooling device 10000 may include an aero-fin 4150 controlled to move using at least one of physical, electrical, and/or mechanical external forces.

As a specific example, the aero-fin 4150 may include a material having magnetism, and the nozzle rod 4110 or one region of the cooling device 10000 on which the nozzle rod 4110 is mounted may include a region in which a magnetic field may be formed. The region in which a magnetic field may be formed may have a form in which a magnetic body is wrapped with a coil, and the control unit 5000 configured to control the region in which a magnetic field may be formed may change a direction of current flowing in the coil to control movement of the aero-fin 4150 in the longitudinal direction of the nozzle rod 4110.

Figure 31:
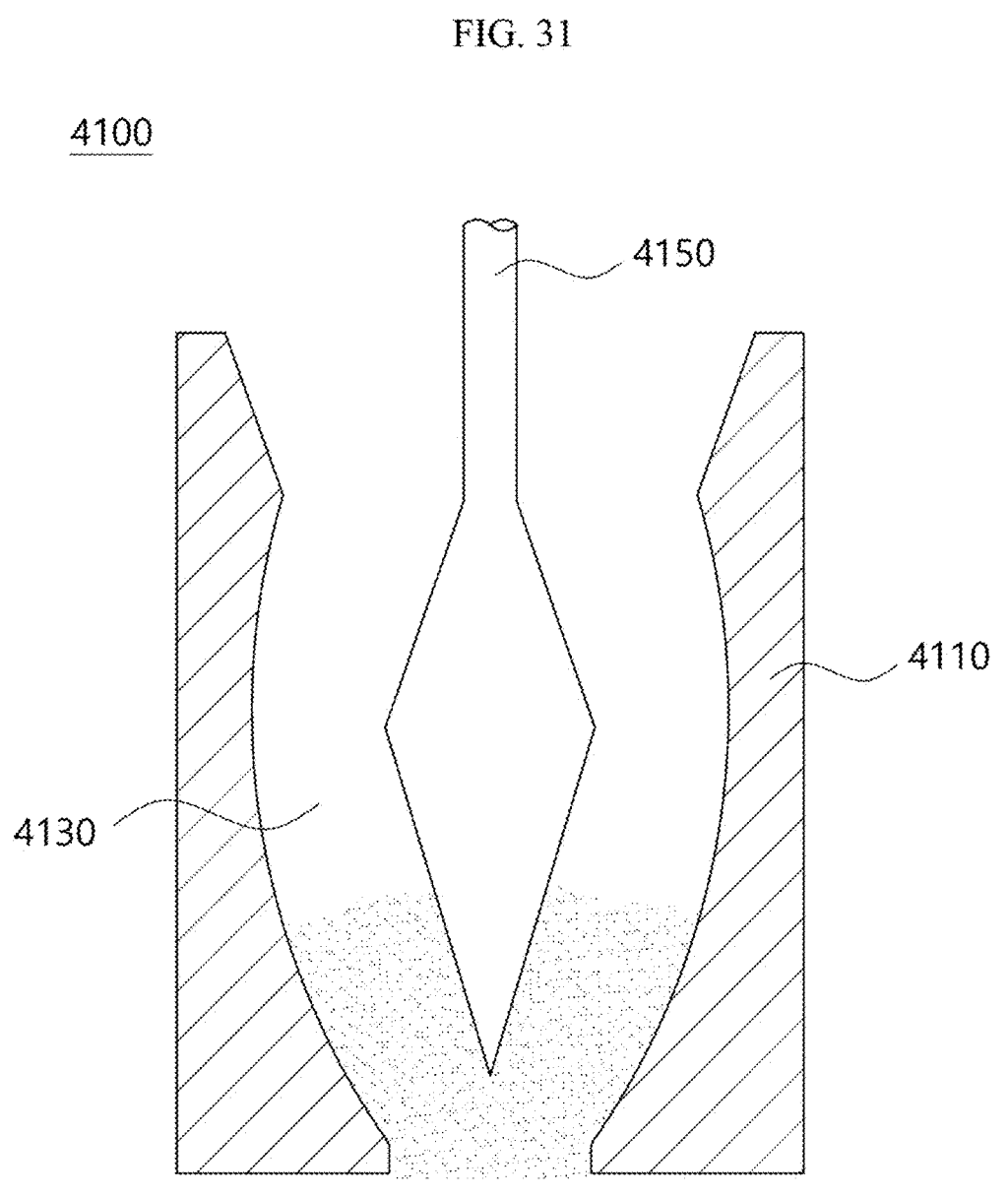
Figure 32:
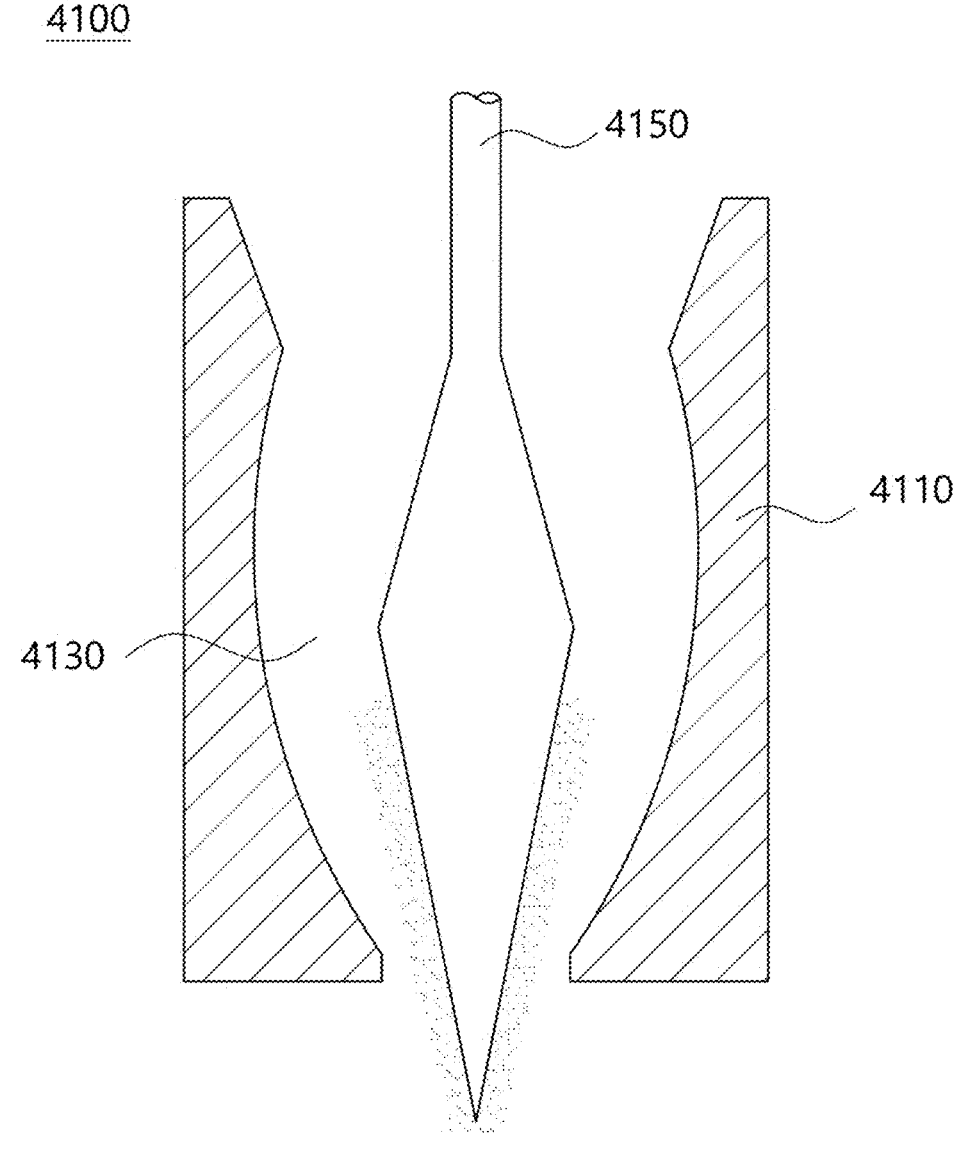

FIGS. 31 and 32 are diagrams for describing changes in a coolant spraying region according to movement of the aero-fin 4150 in the nozzle unit 4100 according to an embodiment of the present application.

FIG. 31 illustrates a case in which the nozzle unit 4100 according to an embodiment of the present application is in a first state in which the aero-fin 4150 is not exposed to the outside of one end of the nozzle rod 4110.

In a case in which the aero-fin 4150 is not exposed to the outside of one end of the nozzle rod 4110, a coolant spraying region may be determined on the basis of a cross-sectional area of the jetting hole 4130 at one end of the nozzle rod 4110 that is most spaced apart from the cooling device 10000.

The cooling device 10000 according to an embodiment of the present application may spray a coolant in a form of being emitted on the basis of the cross-sectional area of the jetting hole 4130 at the one end most spaced apart from the cooling device 10000 in the first state.

FIG. 32 illustrates a case in which the nozzle unit 4100 according to an embodiment of the present application is in a second state in which the aero-fin 4150 is exposed to the outside of one end of the nozzle rod 4110.

In a case in which the aero-fin 4150 is exposed to the outside of one end of the nozzle rod 4110, a coolant spraying region may be determined on the basis of a cross-sectional area of an outer diameter of a sharp fin of the aero-fin 4150.

The cooling device 10000 according to an embodiment of the present application may spray a coolant along an outer surface of the aero-fin 4150 in the second state.

In a case in which the cooling device 10000 is used in cooling the target region TR, the size of the cooling region CR may be relatively smaller when a coolant is sprayed in the second state as compared to when a coolant is sprayed in the first state. In this way, in the case of the cooling device 10000 which performs cooling using the nozzle unit 4100 including the aero-fin 4150 or the nozzle unit 4100 including the aero-fin 4150 moving in the longitudinal direction of the nozzle rod 4110, an effect of allowing more intensive spraying of a coolant to the center of the cooling region CR may be derived.

The nozzle unit 4100 according to an embodiment of the present application and forms of spraying a coolant using the same have been disclosed above. However, the above-described embodiments only disclose specific embodiments intended to help in understanding, and thus the nozzle unit 4100 according to the present application is not limited to the above-described forms.

According to an embodiment of the present application, the cooling device 10000 may have a guide unit 4210 mounted thereon to limit a spraying range of a coolant sprayed through the nozzle unit 4100.

According to an embodiment of the present application, the guide unit 4210 may be implemented with a material and/or shape suitable for the shape of a subject to be treated on which cooling will be performed by the cooling device 10000.

For example, the guide unit 4210 may be made of a material having an elastic force. As a specific example, the guide unit 4210 may be made of rubber.

According to an embodiment of the present application, in a case in which the cooling device 10000 includes the guide unit 4210 having an elastic force, it is possible to derive an effect of minimizing loss of a gas that occurs on a contact surface between the guide unit 4210 and the subject to be treated when the cooling device 10000 comes in contact with the subject to be treated, which includes the target region TR, to cool the target region TR. In a case in which cooling is performed using the cooling device 10000 including the guide unit 4210 having an elastic force as described above, since the coolant discharged to an inner space of the guide unit 4210 may stay on the target region TR for a relatively long period of time, it is possible to derive effects of preventing unnecessary loss of coolant and increasing cooling efficiency for a certain amount of coolant.

According to an embodiment of the present application, in a case in which the cooling device 10000 includes the guide unit 4210 having an elastic force, it is possible to derive an effect of preventing damage to the target region TR when the cooling device 10000 comes in contact with the subject to be treated, which includes the target region TR, to cool the target region TR. As a specific example, in a case in which the cooling device 10000 sprays a coolant to an eye to perform cooling so that a degree of neural activation in the target region TR is temporarily reduced, the guide unit 4210 of the cooling device 10000 may come in contact with the eye at a time point at which a coolant is sprayed through the nozzle unit 4100. Here, since the guide unit 4210 has an elastic force of a predetermined numerical value or more, it is possible to derive an effect of preventing damage to the eye due to the contact.

The guide unit 4210 according to an embodiment of the present application may include a periphery hole 4211. The periphery hole 4211 may be implemented to have a suitable position and/or shape to prevent the coolant flowing out through the periphery hole 4211 from flowing out to a surface of a subject to be treated on which cooling will be performed by the cooling device 10000. As a specific example, in a case in which the cooling device 10000 sprays a coolant to an eye to perform cooling so that a degree of neural activation in the target region TR is temporarily reduced, the guide unit 4210 of the cooling device 10000 may have the periphery hole 4211, and the periphery hole 4211 may be formed in one direction in the guide unit 4210 to prevent the coolant discharged through the periphery hole 4211 from coming in contact with the subject to be treated which includes the target region TR.

In a case in which the guide unit 4210 according to an embodiment of the present application has an elastic force, a length of the guide unit 4210 when the guide unit 4210 comes in contact with the subject to be treated which includes the target region TR may be determined according to the elastic force of the guide unit 4210. For example, the guide unit 4210 may have a shape extending in a first direction, and a first length of the guide unit 4210 in the first direction before the guide unit 4210 comes in contact with the target region TR may be longer than a second length of the guide unit 4210 in the first direction after the guide unit 4210 comes in contact with the target region TR. The first direction may be a direction in which the guide unit 4210 is mounted on the cooling device 10000. Therefore, in a case in which the guide unit 4210 has an elastic force, the amount of coolant sprayed by the cooling device 10000 may be set to be appropriately controlled in consideration of the length of the guide unit 4210 when the guide unit 4210 comes in contact with the subject to be treated which includes the target region TR.

As another example, the guide unit 4210 may be implemented in an asymmetrical shape. As a specific example, an end surface of the guide unit 4210 that comes in contact with the subject to be treated which includes the target region TR may be formed in a diagonal shape.

Figure 33:
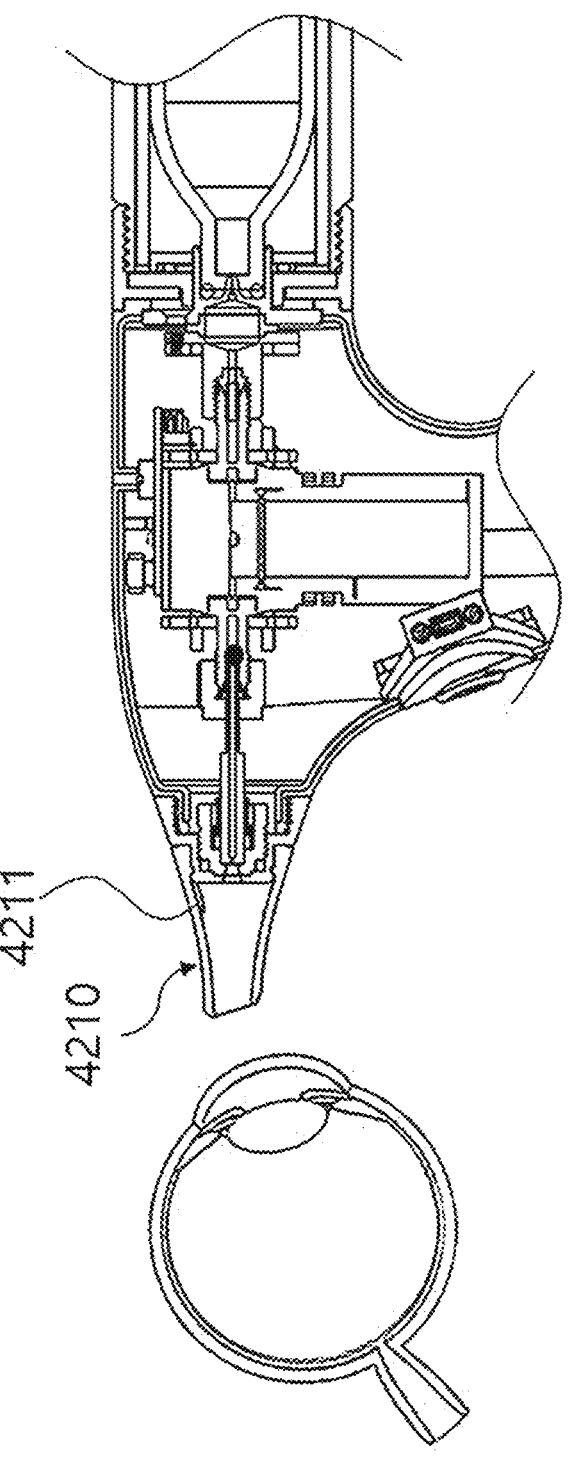
FIG. 33 is a diagram for describing a guide unit 4210 of the cooling device 10000 according to an embodiment of the present application.

FIG. 33 is a diagram for describing the guide unit 4210 of the cooling device 10000 according to an embodiment of the present application.

According to an embodiment of the present application, the guide unit 4210 may be implemented in a form in which one end surface thereof coming in contact with the subject to be treated which includes the target region TR is treated to be diagonal. The guide unit 4210 may have an orientation when coming in contact with the subject to be treated which includes the target region TR. As a specific example, in a case in which the cooling device 10000 is used to perform cooling on at least one region of an eye, the guide unit 4210 may have an orientation when coming in contact with the eye.

Here, the guide unit 4210 having an orientation when coming in contact with a specific object may mean that there is a direction in which damage to the specific object is minimized when the guide unit 4210 comes in contact with the specific object. For example, the guide unit 4210 having an orientation when coming in contact with the eye may come in contact with the eye so that one relatively protruding region of the guide unit 4210 faces a relatively less protruding region of the eye, and one relatively less protruding region of the guide unit 4210 faces a relatively protruding region of the eye. In other words, the guide unit 4210 may come in contact with the eye so that one relatively protruding region of the guide unit 4210 faces an outer side with respect to the center of the eye and one relatively less protruding region of the guide unit 4210 faces an inner side with respect to the center of the eye.

The guide unit 4210 according to an embodiment of the present application may include a periphery hole 4211. The periphery hole 4211 may be implemented to have a suitable position and/or shape to prevent the coolant flowing out through the periphery hole 4211 from flowing out to a surface of a subject to be treated on which cooling will be performed by the cooling device 10000. For example, the periphery hole 4211 may be implemented to have a position and/or shape in consideration of the orientation of the guide unit 4210.

As a specific example, in a case in which the cooling device 10000 sprays a coolant to an eye to perform cooling so that a degree of neural activation in the target region TR is temporarily reduced, the periphery hole 4211 of the guide unit 4210 of the cooling device 10000 may be formed in a region corresponding to the outer side with respect to the center of the eye when the guide unit 4210 comes in contact with the subject to be treated, which includes the target region TR, to have an orientation. In other words, in a case in which the cooling device 10000 sprays a coolant to an eye to perform cooling of the target region TR, when the guide unit 4210 comes in contact with the eye, the periphery hole 4211 of the guide unit 4210 may face the outer side with respect to the center of the eye. The periphery hole 4211 may be formed in a direction moving away from the eye when the guide unit 4210 comes in contact with the subject to be treated, which includes the target region TR, to have an orientation. The periphery hole 4211 may be formed in a side of the guide unit 4210 that is far from the eye when the guide unit 4210 comes in contact with the subject to be treated, which includes the target region TR, to have an orientation.

In a case in which cooling is performed using the cooling device 10000 including the guide unit 4210 according to the above-described embodiment, due to a coolant discharged through the periphery hole 4211, it is possible to derive effects of preventing the subject to be treated from drying and securing a field of vision to allow the target region TR to be visible to the operator during cooling.

According to an embodiment of the present application, the cooling device 10000 may further include a cooling restriction unit 4500 and/or a cooling mitigating unit 4600 to prevent the target region TR from being excessively cooled by a coolant sprayed through the nozzle unit 4100.

The cooling restriction unit 4500 according to an embodiment of the present application may perform a function of preventing excessive cooling of the target region TR.

For example, the cooling device 10000 according to an embodiment of the present application may, through the cooling restriction unit 4500, cause a coolant to be jetted in a direction other than a direction toward the target region TR or block the spraying of the coolant. As a specific example, the cooling restriction unit 4500 may be provided on a movement path of a coolant sprayed from the nozzle unit 4100 so that, through the cooling restriction unit 4500, a coolant is caused to be jetted in a direction other than a direction toward the target region TR or the spraying of the coolant is blocked even in a case in which jetting of a coolant cannot be blocked due to malfunctions, errors, or the like of the valve 2100 or the control unit 5000.

As another example, the cooling device 10000 according to an embodiment of the present application may, through the cooling restriction unit 4500, restrict a coolant flow or cause a position where the Joule-Thomson phenomenon of the coolant occurs to be spaced apart from a target site.

The cooling device 10000 according to an embodiment of the present application may perform an operation of preventing excessive cooling of the target region TR on the basis of the temperature of the cooling restriction unit 4500.

As a specific example, the cooling restriction unit 4500 may be disposed on a movement region of a coolant sprayed through the nozzle unit 4100, and thus a change in a temperature of the cooling restriction unit 4500 may occur during a cooling operation of the cooling device 10000. Therefore, the cooling device 10000 may perform an operation of preventing excessive cooling of the target region TR on the basis of whether the temperature of the cooling restriction unit 4500 is lower than a predetermined critical temperature.

The cooling restriction unit 4500 may include a portion with a large surface area to perform an efficient heat exchange with the coolant. For example, the cooling restriction unit 4500 may include a metal mesh, a porous material, a rough surface, or a plurality of fins but is not limited thereto.

The cooling device 10000 according to an embodiment of the present application may, when the temperature of the cooling restriction unit 4500 becomes lower than the predetermined critical temperature, cause a coolant to be jetted in a direction other than a direction toward the target region TR or block the spraying of the coolant.

For example, the cooling restriction unit 4500 may be implemented in the shape of a tube connected to the nozzle unit 4100, and when the temperature of the cooling restriction unit 4500 becomes lower than the predetermined critical temperature, the cooling device 10000 may operate so that the tube of the cooling restriction unit 4500 is bent to change a spraying direction or an inner diameter of the cooling restriction unit 4500 is narrowed to block the coolant sprayed to the target region TR.

As another example, the cooling restriction unit 4500 may be implemented as a manual actuator such as a bimetal formed by attaching two metal plates having different thermal expansion rates. Since, even when situations such as malfunctions or failures of the control unit 5000 or the valve 2100 occur, the cooling restriction unit 4500 implemented in the above form may be driven independently of the situations, the cooling restriction unit 4500 may stably block a coolant jetted to the target region TR in a case in which the temperature of the cooling restriction unit 4500 is lower than the predetermined critical temperature.

Figure 34:
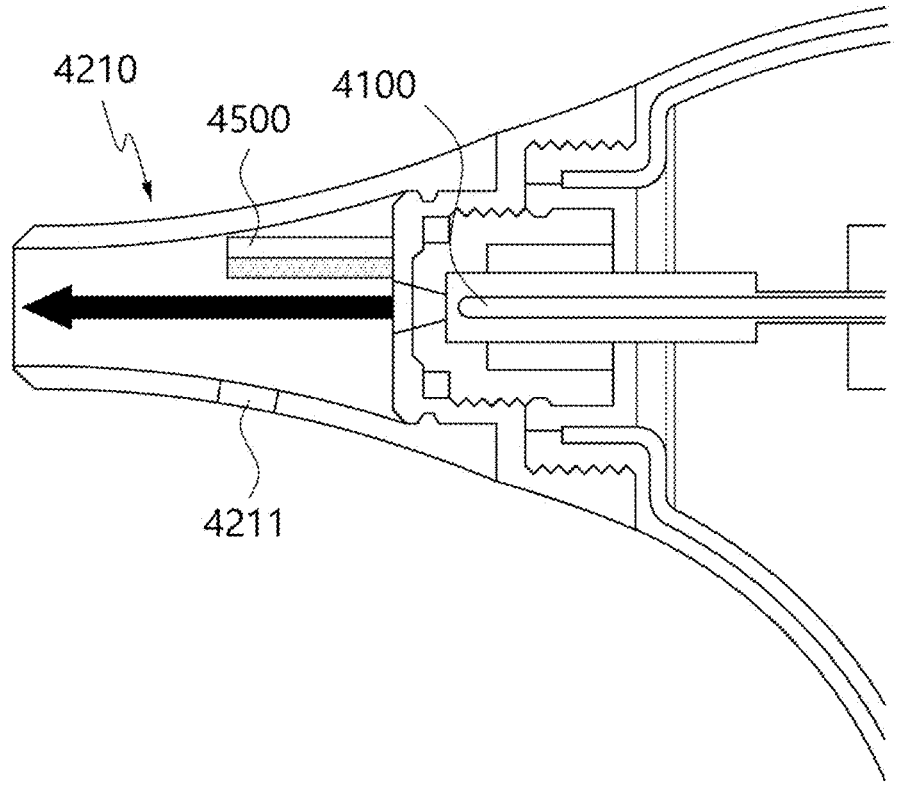
FIGS. 34 and 35 are diagrams for describing an operation of a cooling restriction unit 4500 according to an embodiment of the present application.
Figure 35:
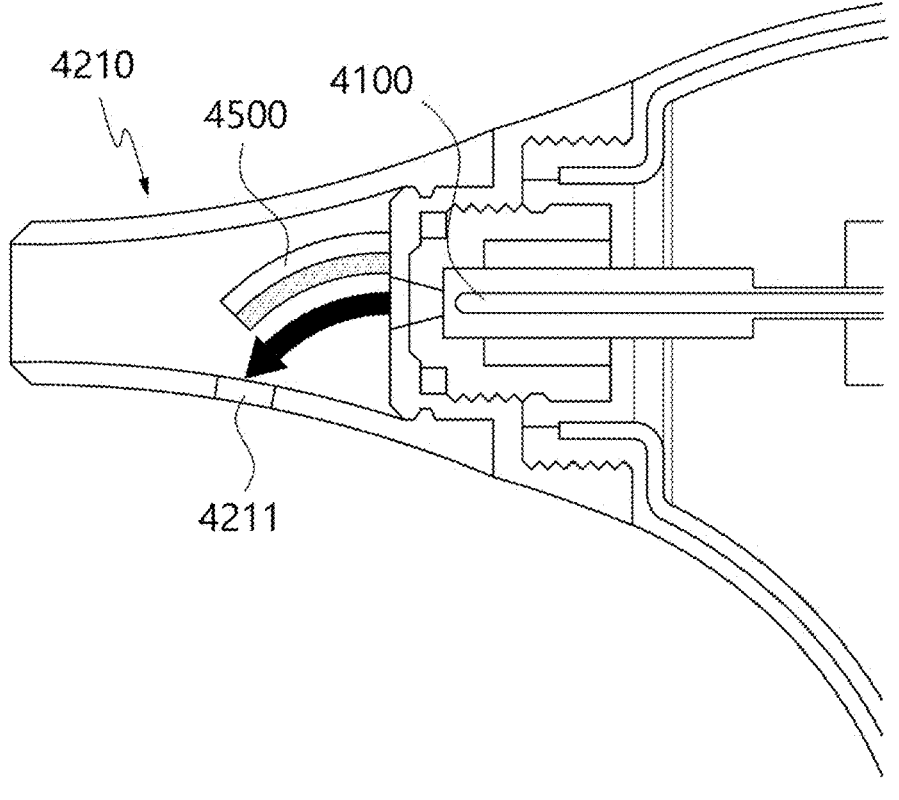

FIGS. 34 and 35 are diagrams for describing an operation of the cooling restriction unit 4500 according to an embodiment of the present application.

The cooling device 10000 according to an embodiment of the present application may include the nozzle unit 4100, the cooling restriction unit 4500, and the guide unit 4210.

Referring to FIG. 34, when the cooling device 10000 performs a normal operation, the cooling restriction unit 4500 may not block a coolant sprayed from the nozzle unit 4100 so as to allow the coolant sprayed from the nozzle unit 4100 to pass through the guide unit 4210 and be sprayed to the target region TR.

Here, the cooling device 10000 performing a normal operation may refer to a state in which the opening and/or closing of the valve 2100 is controlled according to a control protocol preset in the control unit 5000. Alternatively, the cooling device 10000 performing a normal operation may refer to a state in which the opening and/or closing of the valve 2100 is controlled on the basis of a control signal received from the control unit 5000.

The cooling restriction unit 4500 may include two or more metal materials, and a difference between thermal expansion rates of the two or more metal materials may be selected so that the cooling restriction unit 4500 does not block a coolant sprayed from the nozzle unit 4100 during the normal operation of the cooling device 10000.

Referring to FIG. 35, when the cooling device 10000 performs an excessive cooling operation, the cooling restriction unit 4500 may block spraying of a coolant from the nozzle unit 4100 or change a spraying direction of the coolant sprayed from the nozzle unit 4100 so as to prevent the coolant sprayed from the nozzle unit 4100 from passing through the guide unit 4210 and being sprayed to the target region TR.

Here, the cooling device 10000 performing an excessive cooling operation may refer to a state in which the temperature of the target region TR is lower as compared to a state in which the opening and/or closing of the valve 2100 is controlled according to a control protocol preset in the control unit 5000. Alternatively, the cooling device 10000 performing an excessive cooling operation may refer to a state in which the temperature of the cooling restriction unit 4500 is lower as compared to a state in which the opening and/or closing of the valve 2100 is controlled on the basis of a control signal received from the control unit 5000.

The cooling restriction unit 4500 may include two or more metal materials, and a difference between thermal expansion rates of the two or more metal materials may be selected so that the cooling restriction unit 4500 blocks spraying of a coolant from the nozzle unit 4100 or changes a spraying direction of a coolant sprayed from the nozzle unit 4100 during an excessive cooling operation of the cooling device 10000.

As a specific example, the cooling restriction unit 4500 may change a spraying direction of a coolant sprayed from the nozzle unit 4100 to block the coolant from reaching the target region TR. When the cooling device 10000 performs a normal operation, the cooling restriction unit 4500 may perform an operation of changing a spraying direction of a coolant sprayed from the nozzle unit 4100 so that the coolant sprayed from the nozzle unit 4100 is sprayed through a discharge port of the guide unit 4210. When the cooling device 10000 performs an excessive cooling operation, the cooling restriction unit 4500 may perform an operation of changing a spraying direction of a coolant sprayed from the nozzle unit 4100 so that the coolant sprayed from the nozzle unit 4100 is sprayed through the periphery hole 4211 of the guide unit 4210.

FIGS. 34 and 35 illustrate a case in which a jetting direction of a coolant is changed according to an embodiment of the cooling restriction unit 4500, but an angle at which the cooling restriction unit 4500 is bent may be increased to implement the cooling restriction unit 4500 in a form in which a coolant is jetted to the outside of the nozzle unit 4100. Also, although not illustrated separately, the cooling restriction unit 4500 may include the bimetal and a member configured to block coolant spraying linked to the bimetal, and the bimetal of the cooling restriction unit 4500 may be implemented to serve as a trigger of the blocking member. As a specific example, the member blocking the coolant spraying may be made of a material in which a movement range of the member that may be controlled using an elastic body, a magnet, or the like is relatively large.

The cooling restriction unit 4500 according to an embodiment of the present application may, when a temperature of a component of the cooling device 10000 that is thermally affected by a coolant becomes lower than the predetermined critical temperature, the cooling restriction unit 4500 may cause the coolant to be jetted in a direction other than a direction toward the target region TR or block the jetting of the coolant. The temperature of the component of the cooling device 10000 that is thermally affected may be a temperature lower than the predetermined critical temperature in a case in which the coolant is sprayed through the nozzle unit 4100 by an amount exceeding a predetermined spraying amount.

The component being thermally affected may include the nozzle unit 4100, the valve 2100, a pipe disposed between the nozzle unit 4100 and the valve 2100, and/or components related to a coolant after the coolant passes through the nozzle unit 4100 (for example, the cooling restriction unit 4500, the cooling mitigating unit 4600, the spraying site limiting unit, the distance maintaining unit 4900, etc.).

When the temperature of the component becomes lower than the predetermined critical temperature, the cooling device 10000 according to an embodiment of the present application may drive, as the cooling restriction unit 4500, an actuator configured to block spraying of a coolant.

As a specific example, the cooling restriction unit 4500 may include at least one of an electrically-driven actuator (solenoid actuator, motor, piezoelectric actuator, a magnetic actuator, a shape memory actuator, a thermodynamic actuator, a hydraulic actuator, a pneumatic actuator, and an electroactive polymer actuator and may change a direction of a coolant sprayed from the nozzle unit 4100 or block the spraying of the coolant from the nozzle unit 4100.

Figure 36:
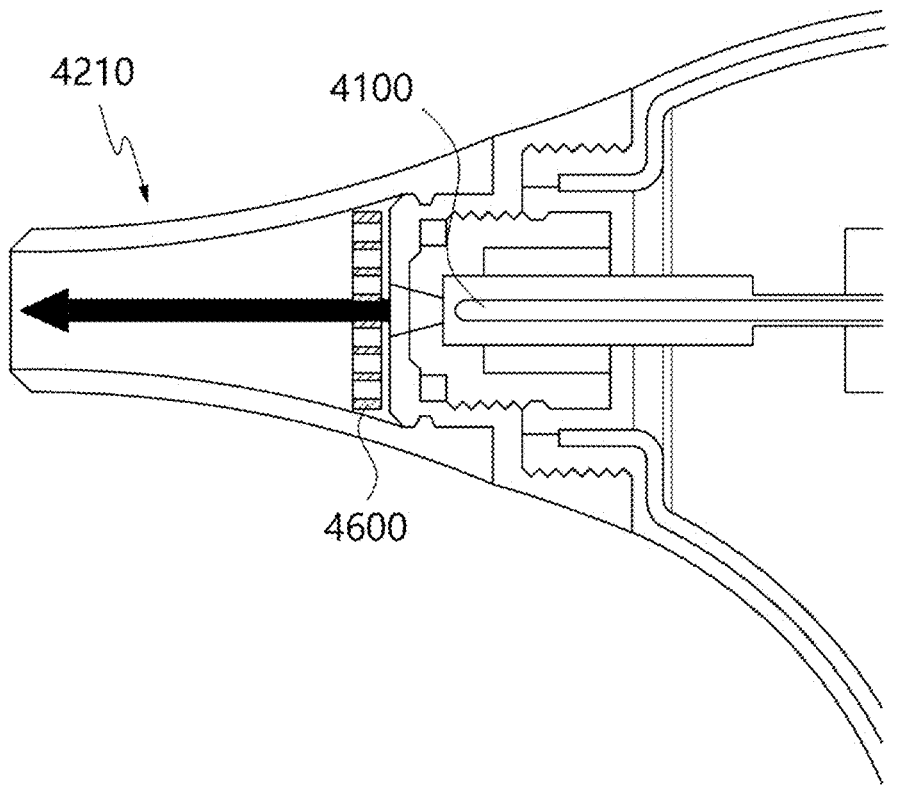
FIG. 36 is a diagram for describing a cooling mitigating unit 4600 according to an embodiment of the present application.

FIG. 36 is a view for describing the cooling mitigating unit 4600 according to an embodiment of the present application.

Referring to FIG. 36, the cooling mitigating unit 4600 may include a coolant heat exchange unit configured to mitigate a spraying temperature of a coolant through a heat exchange with the coolant. For example, the coolant heat exchange unit performs a function of performing a heat exchange before the coolant reaches the target region TR so as to cool the target region TR to a temperature higher than the temperature of the coolant right after the coolant is sprayed. As a specific example, the coolant heat exchange unit may be disposed at a position suitable for the coolant heat exchange unit to come in direct contact with the coolant to exchange heat therewith or may be disposed at a position suitable for air included in the coolant heat exchange unit to exchange heat with the coolant so as to perform a function of cooling the target region TR to a temperature higher than the temperature of the coolant right after the coolant is sprayed.

For example, the cooling mitigating unit 4600 may be disposed on a movement path of a coolant sprayed from the nozzle unit 4100 to mitigate the temperature of the coolant sprayed through the nozzle unit 4100. According to an embodiment of the present application, the coolant heat exchange unit may be disposed on a movement path of a coolant being sprayed from the nozzle unit 4100, and the coolant heat exchange unit may absorb heat from the coolant sprayed through the nozzle unit 4100 through a heat capacity of the coolant heat exchange unit itself in order to control the temperature of the coolant reaching the target region TR and mitigate the coolant spraying temperature of the cooling device 10000.

The cooling mitigating unit 4600 may include a coolant heat exchange unit having a wide contact region to efficiently perform a heat exchange with a coolant. As a specific example, the coolant heat exchange unit may have a contact region of 100 mm² or more. As another specific example, the coolant heat exchange unit may be in the shape of a mesh. A contact area of one of a plurality of passing regions of the mesh through which a coolant passes may be implemented to be 1 mm² or less. Alternatively, the contact area of one of the plurality of passing regions of the mesh through which a coolant passes may be implemented to be 10 mm² or less.

The coolant heat exchange unit may be implemented to have various configurations, shapes, and the like, and of course, the coolant heat exchange unit may be implemented to be in a shape other than the shape of the mesh described above. For example, in a case in which the coolant heat exchange unit is implemented to have a plurality of layers, the shapes of the layers of the coolant heat exchange unit may be implemented to be different from each other. As another example, the coolant heat exchange unit may be implemented using a plurality of fins or include a porous material.

According to an embodiment of the present application, the cooling mitigating unit 4600 may mitigate a spraying temperature of a coolant in the form of controlling the outflow amount and/or outflow speed of the coolant. For example, the cooling mitigating unit 4600 may be disposed on a flow path of a coolant sprayed from the nozzle unit 4100 and may come in mechanical contact with the coolant before the coolant reaches the target region TR in order to mitigate the spraying temperature of the coolant. Specifically, the cooling mitigating unit 4600 may come in mechanical contact with the coolant to control an outflow speed of the coolant to be decreased and may, due to the decrease in the outflow speed of the coolant, mitigate the coolant spraying temperature of the cooling device 10000 to induce cooling of the target region TR. The mitigated cooling may be due to a decrease in a heat exchange coefficient (W/m²·K) between a target site and a coolant that is caused by the decrease in the outflow speed of the coolant.

The cooling mitigating unit 4600 according to an embodiment of the present application may mitigate a spraying temperature of a coolant reaching the target region TR to perform initial control that allows cooling of the target region TR by the coolant to be smoothly performed.

As described above, the cooling mitigating unit 4600 may control the outflow speed of the coolant passing through the cooling mitigating unit 4600. The cooling device 10000 including the cooling mitigating unit 4600 may derive an effect of filtering impurities or the like included in a coolant by the cooling mitigating unit 4600 so that the amount of impurities reaching the target region TR is reduced or the impurities are eliminated.

As described above, the cooling mitigating unit 4600 may control the temperature of the coolant passing through the cooling mitigating unit 4600. In order to improve the efficiency of controlling the temperature of the coolant that is controlled through the cooling mitigating unit 4600, a contact area between the coolant heat exchange unit and the coolant should be increased, and to this end, a fin or the like may be additionally configured inside the cooling mitigating unit 4600 to control the temperature of the coolant passing through the cooling mitigating unit 4600. Here, a material having thermal conductivity of 10 W/m-K or more may be selected as the material of the cooling mitigating unit 4600 that controls the temperature of the coolant.

According to an embodiment of the present application, the cooling mitigating unit 4600 may be configured to be integrated with the spraying site limiting unit. The cooling mitigating unit 4600 may be configured to be integrated with the guide unit 4210. Before the coolant sprayed through the nozzle unit 4100 reaches the target region TR, the guide unit 4210 may perform a function of providing a space that allows mixing of a coolant and surrounding air to occur on a coolant spraying region limited due to the discharge port of the guide unit 4210 so as to mitigate the coolant spraying temperature. Specifically, the coolant whose spraying region is limited by the guide unit 4210 may be actively mixed with air present inside the guide unit 4210 or adjacent thereto. Through active mixing of the air and coolant, the coolant to be sprayed to the target region TR actively performs a heat exchange with the air. Accordingly, a phenomenon in which, in an initial cooling process for the target region TR, the temperature of the coolant to be sprayed to the target region TR is increased or the speed of the coolant flowing toward the target region TR is reduced is caused, thereby performing a function of mitigating the coolant spraying temperature.

According to an embodiment of the present application, the cooling mitigating unit 4600 may be configured to be linked to the cooling restriction unit 4500. The coolant whose temperature is mitigated upon passing through the cooling mitigating unit 4600 may be transferred to the cooling restriction unit 4500, and the cooling restriction unit 4500 may, when the temperature of the cooling restriction unit 4500 is lower than a predetermined critical temperature, change a jetting direction of the coolant sprayed from the nozzle unit 4100 or block the jetting of the coolant.

According to an embodiment of the present application, the cooling mitigating unit 4600 may have a certain heat capacity, and the coolant may perform a function of cooling the cooling mitigating unit 4600 without coming in direct contact with the target region TR. In this way, an influence of the coolant speed on the coolant of the target region TR may be minimized, and the cooling mitigating unit 4600 may come in direct contact with the target region TR to perform cooling. Here, the cooling mitigating unit 4600 may include a region made of a material having thermal conductivity of 10 W/m-K or more.

According to an embodiment of the present application, the cooling mitigating unit 4600 may exchange heat with a coolant to control a cooling temperature of the target region TR even when periodical (or non-periodical) control of the opening and closing of the valve 2100 is not present. For example, in a case in which the cooling mitigating unit 4600 has a predetermined heat capacity or performs a heat exchange of a predetermined numerical value or more with surrounding components or surrounding air, even when the valve 2100 is continuously open and a coolant is continuously sprayed, the target region TR may be cooled while the temperature of the coolant before the coolant reaches the target region TR is controlled. In order to derive such an effect, the cooling mitigating unit 4600 may have predetermined thermal conductivity, surface area, and/or specific heat. Specifically, in the cooling mitigating unit 4600, a surface area coming in contact with the coolant may be 100 mm² or more, and specific heat may be 0.01 J/K or more.

The nozzle unit 4100, the guide unit 4210, the cooling restriction unit 4500, and the cooling mitigating unit 4600 that may be included in the cooling device 10000 according to an embodiment of the present application have been described in detail above. The above elements are only some elements that may be included in the cooling device 10000 that directly sprays a coolant to a target region TR to cool the target region TR do not indicate that the cooling device 10000 should always include the above-described configurations.

In other words, the present application has been described above with reference to some embodiments illustrated in the drawings, but the description is merely illustrative, and those of ordinary skill in the art should understand that various modifications and modified embodiments are possible therefrom. Therefore, the actual technical scope of the present disclosure should be defined by the technical idea of the attached claims.

Hereinafter, some control methods of the type of cooling device 10000 that sprays a coolant will be disclosed.

2. Control 2.1 Cooling Control

The cooling device 10000 according to an embodiment of the present application may spray a coolant to a target region TR to perform cooling of the target region TR. The cooling device 10000 may spray a coolant to a target region TR to perform cooling of the target region TR.

For example, the cooling device 10000 may cause the valve 2100 to be open for a predetermined amount of time to spray the coolant to the target region TR.

As a specific example, the cooling device 10000 may apply continuous current to the valve 2100. The control unit 5000 may send a signal for opening the valve 2100 to the valve 2100 and, when a predetermined amount of time elapses, send a signal for closing the valve 2100 to the valve 2100. A coolant corresponding to the amount of coolant sprayed when the valve 2100 is open during the time until the signal for closing the valve 2100 is sent after the signal for opening the valve 2100 is sent may be sprayed to the target region TR.

As another example, the cooling device 10000 may cause the valve 2100 to repeat opening and closing for a certain amount of time in order to perform cooling. As a specific example, the cooling device 10000 may apply current in the form of PWM to the valve 2100. The control unit 5000 may send the signal for opening the valve 2100 and the signal for closing the valve 2100 to the valve 2100 a predetermined number of times at predetermined intervals. A coolant corresponding to the amount of coolant, which is obtained by multiplying the number of times of spraying a coolant by the amount of coolant sprayed when the valve 2100 is open during the time until the signal for closing the valve 2100 is sent after the signal for opening the valve 2100 is sent, may be sprayed to the target region TR.

As described above, the cooling device 10000 according to an embodiment of the present application may perform a function of discharging a coolant to a target region TR to cool the target region TR.

When a coolant is discharged to the target region TR, heat loss may occur in the target region TR, and the target region TR may be cooled. When a coolant is sprayed from the cooling device 10000 to the target region TR, at least one phenomenon of radiation, conduction, and/or convection may occur in the target region TR, and the target region TR may be cooled.

The cooling device 10000 may control the amount of coolant sprayed per unit time of the coolant sprayed to the target region TR so as to control the extent to which the target region TR is cooled and/or the cooling speed. The amount of sprayed coolant may be controlled by the valve 2100.

For example, the cooling device 10000 may extend the opening/closing time of the valve to control the cooling extent so that the temperature of the target region TR is decreased to a relatively lower temperature. As another example, the cooling device 10000 may increase the frequency of opening the valve 2100 within a certain amount of time to control the cooling extent and cooling speed so that the temperature of the target region TR is cooled to a target cooling temperature at a relatively higher speed.

The cooling device 10000 may control the temperature of the coolant discharged to the target region TR to control the extent to which the target region TR is cooled and/or the cooling speed. The temperature of the sprayed coolant may be controlled by the valve 2100 and/or the spraying temperature regulating unit 3100.

For example, the cooling device 10000 may increase the extent of outflow of the coolant from the valve 2100 to control the cooling speed and cooling extent so that the temperature of the target region TR is decreased to a lower temperature at a relatively higher speed. As another example, the cooling device 10000 may induce heat generation or heat absorption of the coolant due to the spraying temperature regulating unit 3100 to control the cooling extent so that the temperature of the target region TR is controlled to an appropriate temperature.

According to an embodiment of the present application, the cooling device 10000 may operate according to a pre-stored cooling protocol. For example, the control unit 5000 may control the valve 2100 according to the pre-stored cooling protocol.

According to an embodiment of the present application, the cooling device 10000 may operate in two or more cooling modes.

For example, the cooling device 10000 may operate in two or more cooling modes during one cooling operation.

Figure 37:
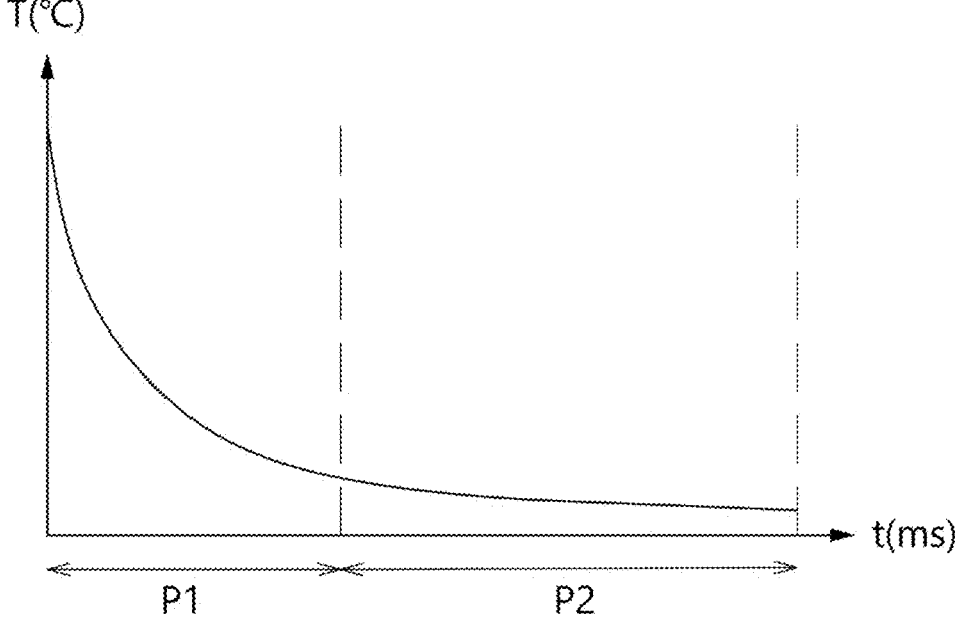
FIG. 37 is a diagram for describing a temperature change in a target region TR in a case in which the cooling device 10000 according to an embodiment of the present application operates in two different cooling modes while performing one cooling operation.

FIG. 37 is a diagram for describing a temperature change in a target region TR in a case that the cooling device 10000 according to an embodiment of the present application completes one cooling operation with two different cooling modes.

When one cooling operation for the target region TR starts, the cooling device 10000 according to an embodiment of the present application may perform a first cooling mode in which the temperature of the target region TR is decreased and may perform a second cooling mode in which the temperature of the target region TR is maintained to be within a predetermined temperature range. For example, the predetermined temperature range may be 5° C. to 10° C. As another example, the predetermined temperature range may be −15° C. to −12° C. As still another example, the predetermined temperature range may be −45° C. to −40° C.

When one cooling operation for the target region TR starts, the cooling device 10000 may perform cooling so that an absolute value of a temperature gradient with time of the target region TR during a first time P1 is larger than an absolute value of a temperature gradient with time of the target region TR during a second time P2. The first time P1 may be the time during which the cooling device 10000 operates in the first cooling mode. The second time P2 may be the time during which the cooling device 10000 operates in the second cooling mode.

In a case in which the target region TR is cooled to anesthetize the target region TR, when time required to perform initial cooling (that is, cooling to a temperature at which a degree of neural activation is reduced) is long, a subject receiving treatment may feel excessive pain due to cooling of the target region TR.

However, in a case in which, in performing one cooling operation, the cooling device 10000 sequentially performs a first cooling mode in which rapid cooling is performed and a second cooling mode in which the temperature is maintained within a predetermined range, an effect of minimizing pain felt by the subject receiving treatment due to cooling of the target region TR and an effect of stably inducing cooling anesthesia of the target region TR may be achieved.

Preferably, the control unit 5000 may control the time during which the first cooling mode is performed to be shorter than the time during which the second cooling mode is performed, and here, pain felt by the subject receiving cooling treatment may be minimized.

According to an embodiment of the present application, the cooling device 10000 that operates in the first cooling mode and the second cooling mode may appropriately apply and implement the above-described methods of controlling the cooling extent and/or cooling speed.

Hereinafter, description will be given on a method in which, when one cooling operation for the target region TR starts, the cooling device 10000 controls the valve 2100 to perform a first cooling mode in which the temperature of the target region TR is decreased and a second cooling mode in which the temperature of the target region TR is maintained within a predetermined temperature range.

Figure 38:
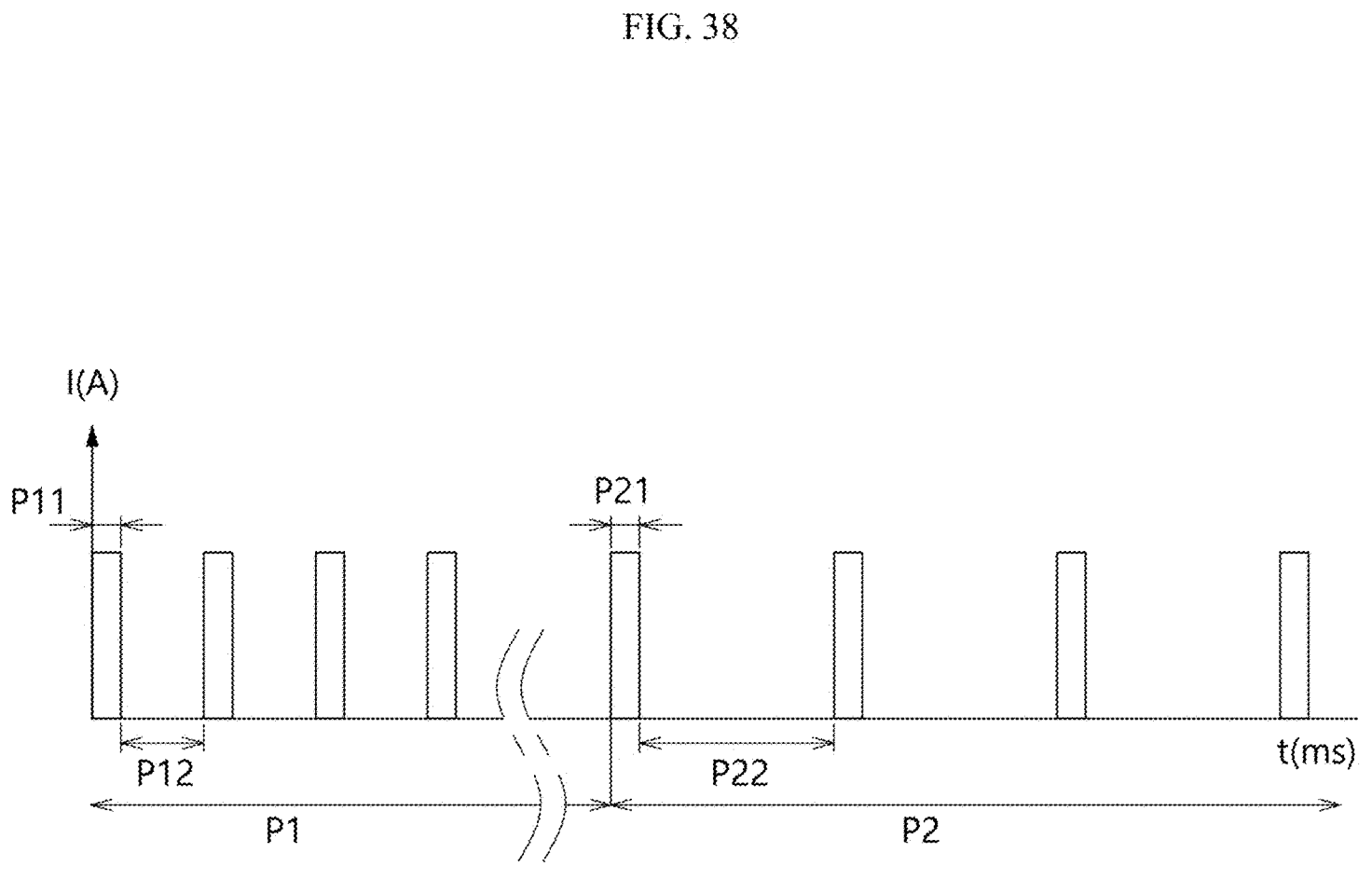

FIG. 38 is a diagram for describing a method of controlling the valve 2100 in a case in which the cooling device 10000 according to an embodiment of the present application operates in two different cooling modes while performing one cooling operation.

The cooling device 10000 according to an embodiment of the present application may control at least one of the frequency of opening the valve and the duration of opening of the valve to allow the cooling device 10000 to operate in two different cooling modes while performing one cooling operation.

For example, when switching from the first cooling mode to the second cooling mode occurs, the total time in which the valve 2100 is open during a predetermined amount of time may be reduced. As another example, when switching from the first cooling mode to the second cooling mode occurs, the frequency of opening the valve 2100 during a predetermined amount of time may be the same, but the duration of opening of the valve 2100 may be decreased. As still another example, when switching from the first cooling mode to the second cooling mode occurs, the duration of opening of the valve 2100 during a predetermined amount of time may be the same, but the frequency of opening the valve 2100 may be decreased.

As a specific example in which the frequency of opening the valve 2100 is decreased, the first cooling mode may be a mode in which the control unit 5000 repeats, during the first time P1, an operation of opening the valve 2100 during a seventh time P11 and closing the valve 2100 during an eighth time P12. The second cooling mode may be a mode in which the control unit 5000 repeats, during the second time P2, an operation of opening the valve 2100 during a ninth time P21 and closing the valve 2100 during a tenth time P22. Here, the tenth time P22 may be longer than the eighth time P12. Here, the seventh time P11 and the ninth time P21 may be the same. For example, the seventh time P11 may be about 25 ms, the ninth time P21 may be about 25 ms, the eighth time P12 may be 175 ms, and the tenth time P22 may be 308 ms.

According to an embodiment of the present application, the cooling device 10000 may directly spray a coolant to a target region TR to perform cooling and may include the guide unit 4210 configured to limit a region to which the coolant is sprayed.

In a case in which the cooling device 10000 including the guide unit 4210 performs cooling, for safe separation between the guide unit 4210 and the subject receiving treatment, the control unit 5000 may further perform a third cooling mode. For example, the control unit 5000 may control the valve 2100 to, after performing the first cooling mode and the second cooling mode, perform the third cooling mode before ending cooling and may control the valve 2100 so that the target region TR reaches a temperature higher than a predetermined temperature range. Here, the predetermined temperature range may be a temperature range of the target region TR that is set to be maintained in the second cooling mode.

According to an embodiment of the present application, the cooling device 10000 may control performance of the second cooling mode to start on the basis of the temperature of the target region TR. The cooling device 10000 may control performance of the second cooling mode to end on the basis of the temperature of the target region TR.

For example, the control unit 5000 may control the valve 2100 to be in the first cooling mode until the temperature of the target region TR reaches a first critical temperature. When the temperature of the target region TR reaches the first critical temperature, the control unit 5000 may control the valve 2100 to be in the second cooling mode. The control unit 5000 may continuously check whether the temperature of the target region TR is within a predetermined temperature range and may control the valve 2100 to end the second cooling mode on the basis of whether a predetermined amount of time has elapsed after the temperature of the target region TR reached a target cooling temperature.

The cooling device 10000 that cools the target region TR to a target cooling temperature according to switching to predetermined modes and a control method of the cooling device 10000 have been disclosed above.

Hereinafter, a more flexible control method of the cooling device 10000 for cooling a target region TR to a target cooling temperature and the cooling device 10000 will be disclosed. For example, the cooling device 10000 may perform feedback cooling control to cool the temperature of the target region TR to a target cooling temperature on the basis of the temperature of the target region TR. As another example, the cooling device 10000 may perform feedback cooling control to cool the temperature of the target region TR to a target cooling temperature on the basis of the temperature of the reservoir 1100 of the cooling device 10000. As still another example, the cooling device 10000 may perform feedback cooling control to cool the temperature of the target region TR to a target cooling temperature on the basis of the amount of coolant accommodated in the reservoir 1100.

The present disclosure is not limited thereto, and the cooling device 10000 may be implemented to cool the temperature of the target region TR to a target cooling temperature on the basis of a detected value that may be changed in the process of actually using the cooling device 10000.

2.2 Feedback Cooling Control 2.2.1 Control According to Temperature of Target Region TR The cooling device 10000 according to an embodiment of the present application may cool the temperature of the target region TR to a target cooling temperature on the basis of the temperature of the target region TR. The cooling device 10000 according to an embodiment of the present application may cool the temperature of the target region TR to a target cooling temperature on the basis of a temperature distribution on a surface of a subject to be treated which includes the target region TR.

Figure 39:
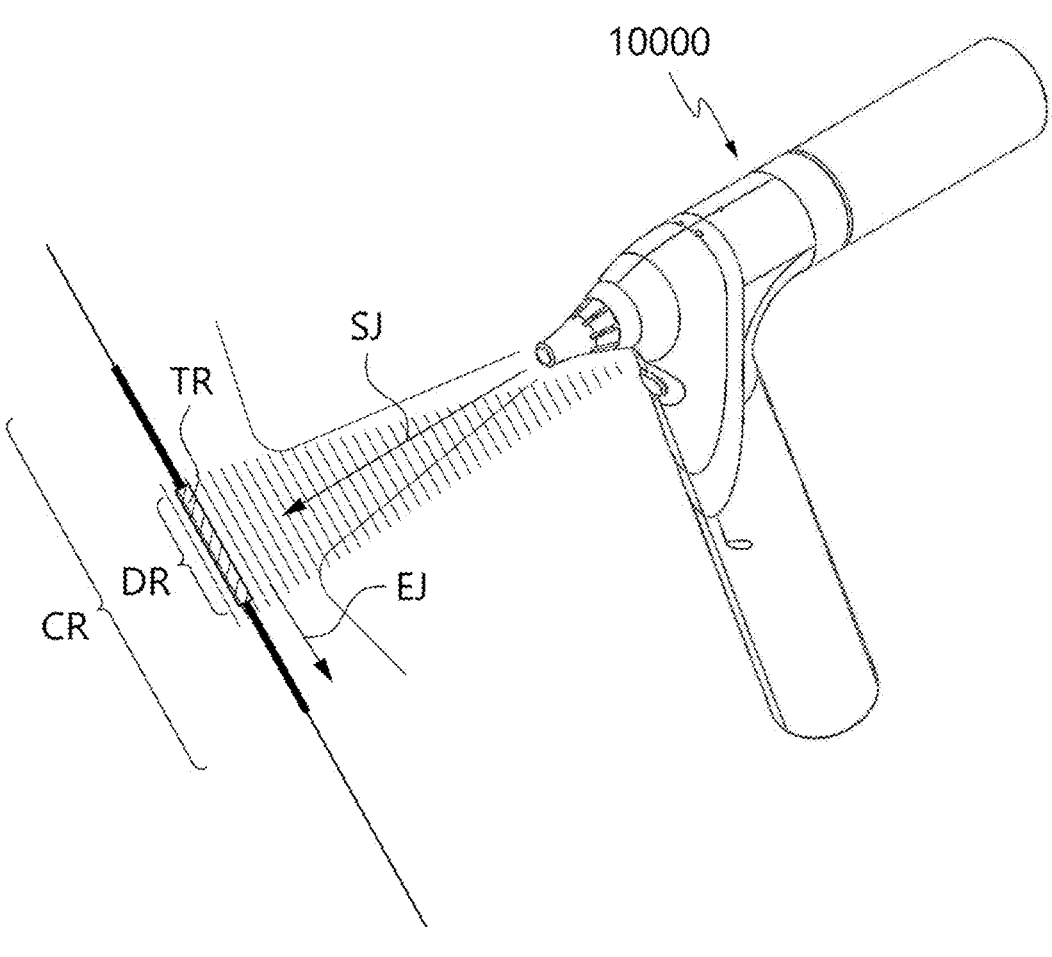
FIG. 39 is a diagram for describing the cooling device 10000 that performs feedback cooling control based on the temperature of the target region TR according to an embodiment of the present application.

FIG. 39 is a diagram for describing the cooling device 10000 that performs feedback cooling control on the basis of the temperature of the target region TR according to an embodiment of the present application.

The cooling device 10000 may include a temperature sensor 6100 configured to measure a temperature of a detection region DR. For example, the temperature sensor 6100 may be a temperature sensor 6100 that converts an intensity of infrared rays emitted from the detection region DR into heat and checks an average temperature of the detection region DR on the basis of a temperature detected by a heat sensor included in the temperature sensor 6100. As a specific example, the temperature sensor 6100 may be an infrared temperature sensor.

The detection region DR may include at least a partial region of the target region TR. For example, the detection region DR may include a point of the target region TR where the temperature is the lowest. As another example, the detection region DR may include the entire target region TR. As still another example, the detection region DR may coincide with the target region TR.

The detection region DR may be included in a region to which a coolant is sprayed. The detection region DR may be included in the cooling region CR. The detection region DR may be at least a partial region of the cooling region CR in which the temperature decreases due to spraying of a coolant. For example, the detection region DR may coincide with the cooling region CR. As another example, the detection region DR may be a partial region of the cooling region CR.

The cooling device 10000 may cool the target region TR on the basis of the temperature of the target region TR. For example, the cooling device 10000 may cool the target region TR on the basis of the temperature of the detection region DR that includes the point of the target region TR where the temperature is the lowest.

According to an embodiment of the present application, the cooling device 10000 may compare the temperature of the detection region DR with a pre-stored critical value to perform feedback cooling control for the target region TR.

For example, the cooling device 10000 may operate in the first cooling mode for cooling the temperature of the target region TR. While operating in the first cooling mode, the cooling device 10000 may check whether the temperature of the detection region DR has reached a first critical value.

When the temperature of the detection region DR reaches the first critical value while the cooling device 10000 operates in the first cooling mode, the cooling device 10000 may operate in the second cooling mode for maintaining the temperature of the target region TR within a target cooling temperature range.

While operating in the second cooling mode, the cooling device 10000 may check whether the temperature of the detection region DR has reached a second critical value.

When the temperature of the detection region DR reaches the second critical value while the cooling device 10000 operates in the second cooling mode, the cooling device 10000 may operate in the first cooling mode. For example, the first critical value may be a value smaller than the second critical value.

The cooling device 10000 may repeatedly perform at least the first cooling mode and the second cooling mode on the basis of the temperature of the detection region DR.

Here, the first cooling mode may be a mode in which the cooling extent and/or cooling speed is controlled to allow more rapid cooling to be performed as compared to the second cooling mode. For example, the first cooling mode may be a mode in which the opening time of the valve 2100 per unit time is controlled to be relatively longer as compared to the second cooling mode. As a specific example, the control unit 5000 may perform the first cooling mode and the second cooling mode in a form of controlling the valve 2100 to repeat opening and closing. Here, the control unit 5000 may reduce the opening time of the valve 2100 per unit time in a form of increasing the closing time of the valve 2100 so as to switch to the second cooling mode.

As another example, the second cooling mode may be a mode in which heating of a coolant through the spraying temperature regulating unit 3100 is controlled to be further performed as compared to the first cooling mode.

Here, the second cooling mode may be a mode in which the cooling extent is reduced as compared to the first cooling mode or cooling is controlled to be stopped. For example, the valve 2100 may be opened in the first cooling mode but may not be opened in the second cooling mode.

The cooling device 10000 may end the cooling operation when a predetermined condition is reached. For example, the predetermined condition may be a condition in which the temperature of the detected region DR is maintained within a target cooling range during a predetermined amount of time. As a specific example, the predetermined condition may be a condition in which the temperature of the target region TR is maintained to −15° C. for three seconds.

Figure 40:
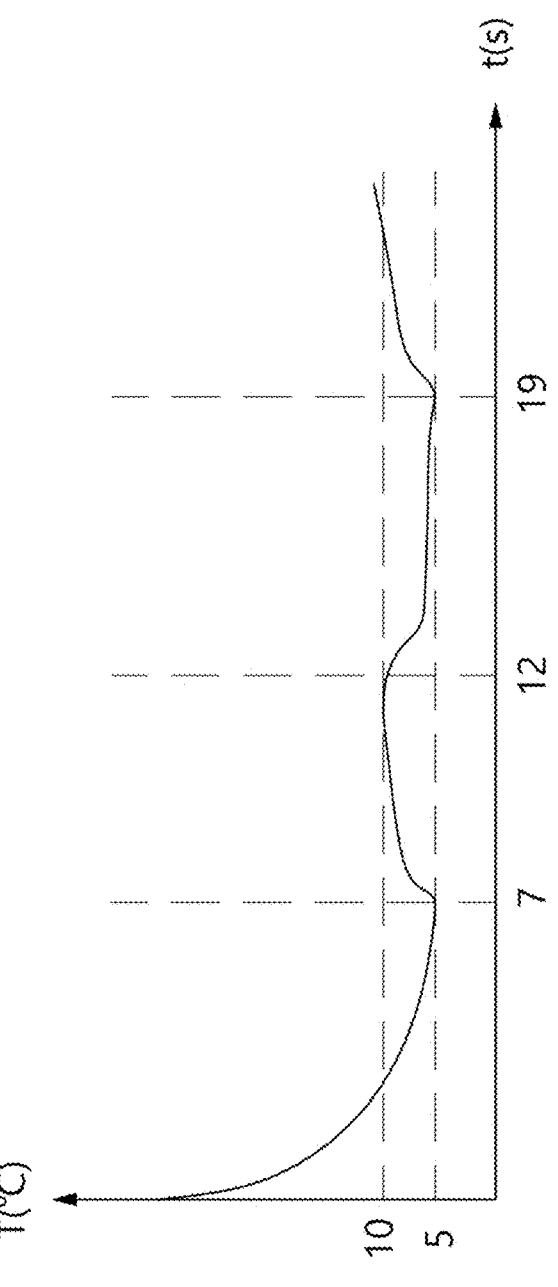
FIG. 40 illustrates a temperature graph of the target region TR when the cooling device 10000 according to an embodiment of the present application performs feedback cooling control for the target region TR by comparing a temperature of a detection region DR and a pre-stored critical value.

FIG. 40 illustrates a temperature graph of the target region TR in a case in which the cooling device 10000 according to an embodiment of the present application compares the temperature of the detection region DR and a pre-stored critical value to perform feedback cooling control for the target region TR.

The experiment was conducted using the cooling device 10000 including the transfer unit 1200, the valve 2100, the spraying temperature regulating unit 3100, and the nozzle unit 4100, and the control unit 5000 of the cooling device 10000 was set to, when the cooling operation is started, open the valve 2100 until the temperature of the detection region DR reaches 5° C. (that is, a first critical value) (first cooling mode), was set to, when the temperature of the detection region DR reaches 5° C. (that is, the first critical value), close the valve 2100 until the temperature of the detection region DR reaches 10° C. (that is, a second critical value) (second cooling mode), and was set to, when the temperature of the detection region DR reaches 10° C., open the valve 2100 again.

As a result of conducting the experiment using the cooling device 10000 including the control unit 5000 set as described above, the temperature of the target region TR was confirmed to be controlled within a target cooling temperature range.

In the case of the cooling device 10000 that detects the temperature of the detection region DR to perform feedback cooling control, the temperature of the target region TR may be stably controlled to the target cooling temperature range without excessively cooling the target region TR.

However, when the detection region DR in which the cooling device 10000 detects a temperature corresponds to an excessively large region, or a region of the detection region DR that overlaps with the target region TR corresponds to a specific region that is significantly small, feedback cooling control may not be normally performed, and thus suitable cooling of the target region TR may not be performed or excessive cooling may be performed on the target region TR.

Therefore, the cooling device 10000 may include the temperature sensor 6100 having the detection region DR which is suitably determined on the basis of a distance between the cooling device 10000 and a subject to be treated, a spraying range of a coolant sprayed through the nozzle unit 4100, and a thermal diffusion coefficient of the subject to be treated, and the like.

For example, in the case of the cooling device 10000 including the distance maintaining unit 4900, the cooling device 10000 may include a temperature sensor 6100 that is set so that the detection region DR is included in the cooling region CR when a coolant is sprayed in a state in which the subject to be treated and the cooling device 10000 are spaced apart by a distance corresponding to the distance maintaining unit 4900.

Figure 41:
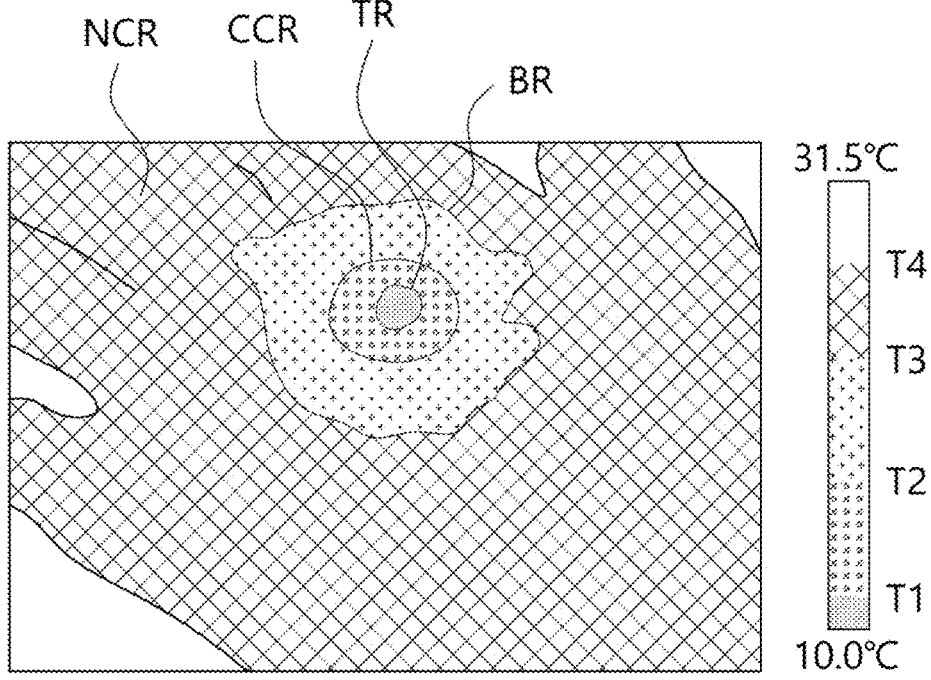
FIG. 41 is a diagram for describing temperature distribution of a surface of a subject to be treated including a target region TR when the cooling device 10000 according to an embodiment of the present application cools the target region TR.

FIG. 41 is a diagram for describing temperature distribution of a surface of a subject to be treated including a target region TR in a case in which the cooling device 10000 according to an embodiment of the present application cools the target region TR.

FIG. 41 illustrates a thermal image of one's hand which is patterned for each section when cooling is performed on the hand using the cooling device 10000 according to an embodiment of the present application.

In a case in which the cooling device 10000 according to an embodiment of the present application sprays a coolant to a target region TR to cool the target region TR, a temperature of a subject to be treated which includes the target region TR may show a specific temperature distribution. This may be due to, as described with reference to FIG. 42, the cooling device 10000 according to an embodiment of the present application spraying a coolant in the forms of the spread jet SJ and the free jet FJ.

The surface of the subject to be treated on which cooling is performed by the cooling device 10000 may show a specific temperature distribution. On the basis of a virtual isotherm, at least a central cooling region CCR, a boundary region BR, and a non-cooling region NCR may be formed on the surface of the subject to be treated.

The central cooling region CCR may include a region of the surface of the subject to be treated where the temperature is the lowest. The central cooling region CCR may include a region of the surface of the subject to be treated where a difference from the lowest temperature is within a central critical temperature. According to an embodiment of the present application, the central critical temperature may be a value obtained by dividing a difference between the highest temperature and the lowest temperature on the surface of the subject to be treated by 3. For example, in a case in which the lowest temperature on the surface of the subject to be treated is 10° C. and the highest temperature is 31° C., the central critical temperature may be 7° C. (=(31−10)/3)), and accordingly, the central cooling region CCR may be a region having a temperature in a range of 10° C. to 17° C.

According to an embodiment, the central critical temperature may be set according to features (or versions) of the cooling device 10000. For example, in a case in which the cooling device 10000 has to perform relatively precise cooling, the central critical temperature may be set to a smaller value. In a case in which the cooling device 10000 has to perform relatively less precise cooling, the central critical temperature may be set to a larger value.

The boundary region BR may include a region of the surface of the subject to be treated where the temperature is an intermediate temperature. The boundary region BR may be included in a region between the central cooling region CCR and the non-cooling region NCR. The boundary region BR may be a region having a temperature that corresponds to a specific temperature range between the temperature range of the central cooling region CCR and the temperature range of the non-cooling region NCR. The boundary region BR may include a region where a difference from a temperature of an edge of the central cooling region CCR is within a barrier critical temperature. According to an embodiment of the present application, the barrier critical temperature may be the value obtained by dividing the difference between the highest temperature and the lowest temperature on the surface of the subject to be treated by 3.

The non-cooling region NCR may include a region of the surface of the subject to be treated where the temperature is the highest. The non-cooling region NCR may include a region of the surface of the subject to be treated where a difference from the highest temperature is within a non-cooling critical temperature. According to an embodiment of the present application, the non-cooling critical temperature may be the value obtained by dividing the difference between the highest temperature and the lowest temperature on the surface of the subject to be treated by 3.

Referring to FIG. 41, as a specific example, the central cooling region CCR may be a region having a temperature in a range of 10° C. to lower than 17° C. The boundary region BR may be a region having a temperature in a range of 17° C. to lower than 24° C. The non-cooling region NCR may be a region having a temperature in a range of 24° C.

to lower than 31.5° C. The target region TR may be included in the central cooling region CCR and may be cooled to a temperature in a range of 10° C. to 11° C.

A temperature distribution on the surface of the subject to be treated on which cooling is performed by the cooling device 10000 according to an embodiment of the present application may be in a form having one or more virtual concentric circles. For example, the central cooling region CCR may have a circular shape, and a boundary of at least one temperature value within the central cooling region CCR may have a circular shape. The boundary region BR may be in a relatively less standardized form than the central cooling region CCR. The boundary region BR may not have a circular shape.

Referring to FIG. 41, as a specific example, the central cooling region CCR may have a circular shape. The boundary region BR may be in a less standardized form than the central cooling region CCR. The boundary region BR may be in a more radiated form than the central cooling region CCR. The non-cooling region NCR may be in a form excluding the boundary region BR and the central cooling region CCR.

According to an embodiment of the present application, the cooling device 10000 may cool the subject to be treated including the target region TR so that the target region TR belongs to the central cooling region CCR.

The cooling device 10000 according to an embodiment of the present application may cool the temperature of the target region TR to a target cooling temperature on the basis of the temperature distribution on the surface of the subject to be treated including the target region TR. The cooling device 10000 may cool the temperature of the target region TR to a target cooling temperature on the basis of the temperature of the central cooling region CCR including the target region TR.

According to an embodiment of the present application, the cooling device 10000 may perform feedback cooling control on the basis of the detection region DR, and the detection region DR may be included in the central cooling region CCR. The cooling device 10000 may perform feedback cooling control for the target region TR on the basis of the temperature of the detection region DR so as to generate a desired effect (for example, tumor removal) in the target region TR and prevent a negative effect (for example, necrosis) in regions other than the target region TR.

The detection region DR may be smaller than the cooling region CR. The detection region DR may be smaller than the central cooling region CCR. The detection region DR may include the lowest temperature point of the central cooling region CCR.

For example, the detection region DR may include the lowest temperature point of the central cooling region CCR and may be included in the central cooling region CCR. Here, the detection region DR may not include the non-cooling region NCR. The detection region DR may not include the boundary region BR.

According to an embodiment of the present application, as illustrated in FIG. 39, the temperature sensor 6100 may be disposed at a position deviating from a virtual straight line between the nozzle unit 4100 and the target region TR. This may be a design to prevent the temperature sensor 6100 from being damaged due to the coolant sprayed from the nozzle unit 4100.

The detection region DR of the temperature sensor 6100 may be in a form closer to an elliptical shape than the central cooling region CCR. An outer shape of the detection region DR of the temperature sensor 6100 may have higher eccentricity than an outer shape of the central cooling region CCR. Here, the cooling device 10000 may perform cooling so that a coolant spraying direction is perpendicular to the surface of the subject to be treated to allow relatively uniform cooling of the surface of the subject to be treated, and simultaneously, the cooling device 10000 may be implemented with an optimal design that avoids damage to the temperature sensor 6100.

The detection region DR according to some embodiments for performing feedback cooling control have been disclosed above, and the detection region DR may be determined according to a direction in which the temperature sensor 6100 is installed, a distance between the temperature sensor 6100 and the subject to be treated, and features of the temperature sensor 6100.

However, features and installation directions of the temperature sensor 6100 that should be selected to implement the cooling device 10000 including the temperature sensor 6100 having a specific detection region DR may vary, and since those or ordinary skill in the art may easily make choices or change the design relating thereto, detailed description thereof will be omitted.

2.2.2 Control According to Temperature of Coolant in Reservoir 1100

The cooling device 10000 according to an embodiment of the present application may cool the temperature of the target region TR to a target cooling temperature on the basis of information on a coolant in the reservoir 1100.

The cooling device 10000 according to an embodiment of the present application may cool the temperature of the target region TR to a target cooling temperature on the basis of the temperature of the coolant in the reservoir 1100. The cooling device 10000 according to an embodiment of the present application may cool the temperature of the target region TR to a target cooling temperature on the basis of a calculated temperature of the coolant in the reservoir 1100.

In the case of the cooling device 10000 using a coolant, the temperature of the sprayed coolant may be changed according to the temperature of the stored coolant. In this case, a problem may occur in that the temperature of the target region TR cannot be constantly controlled to a target cooling temperature because the temperature of the target region TR is determined according to the temperature of the stored coolant even when cooling is performed using the same cooling method. Therefore, in a case in which the cooling device 10000 according to an embodiment of the present application performs cooling in consideration of the temperature of the coolant in the reservoir 1100, there may be an advantage in that the cooling device 10000 may operate as a more precise, stable cooling device 10000.

For example, the control unit 5000 of the cooling device 10000 may control the valve 2100 so that the temperature of the coolant sprayed to the target region TR is constant regardless of a temperature of the outside where the cooling device 10000 is used. As another example, the control unit 5000 of the cooling device 10000 may control the valve 2100 so that the temperature of the target region TR is cooled to a target cooling temperature regardless of the temperature of the outside where the cooling device 10000 is used.

In order to measure the temperature of the coolant in the reservoir 1100, the cooling device 10000 may be in a form in which the temperature sensor 6100 configured to measure the temperature of the coolant in the reservoir 1100 is installed in the reservoir 1100.

However, it may be necessary to devise a new method because, when the temperature sensor 6100 is placed inside the reservoir 1100 to measure the temperature of the coolant in the reservoir 1100 using the temperature sensor 6100, costs may be high because, every time the reservoir 1100 is replaced, the temperature sensor 6100 is also replaced, and the temperature sensor 6100 disposed inside the reservoir 1100 may not operate normally due to a pressure of the coolant accommodated in the reservoir 1100.

Figure 42:
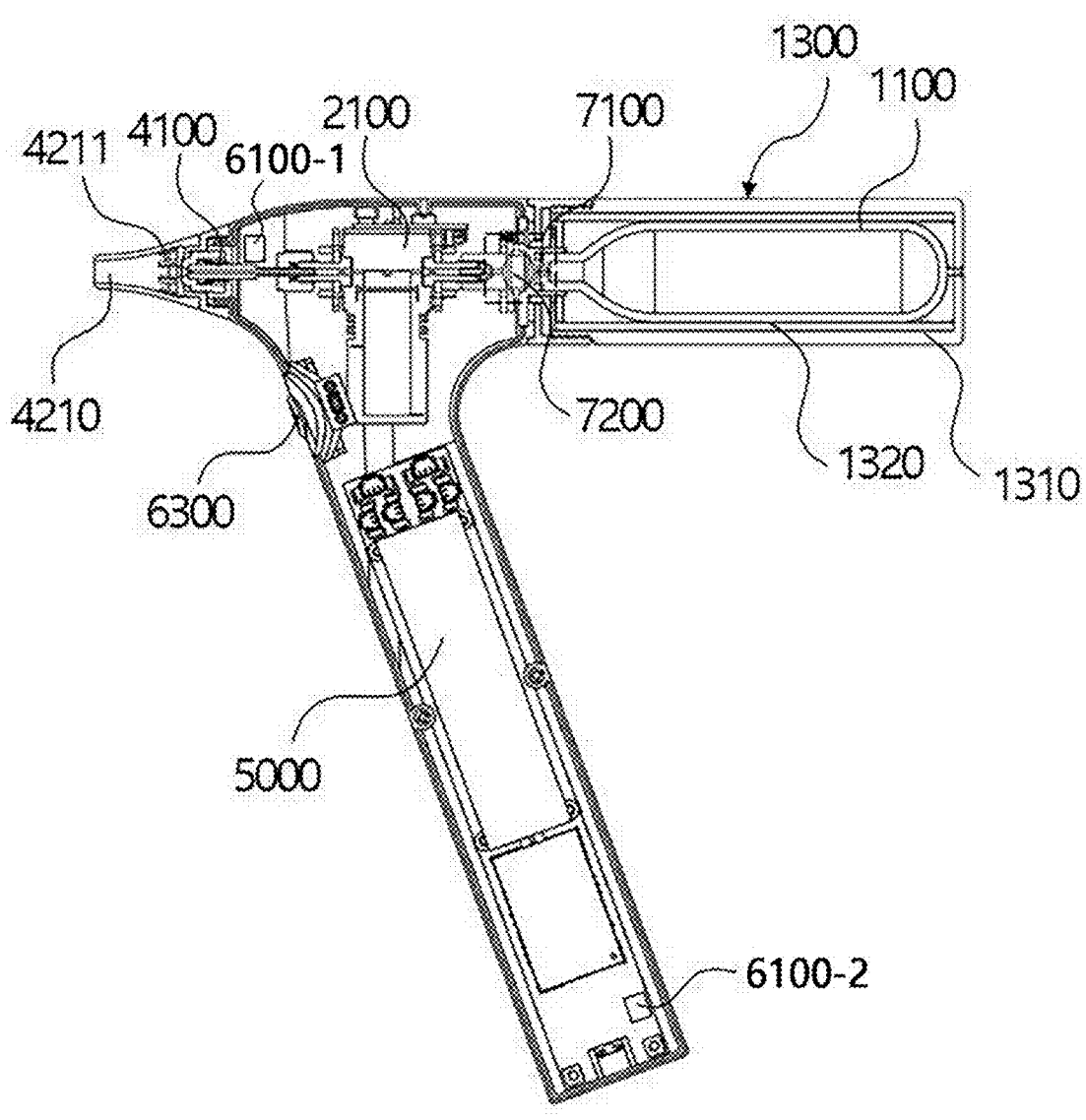
FIG. 42 is a diagram for describing the cooling device 10000 that performs control according to a temperature of a coolant of a reservoir 1100 according to an embodiment of the present application.

FIG. 42 is a diagram for describing the cooling device 10000 that performs control according to the temperature of the coolant in the reservoir 1100 according to an embodiment of the present application.

According to an embodiment of the present application, the cooling device 10000 may include one or more temperatures sensors 6100 to calculate the temperature of the coolant included in the reservoir 1100.

Referring to FIG. 42, the cooling device 10000 may include a plurality of temperature sensors 6100 to calculate the temperature of the coolant included in the reservoir 1100.

For example, the cooling device 10000 may include a first temperature sensor 6100-1 configured to sense a temperature related to the temperature of the sprayed coolant and a second temperature sensor 6100-2 configured to sense a temperature of the outside related to an environment in which the cooling device 10000 is used.

In order to sense the temperature related to the temperature of the sprayed coolant, the cooling device 10000 may include the first temperature sensor 6100-1 configured to measure the temperature of the nozzle unit 4100. For example, a contact-type temperature sensor 6100-1 may be formed to come in contact with an outer side of the nozzle unit 4100, and the contact-type temperature sensor 6100-1 may sense the temperature of the outer side of the nozzle unit 4100. However, the position of the first temperature sensor 6100-1 is not limited to the corresponding position, and the first temperature sensor 6100-1 configured to measure the temperature related to the temperature of the sprayed coolant may be included to be disposed at other positions in the cooling device 10000.

In order to sense the temperature of the outside related to the environment in which the cooling device 10000 is used, the cooling device 10000 may include the second temperature sensor 6100-2 configured to measure a temperature in a region different from a region in which the coolant flows. The cooling device 10000 may include the second temperature sensor 6100-2 spaced apart from the nozzle unit 4100 and a flow path of the coolant to sense the temperature of the outside related to the environment in which the cooling device 10000 is used.

For example, the second temperature sensor 6100-2 may be formed near a control board on which the control unit 5000 is formed, and the second temperature sensor 6100-2 may measure the temperature of a space in which the control board is disposed. However, the position of the second temperature sensor 6100-2 is not limited to the corresponding position, and the second temperature sensor 6100-2 configured to measure the temperature of the outside related to the environment in which the cooling device 10000 is used may be included to be disposed at other positions in the cooling device 10000.

According to an embodiment of the present application, the cooling device 10000 may calculate the temperature of the coolant in the reservoir 1100 on the basis of a first temperature value of the first temperature sensor 6100-1 and a second temperature value of the second temperature sensor 6100-2. In other words, the first temperature value related to the sprayed coolant may be sensed through the first temperature sensor 6100-1, the second temperature value related to the temperature of the outside where the cooling device 10000 is used may be sensed through the second temperature sensor 6100-2, and the control unit 5000 may calculate the temperature of the coolant in the reservoir 1100 on the basis of the first temperature value and the second temperature value.

The first temperature value and the second temperature value may be values continuously measured through the control unit 5000 of the cooling device 10000 and the plurality of temperature sensors 6100. Alternatively, the first temperature value and the second temperature value may be values temporarily measured through the control unit 5000 and the plurality of temperature sensors 6100 upon start of the cooling operation of the cooling device 10000.

The cooling device 10000 may control the valve 2100 on the basis of the calculated temperature of the coolant in the reservoir 1100. Information on a method of controlling the valve 2100 which will be performed according to the calculated temperature of the coolant in the reservoir 1100 may be pre-stored in the cooling device 10000.

According to an embodiment of the present application, the control unit 5000 may control the cooling device 10000 to selectively perform one of the first cooling mode and the second cooling mode on the basis of the temperature of the coolant in the reservoir 1100. For example, the cooling device 10000 may perform at least the first cooling mode or the second cooling mode on the basis of the calculated temperature of the coolant in the reservoir 1100.

The control unit 5000 may control the cooling device 10000 to operate in the first cooling mode in a case in which the temperature of the coolant in the reservoir 1100 is a predetermined numerical value or more. The control unit 5000 may control the cooling device 10000 to operate in the second cooling mode in a case in which the temperature of the coolant in the reservoir 1100 is less than the predetermined numerical value.

Here, the first cooling mode may be a mode in which the cooling extent and/or cooling speed is controlled so that relatively excessive cooling is performed as compared to the second cooling mode. For example, the valve 2100 may be opened during a first time in the first cooling mode and may be opened during a second time, which is shorter than the first time, in the second cooling mode.

However, the cooling device 10000 according to an embodiment of the present application may acquire the first temperature value and the second temperature value and then control the extent to which the target region TR is cooled, without calculating the temperature value of the reservoir 1100.

For example, the control unit 5000 may compare the first temperature value and the second temperature value to determine whether a coolant is being normally sprayed. The control unit 5000 may, on the basis of the determination, control the extent to which the target region TR is cooled. Here, a lookup table relating to the first temperature value and the second temperature value when the cooling device 10000 normally operates may be pre-stored in the cooling device 10000.

As another example, the control unit 5000 may compare the first temperature value and the second temperature value to determine whether the temperature inside the reservoir 1100 affects the temperature of the sprayed coolant. The control unit 5000 may, on the basis of the determination, control the extent to which the target region TR is cooled. Here, critical values relating to at least one of the first temperature value and the second temperature value may be pre-stored in the cooling device 10000.

2.2.3 Control According to Amount of Coolant Remaining in Reservoir 1100

The cooling device 10000 according to an embodiment of the present application may cool the temperature of the target region TR to a target cooling temperature on the basis of information related to the coolant in the reservoir 1100.

The cooling device 10000 according to an embodiment of the present application may cool the temperature of the target region TR to a target cooling temperature on the basis of the amount of coolant remaining in the reservoir 1100. The cooling device 10000 according to an embodiment of the present application may cool the temperature of the target region TR to a target cooling temperature on the basis of an internal pressure of the reservoir 1100 according to the amount of coolant remaining in the reservoir 1100.

In the case of the cooling device 10000 using a coolant, when the valve 2100 is opened due to pressure of the coolant flowing out from the reservoir 1100, the amount of jetted coolant and/or the amount of change in temperature of the coolant due to expansion may be changed. In this case, a problem may occur in that the temperature of the target region TR may not be constantly controlled to a target cooling temperature depending on the pressure of the stored coolant even when cooling is performed using the same cooling method. Therefore, in a case in which the cooling device 10000 according to an embodiment of the present application performs cooling in consideration of the amount of coolant remaining in the reservoir 1100, there may be an advantage in that the cooling device 10000 may operate as a more precise, stable cooling device 10000.

For example, the control unit 5000 of the cooling device 10000 may control the valve 2100 so that the temperature of the coolant sprayed to the target region TR is constant regardless of the amount of coolant remaining in the reservoir 1100, until the reservoir 1100 received by the reservoir receiving unit 1300 of the cooling device 10000 is replaced with a new reservoir 1100.

The cooling device 10000 according to an embodiment of the present application may check information on the amount of coolant remaining in the reservoir 1100.

For example, the cooling device 10000 may check information on the amount of coolant remaining in the reservoir 1100 on the basis of a value sensed through a pressure sensor. As a specific example, the cooling device 10000 may have a pressure sensor disposed between the reservoir 1100 and the reservoir receiving unit 1300 to measure a separation distance between the reservoir 1100 and the reservoir receiving unit 1300 that is caused by a decrease in the amount of coolant remaining in the reservoir 1100. The cooling device 10000 may check the amount of coolant remaining in the reservoir 1100 on the basis of the value of the pressure sensor. As another specific example, the cooling device 10000 may include a pressure sensor configured to measure pressure in a pipe formed to allow a coolant to flow between the reservoir 1100 and the valve 2100, and the cooling device 10000 may check the amount of coolant remaining in the reservoir 1100 on the basis of a value of the pressure sensor.

As another example, the cooling device 10000 may perform an operation to check information on the residual amount of coolant through the control unit 5000 to check the amount of coolant remaining in the reservoir 1100. As a specific example, the cooling device 10000 may calculate the amount of coolant remaining in the reservoir 1100 through counting the number of cooling operations of the control unit 5000. The cooling device 10000 may count the number of cooling every time one cooling operation is performed and may reset the counted number of cooling every time the reservoir 1100 is replaced.

According to an embodiment of the present application, the cooling device 10000 may include a first control unit 5000 configured to involve in opening of the valve 2100 (that is, performance of a cooling operation) and a second control unit 5000 configured to involve in checking the residual amount of coolant (that is, counting the number of cooling operations performed). The cooling device 10000 may include a first power source unit configured to supply power to the first control unit 5000 and a second power source unit configured to supply power to the second control unit 5000. The second power source unit may be turned on even in a state in which the first power source unit is turned off and may provide power for the second control unit 5000 to perform control to reset the counted number of cooling at a time point at which the reservoir 1100 is replaced.

According to another embodiment of the present application, the cooling device 10000 may include a control unit 5000 configured to involve in opening of the valve 2100 (that is, performance of a cooling operation) and checking the residual amount of coolant (that is, counting the number of cooling operations performed). The cooling device 10000 may include a power source unit configured to supply power to the control unit 5000, and even when the cooling operation is not being performed, the power source unit may provide power to the control unit 5000 to allow the control unit 5000 to perform control to reset the counted number of cooling at a time point at which the reservoir 1100 is replaced.

The information on the residual amount of coolant may be checked before the cooling device 10000 performs a cooling operation. The information on the residual amount of coolant may be checked when the cooling device 10000 performs a cooling operation. The information on the residual amount of coolant may be checked after the cooling device 10000 performs a cooling operation.

According to an embodiment of the present application, the cooling device 10000 may check the information on the amount of coolant remaining in the reservoir 1100 to determine a cooling mode on the basis of the residual amount of coolant.

The cooling device 10000 may control the valve 2100 on the basis of the amount of coolant remaining in the reservoir 1100. Information on a method of controlling the valve 2100 which will be performed according to the amount of coolant remaining in the reservoir 1100 may be pre-stored in the cooling device 10000.

According to an embodiment of the present application, the control unit 5000 may control the cooling device 10000 to selectively perform one of the first cooling mode and the second cooling mode on the basis of the amount of coolant remaining in the reservoir 1100. For example, the cooling device 10000 may check the information on the amount of coolant remaining in the reservoir 1100 and may perform cooling in the first cooling mode when the residual amount of coolant is a predetermined critical value or less. The cooling device 10000 may check the information on the amount of coolant remaining in the reservoir 1100 and may perform cooling in the second cooling mode when the residual amount of coolant is greater than the predetermined critical value.

Here, the first cooling mode may be a mode in which the cooling extent and/or cooling speed is controlled so that relatively excessive cooling is performed as compared to the second cooling mode.

For example, the valve 2100 may be opened during a first time in the first cooling mode and may be opened during a second time, which is shorter than the first time, in the second cooling mode.

As another example, in the first cooling mode, the valve 2100 may, during the first time, repeat an operation of being opened during the seventh time and being closed during the eighth time. In the second cooling mode, the valve 2100 may, during the second time, repeat an operation of being opened during the ninth time and being closed during the tenth time.

Here, the control unit 5000 may control the valve 2100 so that the seventh time is the same as the ninth time and the eighth time is shorter than the tenth time so as to control the opening time of the valve 2100 per unit time in the first cooling mode to be longer as compared to the second cooling mode.

Alternatively, the control unit 5000 may control the valve 2100 so that the seventh time is the same as the ninth time, the eighth time is shorter than the tenth time, and the first time is longer than the second time so as to control the opening time of the valve 2100 per unit time and the total opening time of the valve 2100 in the first cooling mode to be longer as compared to the second cooling mode.

2.3 Modified Cooling Control

The cooling device 10000 according to an embodiment of the present application may perform modified cooling control. The cooling device 10000 according to an embodiment of the present application may perform improved cooling control. For example, the cooling device 10000 may provide radiant energy to one region of a subject to be treated including a target region TR through the radiant energy provision unit 4230 to control the size and/or shape of a region cooled to a target cooling temperature, the cooling region CR, the central cooling region CCR, and/or the boundary region BR.

Figure 43:
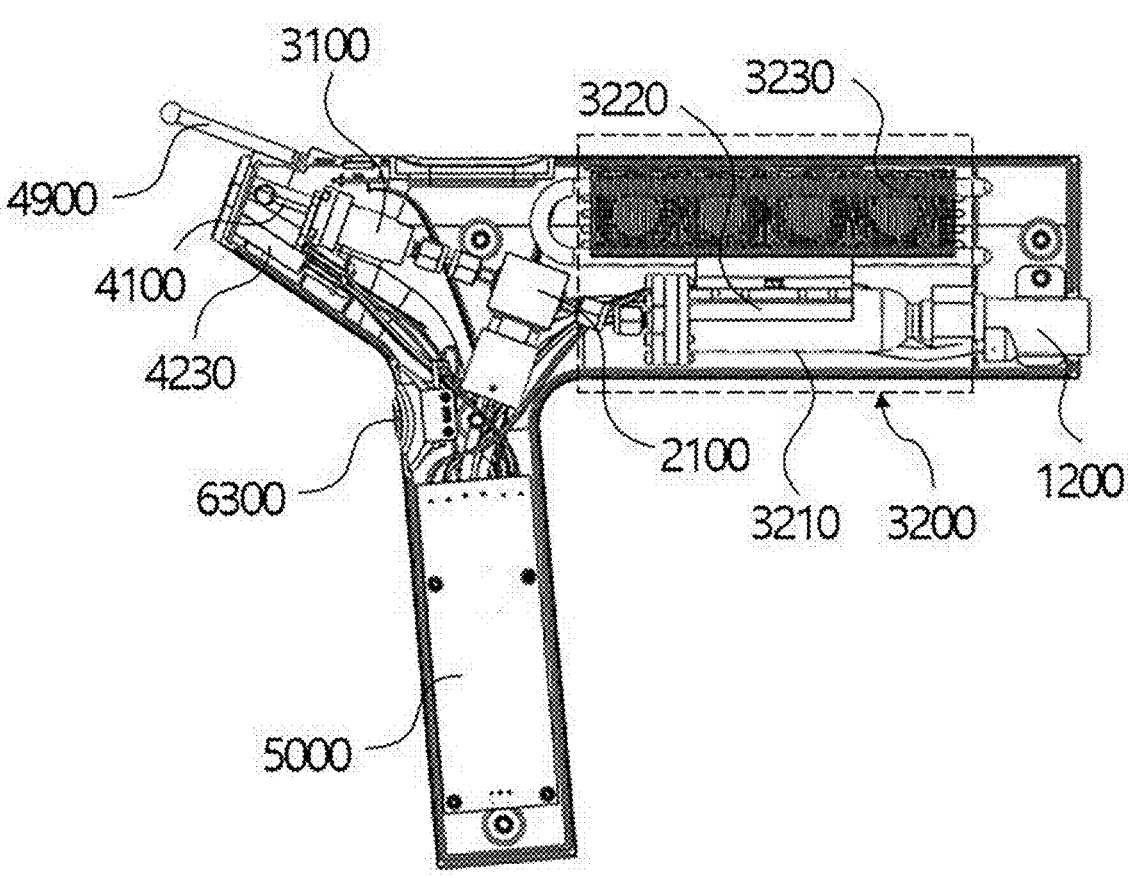
FIG. 43 is a diagram for describing a configuration of the cooling device 10000 according to an embodiment of the present application.

FIG. 43 is a diagram for describing a configuration of the cooling device 10000 according to an embodiment of the present application.

The cooling device 10000 according to an embodiment of the present application may include the radiant energy provision unit 4230. In the cooling device 10000, the radiant energy provision unit 4230 may be disposed at a position deviating from a straight line between the nozzle unit 4100 and the target region TR. This may be a design to prevent the radiant energy provision unit 4230 from being damaged due to the coolant sprayed from the nozzle unit 4100.

For example, the cooling device 10000 may include a nozzle unit 4100 configured to spray a coolant in a vertical direction with respect to the surface of the subject to be treated and the radiant energy provision unit 4230 configured to provide radiant energy in a direction different the direction in which the nozzle unit 4100 sprays the coolant with respect to the surface of the subject to be treated. As a specific example, the cooling device 10000 may be in a state in which the nozzle unit 4100 and the radiant energy provision unit 4230 are implemented so that an angle of 15° is formed between a virtual straight line between the center of the target region TR and the nozzle unit 4100 and a virtual straight line between the center of the target region TR and the radiant energy provision unit 4230.

According to an embodiment of the present application, in the cooling device 10000, the radiant energy provision unit 4230 configured to emit radiant energy may be installed at the same side as the side of the nozzle unit 4100 from which a coolant is sprayed. For example, the nozzle unit 4100 may face the subject to be treated including the target region TR, and the radiant energy provision unit 4230 may face the subject to be treated.

The radiant energy provision unit 4230 may be controlled by the control unit 5000. For example, the cooling device 10000 may include a first control unit 5000 configured to control the valve 2100 and a second control unit 5000 configured to control the radiant energy provision unit 4230. As another example, the control unit 5000 may control the valve 2100 and the radiant energy provision unit 4230. As a specific example, when the cooling device 10000 performs a cooling operation, the control unit 5000 may control the coolant to be sprayed through the nozzle unit 4100 and radiant energy to be provided through the radiant energy provision unit 4230.

The control unit 5000 may control the radiant energy provision unit 4230 and the valve 2100 so that a region of a subject to be treated to which the radiant energy emitted from the radiant energy provision unit 4230 is provided (hereinafter referred to as "radiant energy providing region") overlaps with a region of the subject to be treated to which the coolant is sprayed through the nozzle unit 4100 (hereinafter referred to as "coolant providing region"). For example, the radiant energy providing region may be included in the coolant providing region. As another example, the coolant providing region may be included in the radiant energy providing region.

The control unit 5000 may control the valve 2100 and the radiant energy provision unit 4230 so that, when the coolant is sprayed through the nozzle unit 4100, the radiant energy provision unit 4230 emits radiant energy to at least a partial region of the cooling region CR of the nozzle unit 4100. For example, the control unit 5000 may control the valve 2100 and the radiant energy provision unit 4230 so that, while a coolant is sprayed through the nozzle unit 4100, the radiant energy provision unit 4230 emits radiant energy to at least a partial region of the cooling region CR of the nozzle unit 4100. As another example, the control unit 5000 may control the valve 2100 and the radiant energy provision unit 4230 so that the radiant energy provision unit 4230 emits radiant energy to at least a partial region of the cooling region CR of the nozzle unit 4100 from before the coolant is sprayed through the nozzle unit 4100 to after the spraying of the coolant ends.

According to an embodiment of the present application, the cooling device 10000 may provide radiant energy so that the radiant energy providing region has a region overlapping with the cooling region CR in order to limit the central cooling region CCR. Here, the type of radiant energy provided through the radiant energy provision unit 4230, the intensity of radiant energy, and/or the radiant energy providing region may be selected according to the use of the cooling device 10000.

According to an embodiment of the present application, in order to limit a region cooled to a target cooling temperature, the cooling device 10000 may provide radiant energy to at least a partial region of the cooling region CR.

For example, the cooling device 10000 may provide radiant energy to the barrier of the target region TR to provide radiant energy to at least a partial region of the cooling region CR so that the region cooled to the target cooling temperature is limited to a region corresponding to the target region TR.

As a specific example, the nozzle unit 4100 may spray a coolant so that the coolant spraying region has a temperature lower than human body temperature, and an average temperature of the target region TR has a temperature corresponding to the target cooling temperature. The radiant energy provision unit 4230 may emit radiant energy so that the radiant energy providing region has a temperature higher than the average temperature of the target region TR. The cooling device 10000 may provide radiant energy to the barrier of the target region TR and spray a coolant to at least the target region TR to control the region cooled to the target cooling temperature to be limited to the region corresponding to the target region TR.

As another example, the cooling device 10000 may provide radiant energy to surround the central cooling region CCR and may spray a coolant to a region including the central cooling region CCR so that a region cooled to a target cooling temperature corresponds to the central cooling region CCR.

As still another example, the cooling device 10000 may provide radiant energy to surround the central cooling region CCR, which is formed when cooling is performed without the radiant energy provision unit 4230 emitting radiant energy, to limit a cooling region so that a region cooled to a target cooling temperature corresponds to the central cooling region CCR formed when cooling is performed with the radiant energy provision unit 4230 emitting radiant energy.

In the cooling device 10000 according to an embodiment of the present application, a region to which heat is provided through radiant energy provided by the radiant energy provision unit 4230 may be different from a region on which cooling is performed through the coolant sprayed by the nozzle unit 4100. As a specific example, in a case in which cooling of the target region TR is performed using the cooling device 10000, a region on which cooling should be performed through the nozzle unit 4100 may be the target region TR. Here, the region to which radiant energy should be provided through the radiant energy provision unit 4230 may be a region other than the target region TR.

Therefore, the lowest temperature point of the cryogen spraying region may not overlap with the radiant energy providing region. The radiant energy provision unit 4230 may provide radiant energy so that the radiant energy providing region is disposed in an edge region of the target region TR. Therefore, the cooling device 10000 may cool the target region TR so that a region reaching the target cooling temperature due to spraying of the coolant corresponds to the target region TR.

The radiant energy provision unit 4230 may emit radiant energy that causes radiation heating. The radiant energy provision unit 4230 may emit radiant energy that causes heating of the radiant energy providing region.

There may be various kinds of light sources of the radiant energy provision unit 4230. For example, the radiant energy provision unit 4230 may include a Light Amplification by the Stimulated Emission of Radiation (LASER) emission device. As a specific example, the radiant energy provision unit 4230 may include $CO_2$ laser, intense pulsed light (IPL), pulsed dye laser (PDL), and/or Nd-YAG laser emission devices.

The kind of light source of the radiant energy provision unit 4230 may be determined according to a region that radiant energy should reach.

For example, in a case in which the radiant energy provision unit 4230 is $CO_2$ laser having a wavelength of 10,600 nm, the radiant energy provision unit 4230 may be used to provide heat to the epidermis. As a specific example, the control unit 5000 may control the valve to perform cooling for a predetermined amount of time so that the epidermis and dermis of the subject to be treated are cooled.

The control unit 5000 may control the radiant energy provision unit 4230 to provide radiant energy to heat the epidermis of the subject to be treated while cooling is performed. The cooling device 10000 may control the valve 2100 and the radiant energy provision unit 4230 so as to control the temperatures of the epidermis and dermis of the subject to be treated to be different from each other.

As another example, in a case in which the radiant energy provision unit 4230 is PDL having wavelengths of 580 nm, 590 nm, 595 nm, and 600 nm, the radiant energy provision unit 4230 may be used to provide heat to the dermis. The present disclosure is not limited thereto, and the kind of light source of the radiant energy provision unit 4230 and the wavelength and intensity thereof may be determined on the basis of the depth that radiant energy (and heat) should reach.

According to an embodiment of the present application, in order to control the radiant energy providing region of the radiant energy provision unit 4230, the radiant energy provision unit 4230 may include a light source 4232 and a light guide unit 4234.

Figure 44:
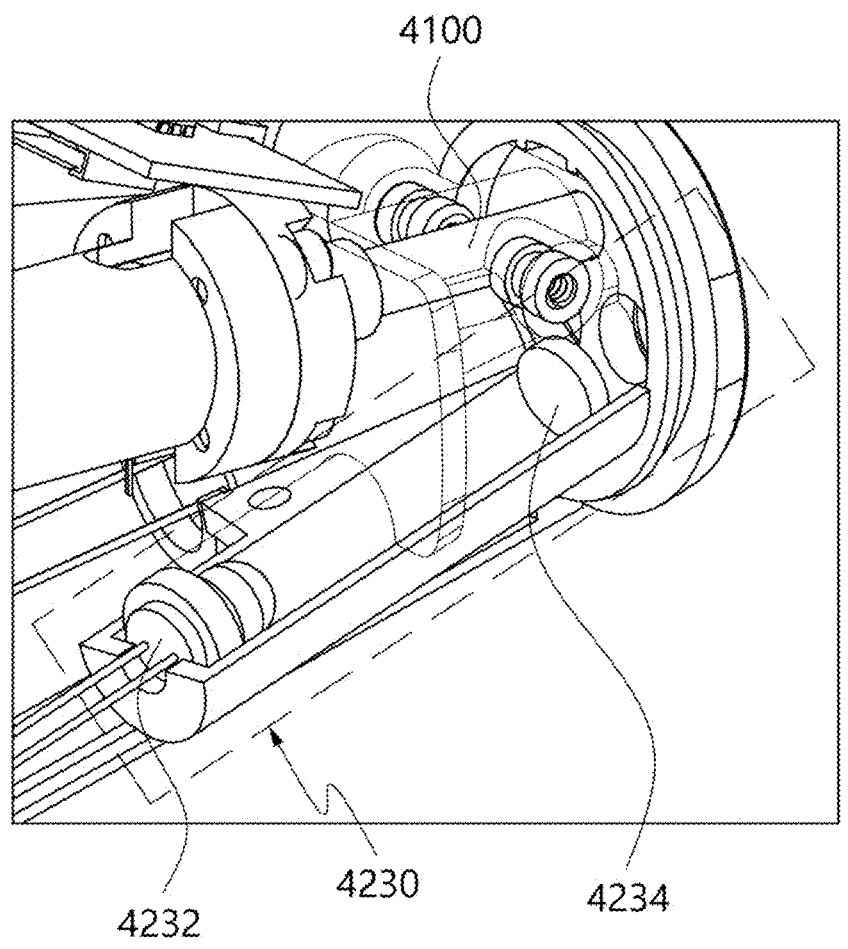
FIG. 44 is a diagram for describing a radiant energy provision unit 4230 according to an embodiment of the present application.

FIG. 44 is a diagram for describing the radiant energy provision unit 4230 according to an embodiment of the present application.

The radiant energy provision unit 4230 may include a light source 4232 configured to emit radiant energy and a light guide unit 4234 configured to guide the radiant energy emitted from the light source along a predetermined optical path.

The light source 4232 is a device configured to emit light, and there may be various kinds of light sources, and the intensity and region to which light is emitted may vary. As a specific example, the light source 4232 may be a LASER emission device.

The light guide unit 4234 may perform a function of refracting radiant energy. The light guide unit 4234 may perform a function of refracting incident light. The light guide unit 4234 may perform a function of changing a path of light emitted from the light source 4232. For example, the light guide unit 4234 may perform a function of gathering or dispersing light emitted from the light source 4232.

According to an embodiment of the present application, when the cooling device 10000 cools the target region TR, the radiant energy emitted from the light source 4232 may be irradiated in a form of surrounding the target region TR by the light guide unit 4234.

The control unit 5000 according to an embodiment of the present application may control the valve 2100 to be opened and closed so that the cooling device 10000 performs a cooling operation and may provide radiant energy to at least a partial region of the cooling region CR through the radiant energy provision unit 4230. For example, the control unit 5000 may control the valve 2100 and the radiant energy provision unit 4230 so that the radiant energy provision unit 4230 emits radiant energy while the valve 2100 is open. As another example, the control unit 5000 may control the valve 2100 and the radiant energy provision unit 4230 so that the radiant energy provision unit 4230 emits radiant energy while the cooling device 10000 performs a cooling operation. As a specific example, in a case in which the control unit 5000 controls the valve 2100 to repeat opening and closing in order to perform cooling, the control unit 5000 may control the radiant energy provision unit 4230 to provide radiant energy while cooling is performed, regardless of whether the valve 2100 is opened or closed.

According to an embodiment of the present application, the cooling device 10000 may control the intensity of radiant energy emitted from the radiant energy provision unit 4230 to derive a similar effect even when the radiant energy provision unit 4230 emits radiant energy throughout the target region TR and the periphery of the target region TR.

For example, the radiant energy provision unit 4230 may emit radiant energy with an intensity that is insufficient to prevent cooling due to spraying a coolant in the form of free jet FJ but is sufficient to prevent cooling due to spraying a coolant in the form of spread jet SJ so that, even when radiant energy is emitted throughout the target region TR and the periphery of the target region TR, the target region TR is cooled while excessive cooling of the periphery of the target region TR is prevented.

As a specific example, the control unit 5000 may, while the coolant that passed through the valve 2100 is sprayed to the target region TR, allow radiant energy emitted through the radiant energy provision unit 4230 to be provided to the target region TR and a region outside the target region TR. In the cooling device 10000, due to combination of the cooling phenomenon of the target region TR and the heating phenomenon of the radiant energy provision unit 4230, the lowest temperature point on the surface of the subject to be treated is not heated due to heating by the radiant energy emitted through the radiant energy provision unit 4230. Here, a specific region not being heated by radiant energy may mean that the temperature of the specific region is substantially the same in a case in which radiant energy by the radiant energy provision unit 4230 is provided to the specific region and a case in which the radiant energy by the radiant energy provision unit 4230 is not provided to the specific region.

As another example, the radiant energy provision unit 4230 may emit radiant energy with an appropriate intensity to allow radiant energy emitted through the radiant energy provision unit 4230 to be provided to the target region TR and the region outside the target region TR and to control a region corresponding to the target cooling temperature (hereinafter referred to as "target temperature region TTR") to correspond to a circular shape.

Figure 45:
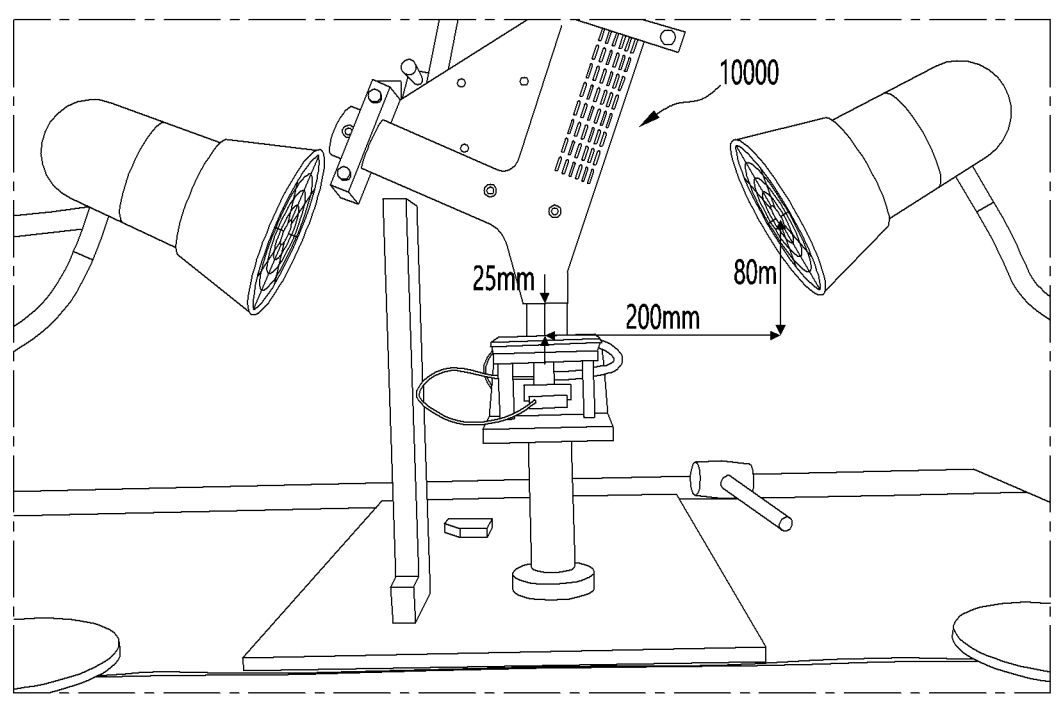
FIGS. 45 to 47 are diagrams for describing experiments for confirming that, when the cooling device 10000 according to an embodiment of the present application emits radiant energy, the target region TR is cooled and excessive cooling of the periphery of the target region TR is prevented, and results of the experiments.
Figure 46:
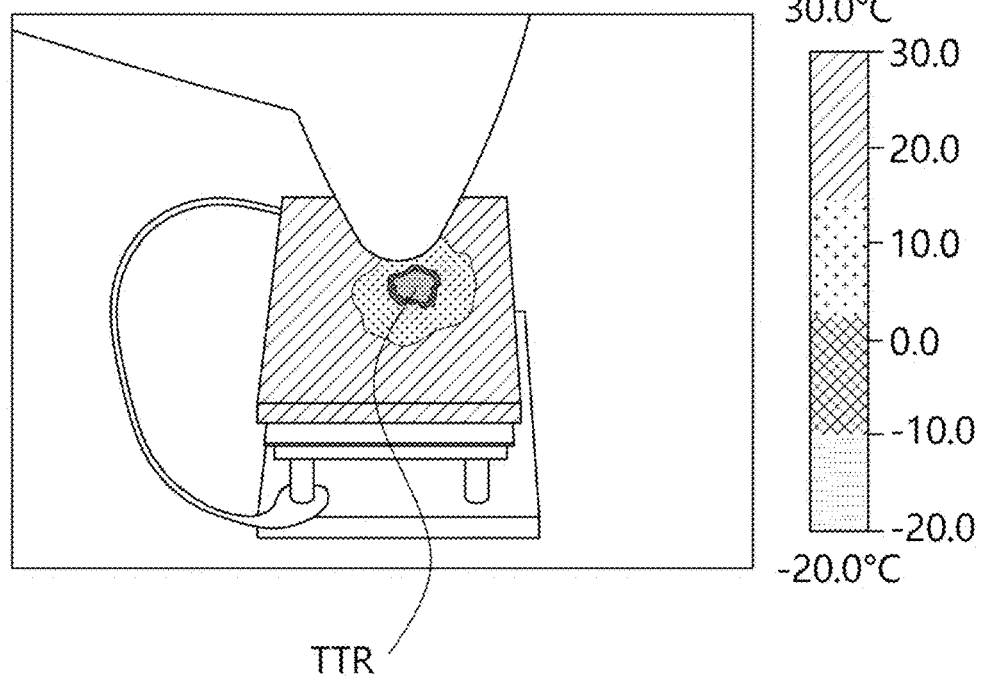
Figure 47:
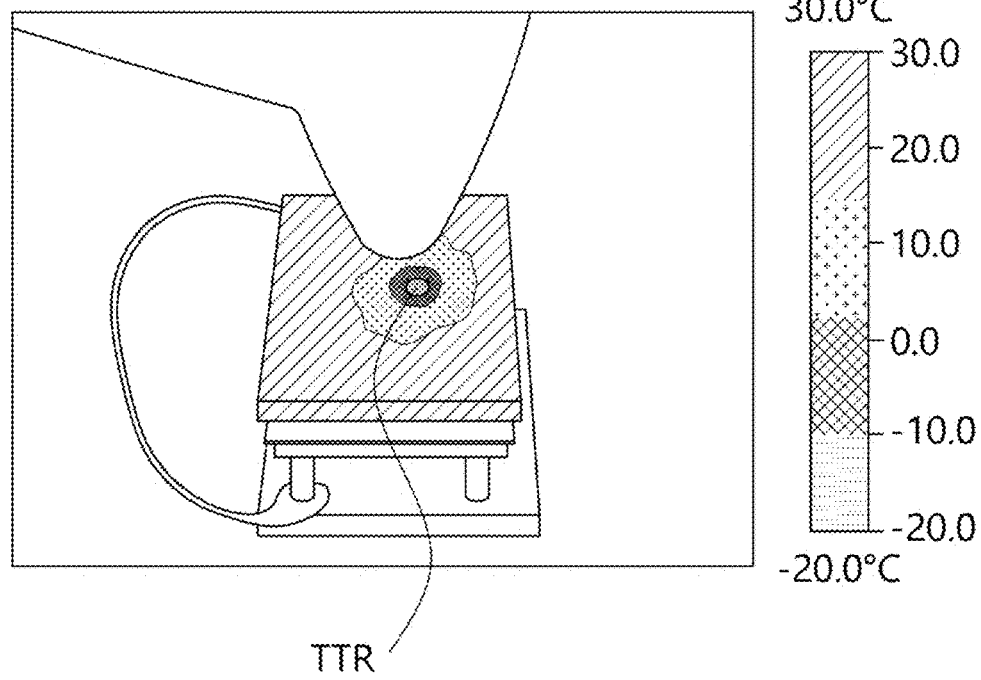

FIGS. 45 to 47 are diagrams for describing experiments for confirming that, when the cooling device 10000 according to an embodiment of the present application emits radiant energy, the target region TR is cooled and excessive cooling of the periphery of the target region TR is prevented, and results of the experiments.

Referring to FIG. 45, an experiment was conducted in a state in which the cooling device 10000 was installed to spray a coolant at a position spaced 25 mm away from the target region TR and two infrared irradiators (Ilsin Medical Co., Ltd, OR140) were disposed to face the target region TR to provide radiant energy thereto. The two infrared irradiators were set to emit radiant energy at an intensity of 80% of the intensity of the irradiator itself. Also, the infrared irradiators were disposed so that the center of light emitted by the infrared irradiators is located at a place that is 200 mm away from a side of the target region TR and 80 mm away from the top of the target region TR.

FIG. 46 shows an experimental result in a case in which a coolant was sprayed to the target region TR through the cooling device 10000 while the infrared irradiators were turned off, and FIG. 47 shows an experimental result in a case in which a coolant was sprayed to the target region TR through the cooling device 10000 while the infrared irradiators were turned on. In conducting the experiments of FIGS. 46 and 47, a coolant was sprayed for about 20 seconds using the cooling device 10000, and $CO_2$ was used as the coolant.

According to the experimental results, it was confirmed that, in FIG. 47, the size of the target temperature region TTR was reduced and the shape of the target temperature region TTR was relatively closer to a circle as compared to FIG. 46.

In this way, it was confirmed through the experiments that, at a time point at which the cooling device 10000 performs a cooling operation, even when radiant energy is provided to the target region TR and the periphery of the target region TR, the size and shape of the target temperature region TTR is controlled due to combination of the heating phenomenon by the radiant energy provided to the target region TR and the periphery of the target region TR and the cooling phenomenon by the coolant.

Details relating to the best mode for practicing the disclosure have been described above.

What is claimed is:

1. A tip structure configured to be equipped on a cooling device including a cooling medium, the tip structure comprising:

a front cover including:

an inner surface defining an internal space configured to receive the cooling medium, and an outer surface comprising a connection portion configured to mount the cooling device; and a cooling component configured to communicate heat between the cooling medium and a target, wherein the cooling component includes:

a contact portion comprising a contact surface configured to contact the target, and a locking portion configured to be mounted to the front cover, wherein one end of the front cover defines a hole corresponding to the contact portion of the cooling component, wherein a protrusion corresponding to the locking portion of the cooling component is formed inside the front cover, wherein, in response to the cooling component being mounted to the front cover, the locking portion of the cooling component is configured to be caught by the protrusion of the front cover and the contact portion of the cooling component is configured to protrude through the hole of the front cover, wherein a width of the internal space defined by the inner surface of the front cover is greater than a width of the cooling medium, and wherein, in response to the tip structure being mounted to the cooling device, the cooling medium is configured to have surface contact with the cooling component, while the cooling medium is not physically contacted with the inner surface of the front cover.

2. The tip structure of claim 1, wherein the front cover is made of a plastic, and the cooling component is made of a metal.

3. The tip structure of claim 1, wherein a heat capacity of the cooling component is 0.1 times or 5 times of a heat capacity of the cooling medium.

4. The tip structure of claim 1, wherein the inner space of the front cover has a cylindrical shape whose width gradually increases.

5. The tip structure of claim 1, wherein the connection portion of the front cover is coupled to the cooling device by a male-female connection.

6. A cooling device comprising:

a cooling assembly including:

a rear cover, and a cooling medium; and a tip structure including:

a cooling component configured to communicate heat between the cooling medium and a target, and a front cover accommodating the cooling component therein, wherein the front cover includes:

an inner surface defining an internal space configured to receive the cooling medium, and an outer surface comprising a connection portion configured to be mounted to the rear cover of the cooling assembly, wherein the cooling component includes:

a contact portion configured to contact the target, and a locking portion configured to connect the contact portion to the front cover, wherein one end of the front cover defines a hole corresponding to the contact portion of the cooling component, wherein a protrusion corresponding to the locking portion of the cooling component is formed inside the front cover, wherein, in response to the locking portion of the cooling component being caught by the protrusion of the front cover, the cooling component is configured to be disposed inside of the front cover to cause the contact portion of the cooling component to protrude through the hole, and wherein, in response to the front cover of the tip structure being equipped to the rear cover of the cooling assembly through the connection portion, the cooling medium is configured to physically contact the cooling component, while the cooling medium is not physically contacted with the inner surface of the front cover due to a width of the internal space of the front cover designed to be larger than a width of the cooling medium.

7. The cooling apparatus of claim 6, wherein the tip structure is removable from the cooling assembly.

8. The cooling apparatus of claim 6, wherein a cooling assembly further includes an elastic coupling portion coupled to the rear cover.

9. The cooling apparatus of claim 8, wherein the elastic coupling portion includes an elastic member, and wherein, in response to the tip structure being equipped to the cooling assembly, the elastic member is configured to provide an elastic force to the cooling medium to cause the cooling component and the cooling medium to be pressed into close contact with each other.

10. The cooling apparatus of claim 6, further comprising:

a temperature sensor configured to measure a temperature of the cooling medium, wherein the cooling medium has a groove and the temperature sensor is inserted into the cooling medium through the groove.

* * * * *